United States Patent
Jarjour et al.

(10) Patent No.: US 11,591,582 B2
(45) Date of Patent: Feb. 28, 2023

(54) TCRα HOMING ENDONUCLEASE VARIANTS

(71) Applicant: 2seventy bio, Inc., Cambridge, MA (US)

(72) Inventors: Jordan Jarjour, Seattle, WA (US); Mark Pogson, North Bend, WA (US)

(73) Assignee: 2seventy bio, Inc., Cambridge, MA (US)

( * ) Notice: Subject to any disclaimer, the term of this patent is extended or adjusted under 35 U.S.C. 154(b) by 993 days.

(21) Appl. No.: 16/340,257

(22) PCT Filed: Oct. 11, 2017

(86) PCT No.: PCT/US2017/056178
§ 371 (c)(1),
(2) Date: Apr. 8, 2019

(87) PCT Pub. No.: WO2018/071565
PCT Pub. Date: Apr. 19, 2018

(65) Prior Publication Data
US 2022/0186198 A1    Jun. 16, 2022

Related U.S. Application Data

(60) Provisional application No. 62/414,266, filed on Oct. 28, 2016, provisional application No. 62/406,689, filed on Oct. 11, 2016.

(51) Int. Cl.
*C12N 9/22* (2006.01)
*C12N 15/85* (2006.01)

(52) U.S. Cl.
CPC .............. *C12N 9/22* (2013.01); *C12N 15/85* (2013.01)

(58) Field of Classification Search
CPC .................................. C12N 9/22; C12N 15/85
See application file for complete search history.

(56) References Cited

U.S. PATENT DOCUMENTS

| | | | |
|---|---|---|---|
| 8,614,092 B2 | 12/2013 | Zhang et al. | |
| 9,017,967 B2 | 4/2015 | Bonas et al. | |
| 10,000,726 B2 * | 6/2018 | Man | C11D 11/0023 |
| 10,000,746 B2 | 6/2018 | Jarjour et al. | |
| 2011/0158957 A1 | 6/2011 | Bonini et al. | |
| 2013/0315884 A1 | 11/2013 | Galetto et al. | |
| 2014/0208457 A1 | 7/2014 | Fonfara et al. | |
| 2016/0130569 A1 * | 5/2016 | Jarjour | C12N 9/22 435/320.1 |

FOREIGN PATENT DOCUMENTS

| | | | |
|---|---|---|---|
| JP | 2016520320 A | 7/2016 | |
| WO | WO 2011/156430 A2 | 12/2011 | |
| WO | WO-2011156430 A2 * | 12/2011 | ......... C12N 15/1034 |
| WO | WO 2014/191527 A1 | 12/2014 | |
| WO | WO 2018/071565 A1 | 4/2018 | |

OTHER PUBLICATIONS

French S. and Robson B., "What is conservative substitution?", Journal of Molecular Evolution, 1983, vol. 19, pp. 171-175. (Year: 1983).*
Takeuchi et al. "Tapping natural reservoirs of homing endonucleases for targeted gene modification", PNAS, 2011, vol. 108, No. 32, pp. 13077-13082. (Year: 2011).*
Baxter Sarah et al: "Engineering domain fusion chimeras from 1-Onul family LAGLIDADG homing endonucleases.", Nucleic Acids Research Sep. 2012, vol. 40, No. 16, Sep. 2012 (Sep. 2012), pp. 7985-8000.
Boissel et al: "megaTALs: a rare-cleaving nuclease architecture for therapeutic genome engineering", Nucleic Acids Research, vol. 42, No. 4, Nov. 26, 2013 (Nov. 26, 2013), pp. 2591-2601.
Boissel et al., "megaTALs: a rare-cleaving nuclease architecture for therapeutic genome engineering" Nucleic Acids Res. Feb. 2014;42(4):2591-601.
Branden et al. Introduction to Protein Structure, Garland Publishing Inc., New York, p. 247, 1991.
Hafez Mohamed et al: "Homing endonucleases: DNA scissors on a mission", Genome, vol. 55, No. 8, Aug. 2012 (Aug. 2012), pp. 553-569.
International Preliminary Report on Patentability for International Application No. PCT/EP2014/061189, dated Dec. 1, 2015, 9 pages.
International Search Report and Written Opinion for International Application No. PCT/EP2014/061189, dated Nov. 3, 2014, 14 pages.
International Preliminary Report on Patentability for International Application No. PCT/US2017/056178, dated Jan. 29, 2018, 10 pages.
International Search Report and Written Opinion for International Application No. PCT/US2017/056178, dated Jan. 29, 2018, 10 pages.
Jarjour et al., "High-resolution profiling of homing endonuclease binding and catalytic specificity using yeast surface display," 2009. Nuc. Acids Res. 37(20): 6871-6880.
Kay et al., "A bacterial effector acts as a plant transcription factor and induces a cell size regulator," Science. Oct. 26, 2007;318(5850):648-51.
Lamb et al., "Directed evolution of the TALE N-terminal domain for recognition of all 50 bases," Published online Aug. 26, 2013, Nucleic Acids Research, 2013, vol. 41, No. 21 9779-9785.
Osborn et al., "Evaluation of TCR Gene Editing Achieved by TALENs, CRISPR/Cas9, and megaTAL Nucleases," www.moleculartherapy.org, vol. 24, No. 3, 570-581 Mar. 2016.

(Continued)

*Primary Examiner* — Neil P Hammell
*Assistant Examiner* — Deepa Mishra
(74) *Attorney, Agent, or Firm* — Panitch Schwarze Belisario & Nadel LLP; Stephany G. Small; Travis W. Bliss

(57) ABSTRACT

The present disclosure provides improved genome editing compositions and methods for editing a TCRα gene.

15 Claims, 23 Drawing Sheets

Specification includes a Sequence Listing.

(56) References Cited

OTHER PUBLICATIONS

Perrino et al., "The Human TREX2 3' → 5'-Exonuclease Structure Suggests a Mechanism for Efficient Nonprocessive DNA Catalysis," The Journal of Biological Chemistry, vol. 280, No. 15, Issue of Apr. 15, pp. 15212-15218, 2005.

Provasi Elena et al: "TCR Gene Editing Results in Effective Immunotherapy of Leukemia without the Development of GvHD", Blood, American Society of Hematology, US, vol. 118, No. 21, Dec. 13, 2011 (Dec. 13, 2011), p. 307.

Takeuchi et al:"Tapping natural reservoirs of homing endonucleases for targeted gene modification", Proceedings of the National Academy of Sciences, National Academy of Sciences, vol. 108, o. 32, Aug. 1, 2011 {Aug. 1, 2011), pp. 13077-13082.

Stoddard, "Homing endonuclease structure and function," Quarterly Reviews of Biophysics 2005; 38(1): pp. 49-45.

Stoddard, "Homing Endonucleases: From Microbial Genetic Invaders to Reagents for Targeted DNA Modification," Structure 19, Jan. 12, 2011, 9 pages.

Torikai Hiroki et al:"A foundation for universal T-cell based immunotherapy: T cells engineered to express a CD19-specific chimeric-antigen-receptor and eliminate expression of endogenous TCR.", BLOODJun. 14, 2012, vol. 119, No. 24, Jun. 14, 2012 {Jun. 14, 2012), pp. 5697-5705.

Wilson, et al., Alanine to serine substitutions drive thermal adaption in a psychrophilic diatom cytochrome c6, 25 JBIC Journal of Biological Inorganic Chemistry 489-500 (2020).

Stockhaus et al., Serine-to-alanine substitutions at the amino-terminal region of phytochrome A result in an increase in biological activity, 6 Genes & Development 2364-2372 (1992).

Office Action dated Sep. 9, 2021 in Japanese Application No. 2019-540313.

\* cited by examiner

FIG. 1

|  | $n_{11}$ | $n_{10}$ | $n_9$ | $n_8$ | $n_7$ | $n_6$ | $n_5$ | $n_4$ | $n_3$ | $n_2$ | $n_1$ | $p_1$ | $p_2$ | $p_3$ | $p_4$ | $p_5$ | $p_6$ | $p_7$ | $p_8$ | $p_9$ | $p_{10}$ | $p_{11}$ |
|---|---|---|---|---|---|---|---|---|---|---|---|---|---|---|---|---|---|---|---|---|---|---|
| TCRa | T | G | T | C | T | G | C | C | T | A | T | T | C | A | C | C | G | A | T | T | T | T |
| KAT2B | A | G | T | A | T | G | C | C | T | A | T | T | C | T | A | C | A | A | G | A | A | A |

TCRα HOMING ENDONUCLEASE VARIANTS

CROSS REFERENCE TO RELATED APPLICATIONS

This application is the National Stage of International Application No. PCT/US2017/056178, filed Oct. 11, 2017, which claims the benefit under 35 U.S.C. § 119(e) of U.S. Provisional Application No. 62/414,266, filed Oct. 28, 2016, and U.S. Provisional Application No. 62/406,689, filed Oct. 11, 2016, each of which is incorporated by reference herein in its entirety.

STATEMENT REGARDING SEQUENCE LISTING

The Sequence Listing associated with this application is provided in text format in lieu of a paper copy, and is hereby incorporated by reference into the specification. The name of the text file containing the Sequence Listing is BLBD_077_02WO_ST25.txt. The text file is 114 KB, was created on Oct. 11, 2017, and is being submitted electronically via EFS-Web, concurrent with the filing of the specification.

BACKGROUND

Technical Field

The present disclosure relates to improved genome editing polypeptides and compositions. More particularly, the disclosure relates to nuclease variants and compositions, useful for editing the human T cell receptor alpha (TCRα) gene.

Description of the Related Art

The global burden of cancer doubled between 1975 and 2000. Cancer is the second leading cause of morbidity and mortality worldwide, with approximately 14.1 million new cases and 8.2 million cancer related deaths in 2012. The most common cancers are breast cancer, lung and bronchus cancer, prostate cancer, colon and rectum cancer, bladder cancer, melanoma of the skin, non-Hodgkin lymphoma, thyroid cancer, kidney and renal pelvis cancer, endometrial cancer, leukemia, and pancreatic cancer. The number of new cancer cases is projected to rise to 22 million within the next two decades.

The immune system has a key role in detecting and combating human cancer. The majority of transformed cells are quickly detected by immune sentinels and destroyed through the activation of antigen-specific T cells via clonally expressed T cell receptors (TCR). Accordingly, cancer can be considered an immunological disorder, a failure of immune system to mount the necessary anti-tumor response to durably suppress and eliminate the disease. In order to more effectively combat cancer, certain immunotherapy interventions developed over the last few decades have specifically focused on enhancing T cell immunity. These treatments have yielded only sporadic cases of disease remission, and have not had substantial overall success.

Most recently, adoptive cellular immunotherapy strategies, which are based on the isolation, modification, expansion and reinfusion of T cells, have been explored and tested in early stage clinical trials. T cells have often been the effector cells of choice for cancer immunotherapy due to their selective recognition and powerful effector mechanisms. These treatments have shown mixed rates of success, but a small number of patients have experienced durable remissions, highlighting the as-yet unrealized potential for T cell-based immunotherapies.

Thus, there is a need for more effective, targeted, safer, and persistent therapies to treat various forms of cancer and other immune disorders. In addition, there is a need for methods and compositions that can precisely and reproducibly disrupt endogenous TCR genes with high efficiency. Today's standards of care for most cancers fall short in some or all of these criteria.

BRIEF SUMMARY

The present disclosure generally relates, in part, to homing endonuclease (HE) variants and megaTALs that cleave a target site in exon 1 of the human TCRα gene, compositions comprising the HE variants and megaTALs, and methods of using the same.

In various embodiments, the present disclosure contemplates, in part, a polypeptide comprising an I-OnuI homing endonuclease (HE) variant that cleaves a target site in the human T cell receptor alpha (TCRα) gene, wherein the variant comprises the amino acid substitutions: L26I, R28D, N32R, K34N, S35E, V37N, G38R, S40R, E42S, G44R, V68K, A70T, G73S, N75R, S78M, K80R, L138M, T143N, S159P, S176A, C180H, F182G, I186K, S188V, S190G, K191T, L192A, G193K, Q195Y, Q197G, V199R, S201A, T203S, K207R, Y223S, K225R, S233R, D236E, and V238E of any one of SEQ ID NOs: 1-5, or a biologically active fragment thereof.

In various embodiments, the present disclosure contemplates, in part, a polypeptide comprising an I-OnuI homing endonuclease (HE) variant that cleaves a target site in the human T cell receptor alpha (TCRα) gene, wherein the variant comprises the amino acid substitutions: L26I, R28D, N32R, K34N, S35E, V37N, G38R, S40R, E42S, G44R, V68K, A70T, G73S, N75R, S78M, K80R, L138M, T143N, S159P, S176A, E178D, C180H, F182G, I186K, S188V, S190G, K191T, L192A, G193K, Q195Y, Q197G, V199R, S201A, T203S, K207R, Y223S, K225R, S233R, D236E, and V238E of any one of SEQ ID NOs: 1-5, or a biologically active fragment thereof.

In particular embodiments, the biologically active fragment lacks the 1, 2, 3, 4, 5, 6, 7, or 8 N-terminal amino acids compared to a corresponding wild type I-OnuI HE.

In certain embodiments, the biologically active fragment lacks the 4 N-terminal amino acids compared to a corresponding wild type I-OnuI HE.

In further embodiments, the biologically active fragment lacks the 8 N-terminal amino acids compared to a corresponding wild type I-OnuI HE.

In some embodiments, the biologically active fragment lacks the 1, 2, 3, 4, or 5 C-terminal amino acids compared to a corresponding wild type I-OnuI HE.

In additional embodiments, the biologically active fragment lacks the C-terminal amino acid compared to a corresponding wild type I-OnuI HE.

In particular embodiments, the biologically active fragment lacks the 2 C-terminal amino acids compared to a corresponding wild type I-OnuI HE.

In particular embodiments, the I-OnuI HE variant comprises an amino acid sequence that is at least 99% identical to the amino acid sequence set forth in any one of SEQ ID NOs: 7-8, or a biologically active fragment thereof.

In additional embodiments, the HE variant comprises the amino acid sequence set forth in SEQ ID NO: 7, or a biologically active fragment thereof.

In certain embodiments, the HE variant comprises the amino acid sequence set forth in SEQ ID NO: 8, or a biologically active fragment thereof.

In some embodiments, the polypeptide binds the polynucleotide sequence set forth in SEQ ID NO: 17.

In particular embodiments, the polypeptide further comprises a DNA binding domain.

In further embodiments, the DNA binding domain is selected from the group consisting of: a TALE DNA binding domain and a zinc finger DNA binding domain.

In additional embodiments, the TALE DNA binding domain comprises about 9.5 TALE repeat units, about 10.5 TALE repeat units, about 11.5 TALE repeat units, about 12.5 TALE repeat units, about 13.5 TALE repeat units, about 14.5 TALE repeat units, or about 15.5 TALE repeat units.

In some embodiments, the TALE DNA binding domain comprises 11.5 TALE repeat units and binds the polynucleotide sequence set forth in SEQ ID NO: 19.

In particular embodiments, the TALE DNA binding domain comprises 10.5 TALE repeat units and binds the polynucleotide sequence set forth in SEQ ID NO: 18.

In certain embodiments, the polypeptide binds and cleaves the polynucleotide sequence set forth in SEQ ID NO: 20.

In particular embodiments, the zinc finger DNA binding domain comprises 2, 3, 4, 5, 6, 7, or 8 zinc finger motifs.

In additional embodiments, the polypeptide further comprises a peptide linker and an end-processing enzyme or biologically active fragment thereof.

In particular embodiments, the polypeptide further comprises a viral self-cleaving 2A peptide and an end-processing enzyme or biologically active fragment thereof.

In some embodiments, the end-processing enzyme or biologically active fragment thereof has 5'-3' exonuclease, 5'-3' alkaline exonuclease, 3'-5' exonuclease, 5' flap endonuclease, helicase or template-independent DNA polymerase activity.

In further embodiments, the end-processing enzyme comprises Trex2 or a biologically active fragment thereof.

In particular embodiments, the polypeptide comprises the amino acid sequence set forth in any one of SEQ ID NOs: 10 to 12, or a biologically active fragment thereof.

In certain embodiments, the polypeptide comprises the amino acid sequence set forth in SEQ ID NO: 10, or a biologically active fragment thereof.

In additional embodiments, the polypeptide comprises the amino acid sequence set forth in SEQ ID NO: 11, or a biologically active fragment thereof.

In particular embodiments, the polypeptide comprises the amino acid sequence set forth in SEQ ID NO: 12, or a biologically active fragment thereof.

In various embodiments, a polynucleotide encoding a polypeptide contemplated herein is provided.

In particular embodiments, the present disclosure contemplates, in part, an mRNA encoding a polypeptide contemplated herein is provided.

In particular embodiments, the mRNA comprises the sequence set forth in any one of SEQ ID NOs: 16-19.

In some embodiments, a cDNA encoding a polypeptide contemplated herein is provided.

In certain embodiments, a vector comprising a polynucleotide encoding a polypeptide contemplated herein is provided.

In particular embodiments, a cell comprising a polypeptide contemplated herein is provided.

In further embodiments, a cell comprising a polynucleotide encoding a polypeptide contemplated herein is provided.

In additional embodiments, a cell comprising a vector contemplated herein is provided.

In particular embodiments, a cell edited by a polypeptide contemplated herein is provided.

In particular embodiments, the cell is a hematopoietic cell.

In some embodiments, the cell is a T cell.

In certain embodiments, the cell is a CD3+, CD4+, and/or CD8+ cell.

In particular embodiments, the cell is an immune effector cell.

In further embodiments, the cell is a cytotoxic T lymphocytes (CTLs), a tumor infiltrating lymphocytes (TILs), or a helper T cells.

In certain embodiments, the cell is a natural killer (NK) cell or natural killer T (NKT) cell.

In particular embodiments, the source of the cell is peripheral blood mononuclear cells, bone marrow, lymph nodes tissue, cord blood, thymus issue, tissue from a site of infection, ascites, pleural effusion, spleen tissue, or tumors.

BRIEF DESCRIPTION OF SEVERAL VIEWS OF THE DRAWINGS

FIG. 1 shows a comparison of on- and off-target sites (SEQ ID NOS: 17 and 21) for an I-OnuI HE variant designed to target a site in exon 1 of the TCRα gene constant region.

FIG. 3A-FIG. 3H shows yeast surface display cleavage plots for 64 possible nucleotide combinations and FIG. 3I shows a heat map of these activities.

BRIEF DESCRIPTION OF THE SEQUENCE IDENTIFIERS

Figure 2:
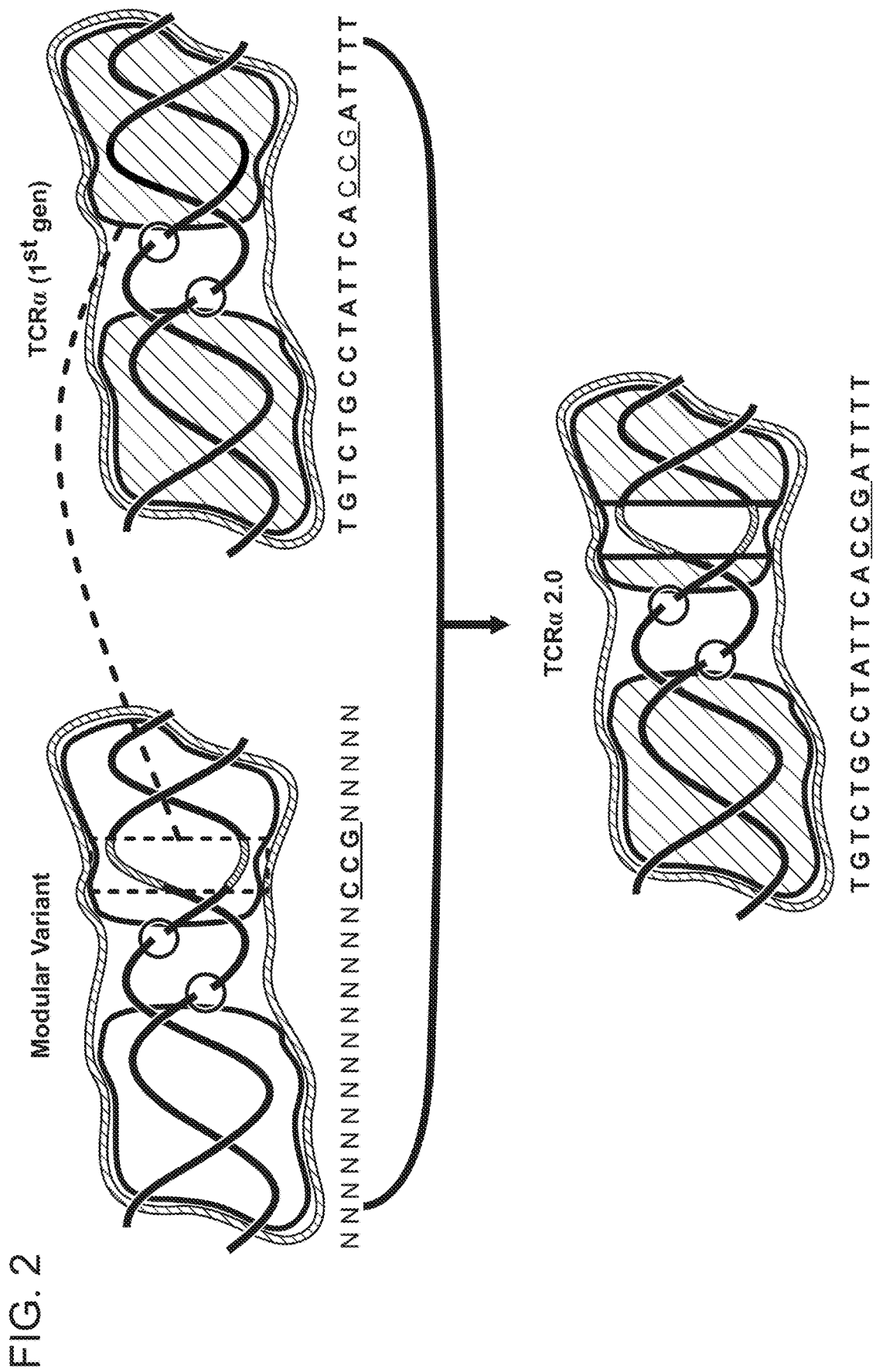
FIG. 2 shows a cartoon of the strategy for grafting a set of amino acids obtained from a modular HE variant, highly selective for "CCG" trinucleotide sequence (SEQ ID NOS: 17 and 67), into a first generation TCRα HE variant (SEQ ID NO: 6) to generate a second generation TCRα HE variant (TCRα2.0). The TCRα2.0 HE variant retains high selectivity for "CCG" at the desired substrate positions.
Figure 3A:
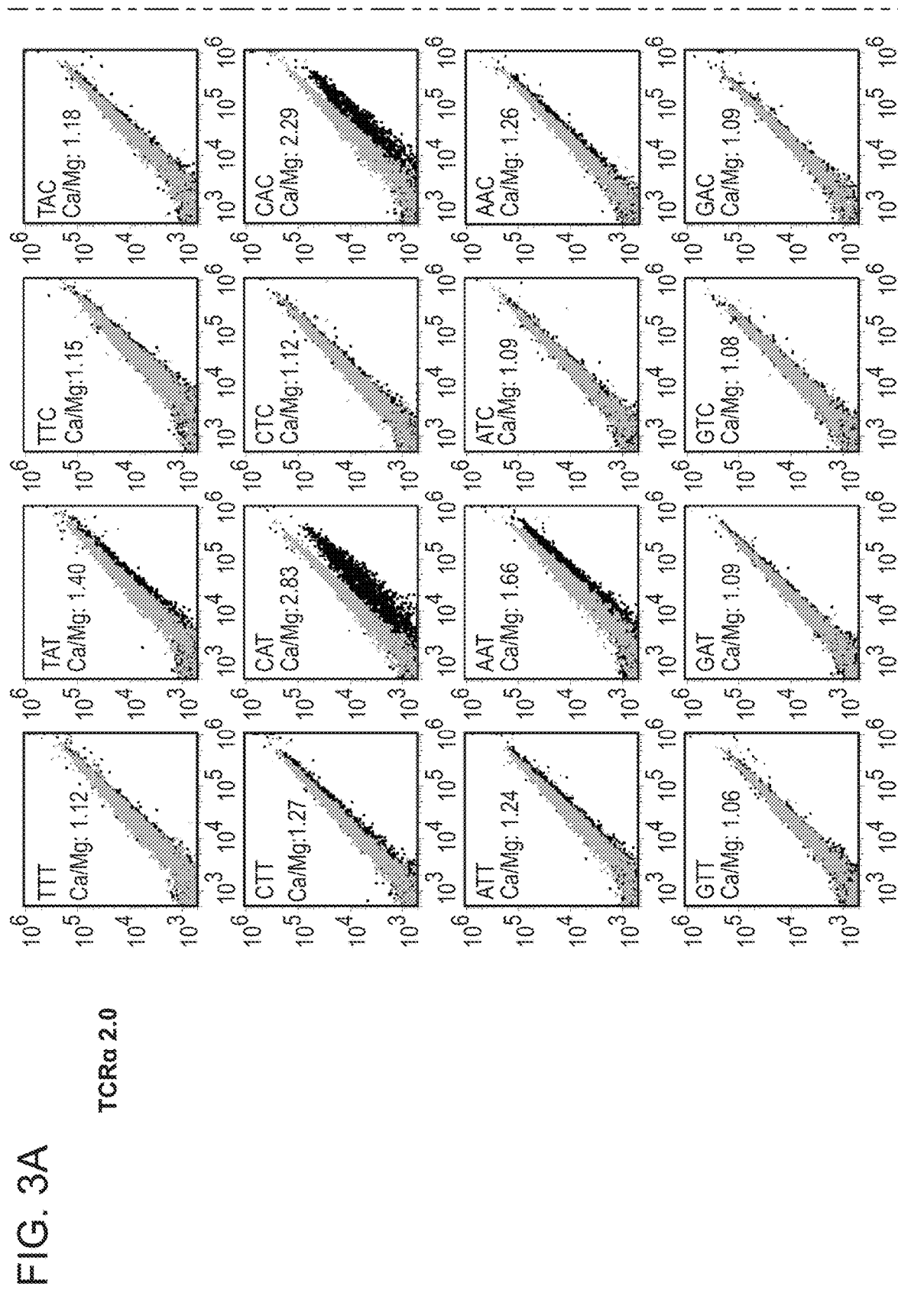
FIG. 3A to FIG. 3I shows the enhanced selectivity profiles for the first generation TCRα HE variant and the TCRα2.0 HE variant at substrate positions p456.
Figure 3B:
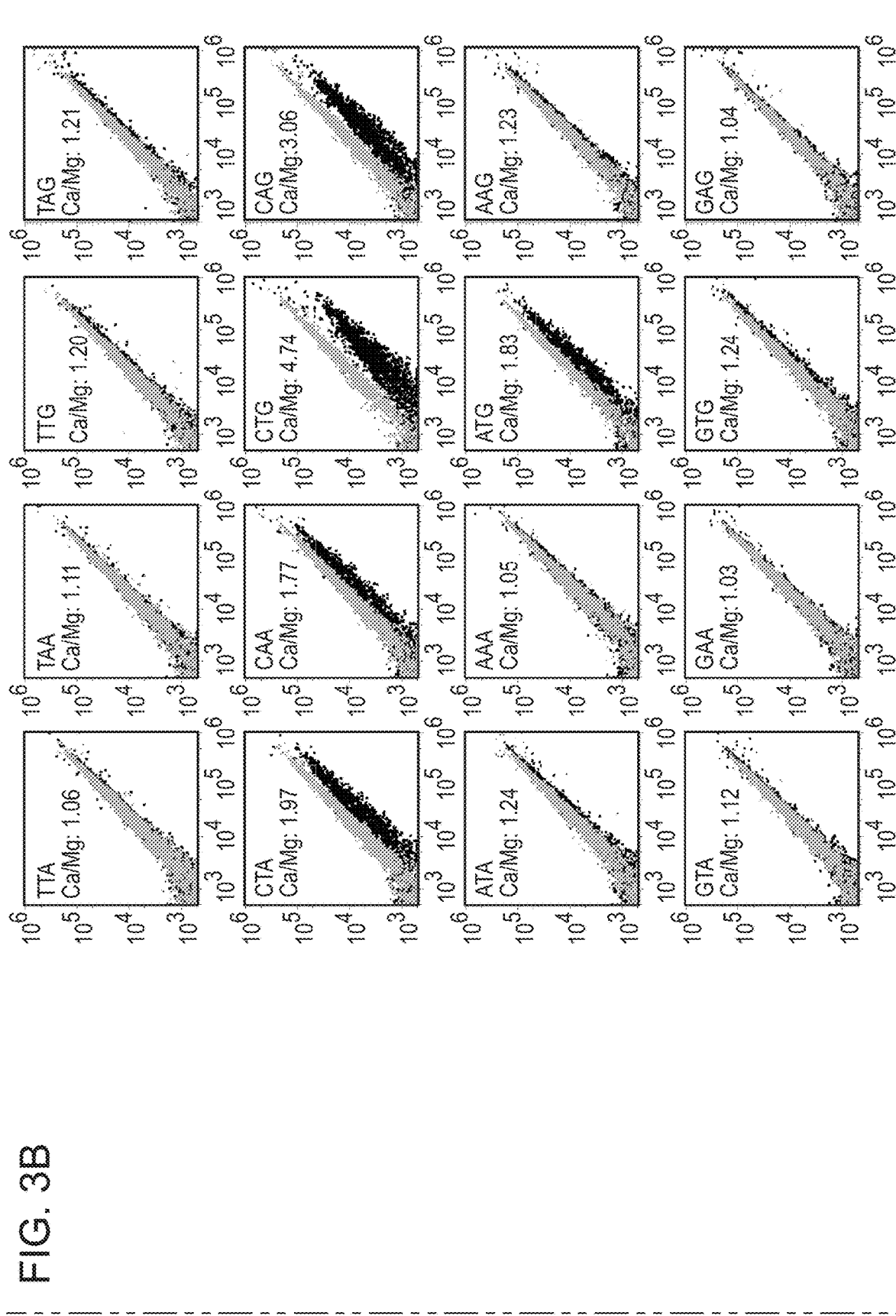
Figure 3C:
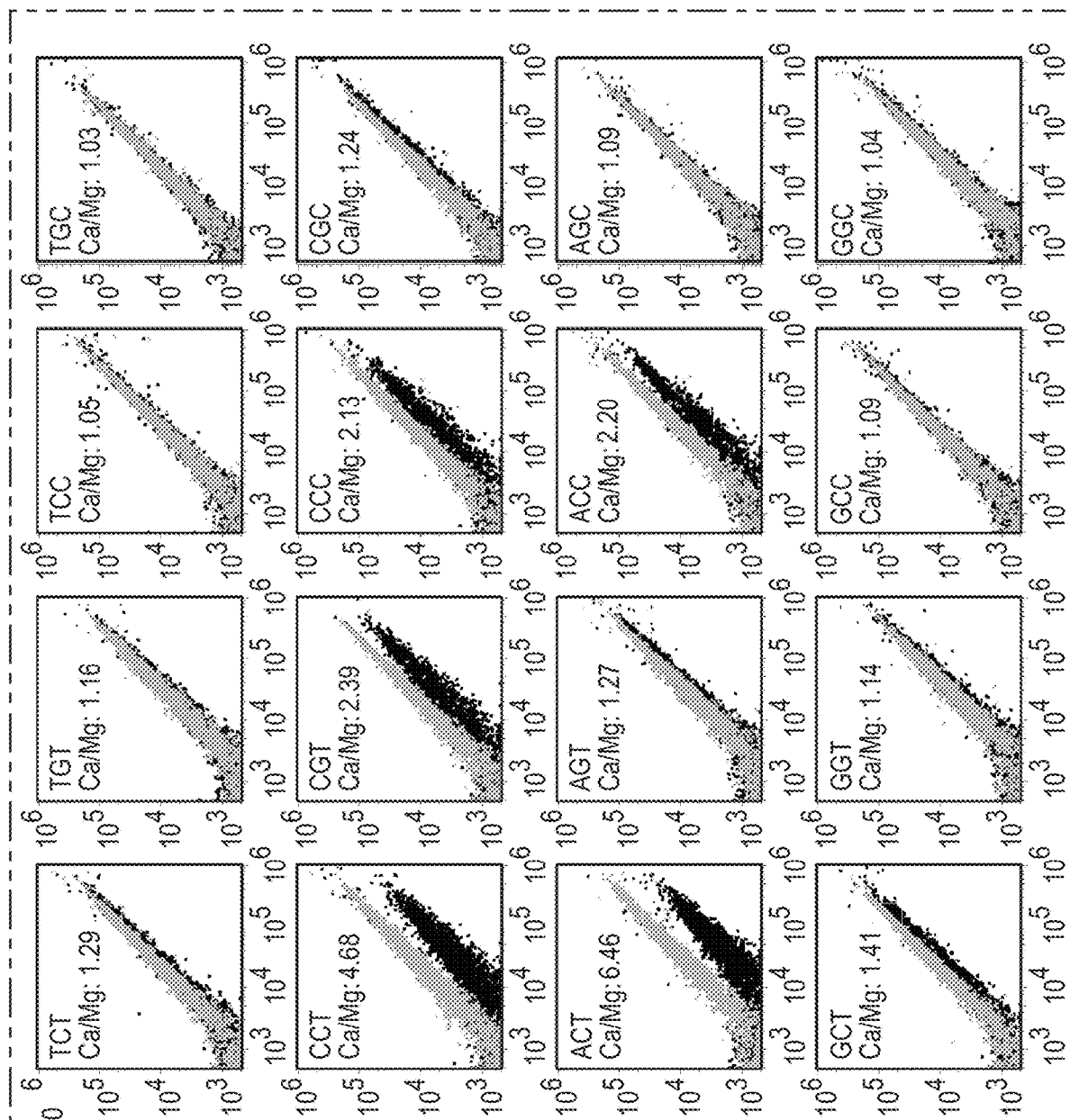
Figure 3D:
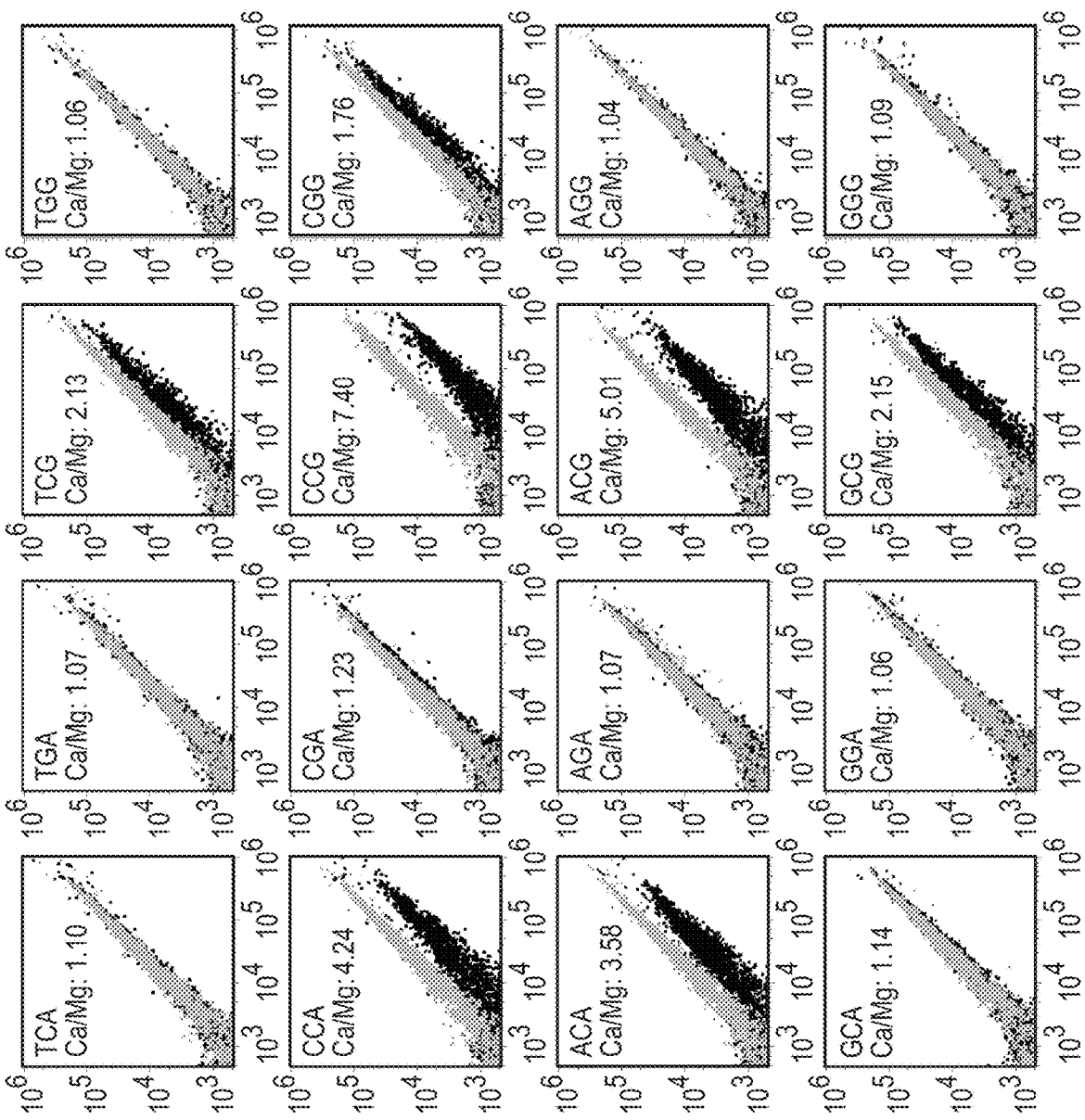
Figure 3E:
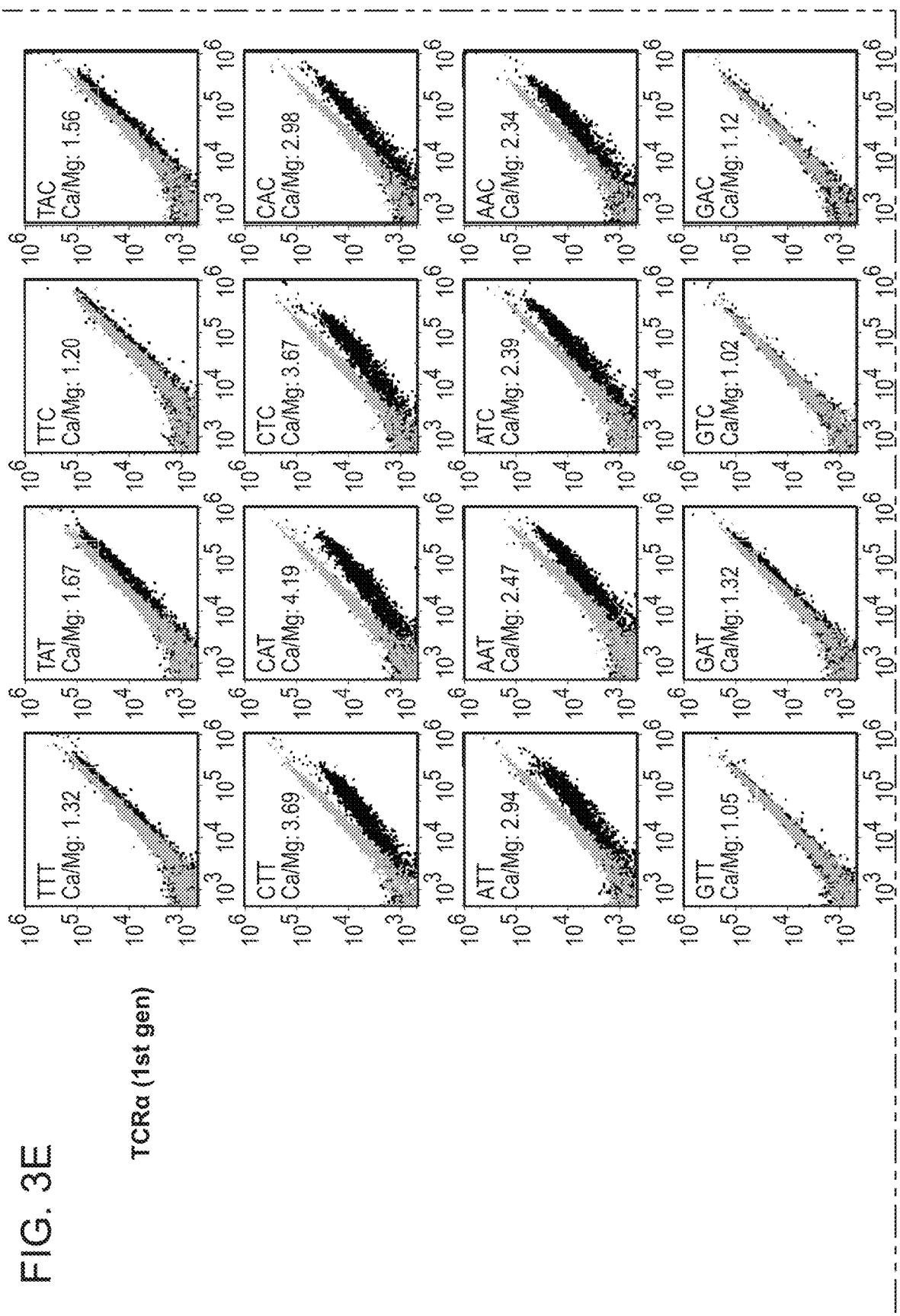
Figure 3F:
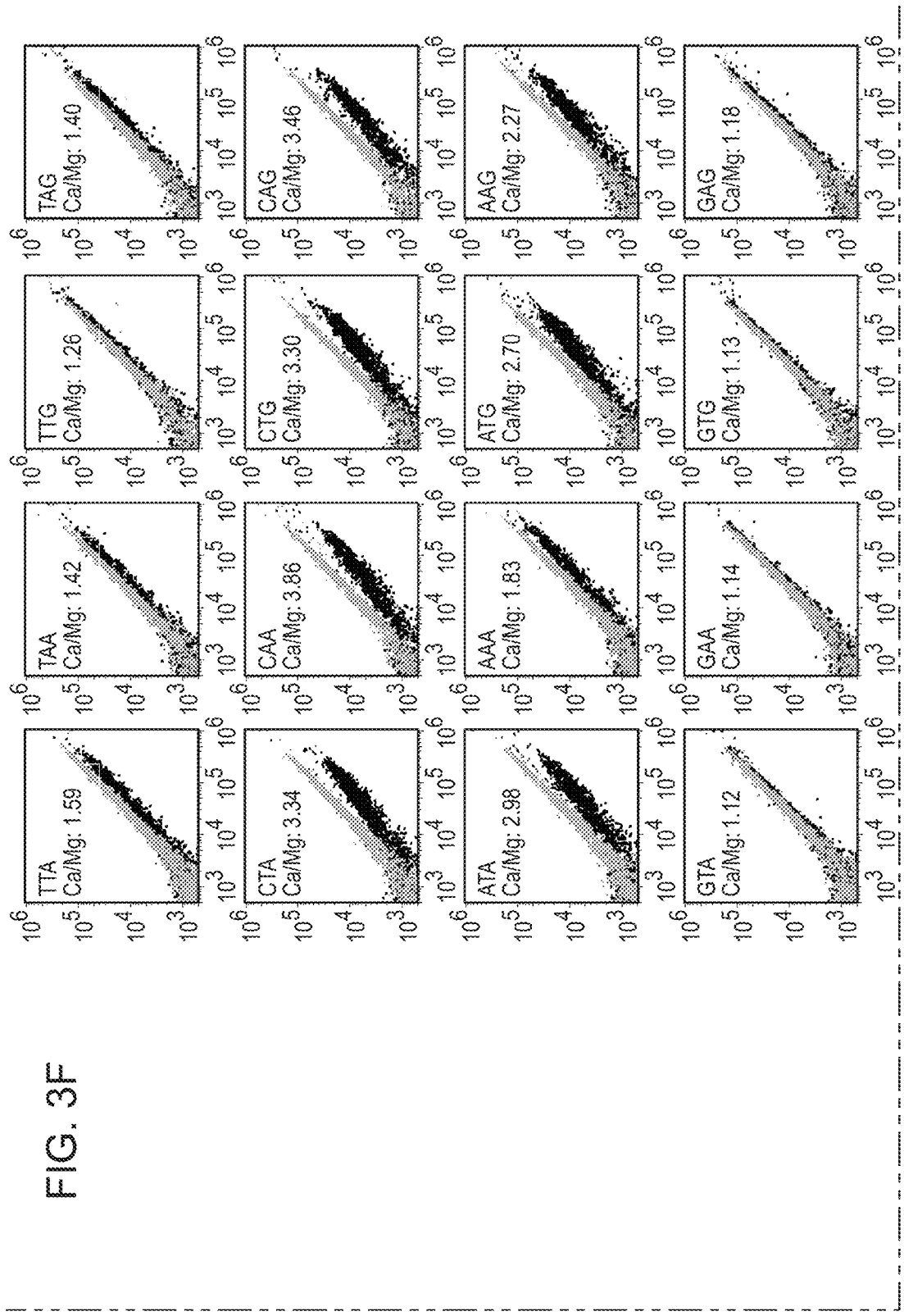
Figure 3G:
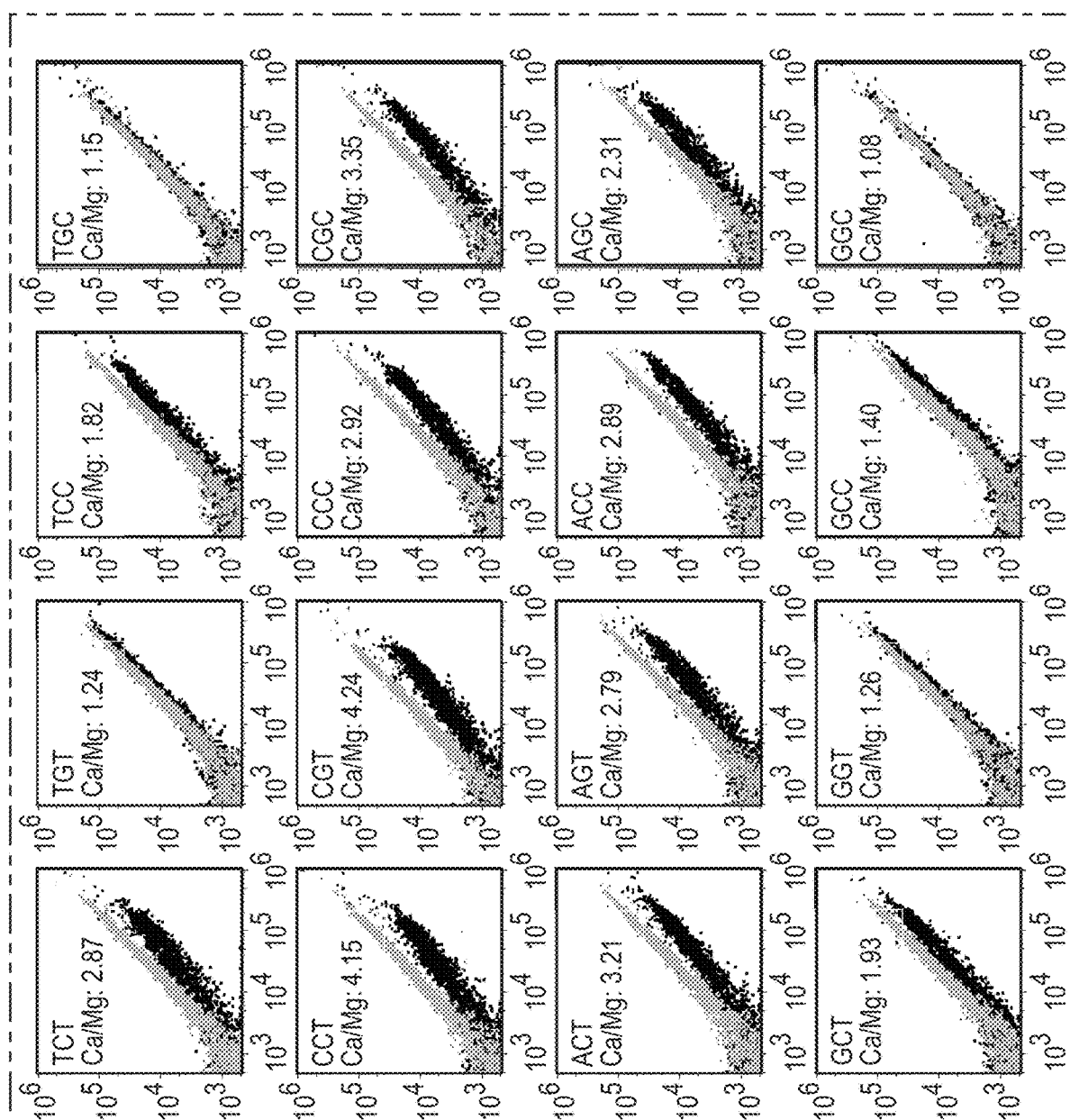
Figure 3H:
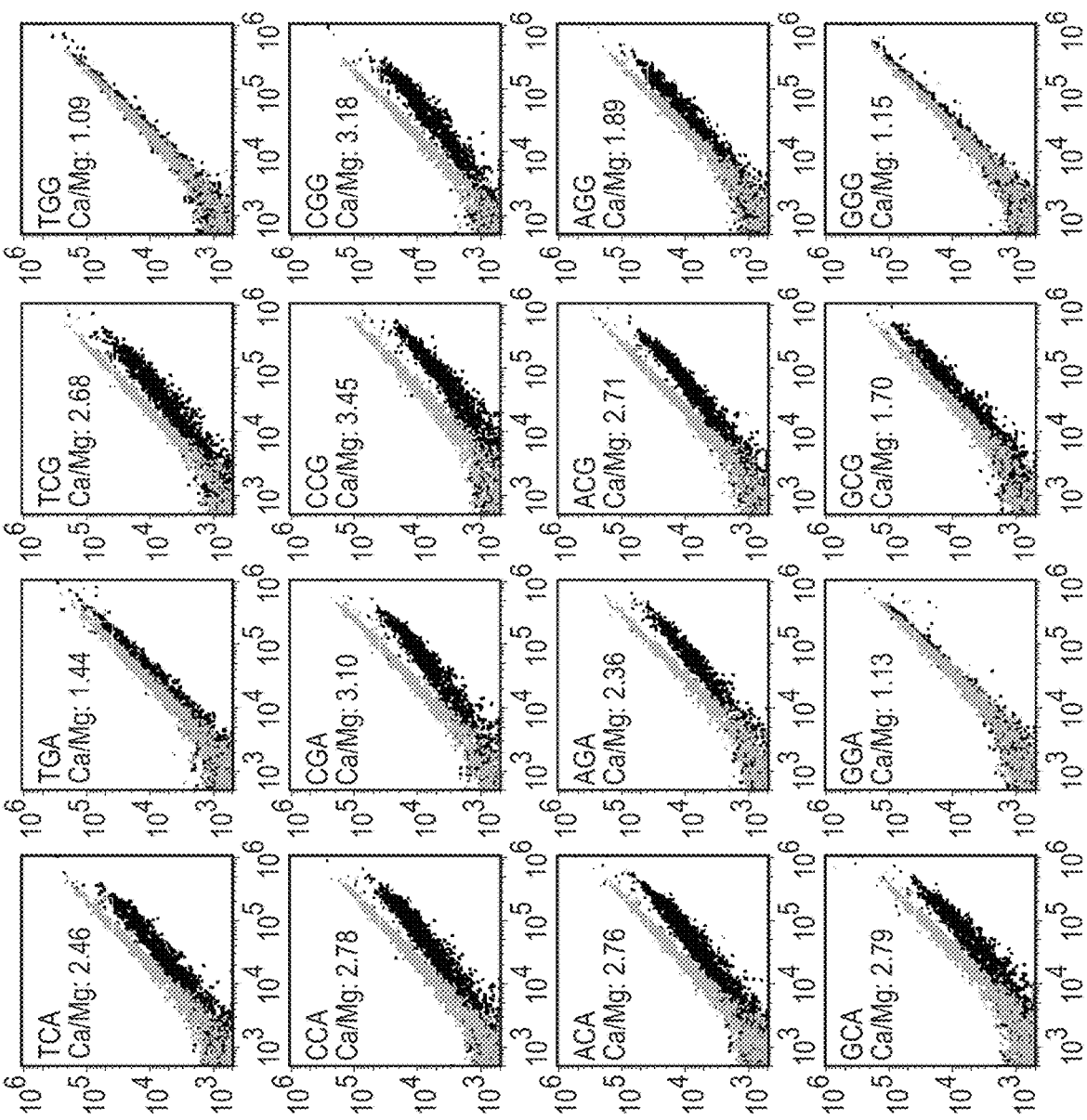
Figure 3I:
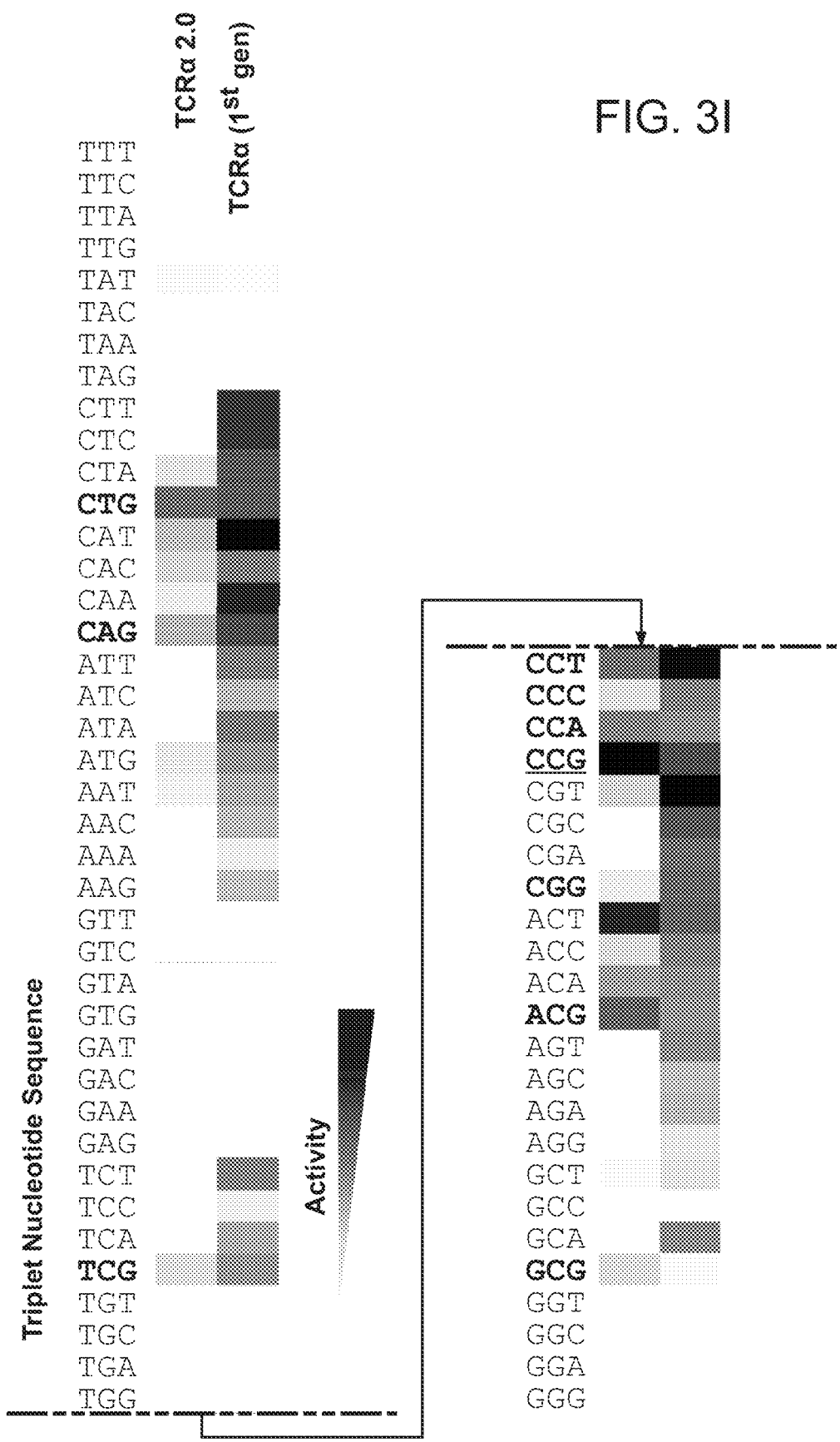

SEQ ID NO: 1 is an amino acid sequence of a wild type I-OnuI LAGLIDADG homing endonuclease (LHE).

SEQ ID NO: 2 is an amino acid sequence of a wild type I-OnuI LHE.

SEQ ID NO: 3 is an amino acid sequence of a biologically active fragment of a wild-type I-OnuI LHE.

SEQ ID NO: 4 is an amino acid sequence of a biologically active fragment of a wild-type I-OnuI LHE.

SEQ ID NO: 5 is an amino acid sequence of a biologically active fragment of a wild-type I-OnuI LHE.

SEQ ID NO: 6 is an amino acid sequence of an I-OnuI LHE variant reprogrammed to bind and cleave a target site in exon 1 of the constant region of the human TCRα gene.

SEQ ID NO: 7 is an amino acid sequence of an I-OnuI LHE variant reprogrammed to bind and cleave a target site in exon 1 of the constant region of the human TCRα gene.

SEQ ID NO: 8 is an amino acid sequence of an I-OnuI LHE variant reprogrammed to bind and cleave a target site in exon 1 of the constant region of the human TCRα gene.

SEQ ID NO: 9 is an amino acid sequence of a megaTAL that binds and cleaves a target site in exon 1 of the constant region of the human TCRα gene.

SEQ ID NO: 10 is an amino acid sequence of a megaTAL that binds and cleaves a target site in exon 1 of the constant region of the human TCRα gene.

SEQ ID NO: 11 is an amino acid sequence of a megaTAL that binds and cleaves a target site in exon 1 of the constant region of the human TCRα gene.

SEQ ID NO: 12 is an amino acid sequence of a megaTAL that binds and cleaves a target site in exon 1 of the constant region of the human TCRα gene.

SEQ ID NO: 13 is an mRNA sequence that encodes a megaTAL that binds and cleaves a target site in exon 1 of the constant region of the human TCRα gene.

SEQ ID NO: 14 is an mRNA sequence that encodes a megaTAL that binds and cleaves a target site in exon 1 of the constant region of the human TCRα gene.

SEQ ID NO: 15 is an mRNA sequence that encodes a megaTAL that binds and cleaves a target site in exon 1 of the constant region of the human TCRα gene.

SEQ ID NO: 16 is an mRNA sequence that encodes a megaTAL that binds and cleaves a target site in exon 1 of the constant region of the human TCRα gene.

SEQ ID NO: 17 is an I-OnuI LHE variant target site in exon 1 of the constant region of the human TCRα gene.

SEQ ID NO: 18 is a 10.5 RVD TALE DNA binding domain target site in exon 1 of the constant region of the human TCRα gene.

SEQ ID NO: 19 is an 11.5 RVD TALE DNA binding domain target site in exon 1 of the constant region of the human TCRα gene.

SEQ ID NO: 20 is a megaTAL target site in exon 1 of the constant region of the human TCRα gene.

SEQ ID NO: 21 is off-target site in the human KAT2B gene for TCRα nucleases that target SEQ ID NO: 17.

SEQ ID NOs: 22-24 are amino acid sequences encoding NTD variant megaTALs.

SEQ ID NOs: 25-27 are mRNA sequences encoding NTD variant megaTALs.

SEQ ID NO: 28 is an amino acid sequence encoding murine Trex2.

SEQ ID NO: 29 is an mRNA sequence encoding murine Trex2.

SEQ ID NOs: 30-40 set forth the amino acid sequences of various linkers.

SEQ ID NOs: 41-65 set forth the amino acid sequences of protease cleavage sites and self-cleaving polypeptide cleavage sites.

In the foregoing sequences, X, if present, refers to any amino acid or the absence of an amino acid.

DETAILED DESCRIPTION

A. Overview

The disclosure generally relates to, in part, improved genome editing compositions and methods of use thereof. Genome edited immune effector cells offer numerous advantages compared to existing cell-based immunotherapies including, but not limited to, improved safety due to decreased risk of undesirable autoimmune response, precisely targeted therapy with more predictable therapeutic gene expression, increased durability in the tumor microenvironment and increased efficacy. Without wishing to be bound by any particular theory, genome editing compositions contemplated in various embodiments comprise homing endonucleases and megaTALs targeting the T cell receptor alpha (TCRα) gene, engineered for improved safety and increased target site specificity, selectivity and catalytic activity.

In particular embodiments, modification of one or more TCRα alleles ablates or substantially ablates expression of the TCRα allele(s), decreases expression of the TCRα allele(s), and/or impairs, substantially impairs, or ablates one or more functions of the TCRα allele(s) or renders the TCRα allele(s) non-functional. In particular embodiments, TCRα functions include, but are not limited to, recruiting CD3 to the cell surface, MHC dependent recognition and binding of antigen, activation of TCRαβ signaling.

Genome editing compositions and methods contemplated in various embodiments comprise nuclease variants, designed to bind and cleave a target site in the human T cell receptor alpha (TCRα) gene. The nuclease variants contemplated in particular embodiments, can be used to introduce a double-strand break in a target polynucleotide sequence, which may be repaired by non-homologous end joining (NHEJ) in the absence of a polynucleotide template, e.g., a donor repair template, or by homology directed repair (HDR), i.e., homologous recombination, in the presence of a donor repair template. Nuclease variants contemplated in certain embodiments, can also be designed as nickases, which generate single-stranded DNA breaks that can be repaired using the cell's base-excision-repair (BER) machinery or homologous recombination in the presence of a donor repair template. NHEJ is an error-prone process that frequently results in the formation of small insertions and deletions that disrupt gene function. Homologous recombination requires homologous DNA as a template for repair and can be leveraged to create a limitless variety of modifications specified by the introduction of donor DNA containing the desired sequence at the target site, flanked on either side by sequences bearing homology to regions flanking the target site.

In one preferred embodiment, the genome editing compositions contemplated herein comprise a homing endonuclease variant or megaTAL that targets the human TCRα gene.

In various embodiments, the TCRα gene targeting homing endonuclease variants or megaTALs contemplated herein have increased binding site selectivity or specificity to the target site compared to existing homing endonucleases or megaTALs that target the TCRα gene.

In various embodiments, the TCRα gene targeting homing endonuclease variants or megaTALs contemplated herein have improved binding site selectivity or specificity to the target site while retaining high catalytic activity compared to existing homing endonucleases or megaTALs that target the TCRα gene.

In one preferred embodiment, the genome editing compositions contemplated herein comprise a homing endonuclease variant or megaTAL and an end-processing enzyme, e.g., Trex2.

The practice of the particular embodiments will employ, unless indicated specifically to the contrary, conventional methods of chemistry, biochemistry, organic chemistry, molecular biology, microbiology, recombinant DNA techniques, genetics, immunology, and cell biology that are within the skill of the art, many of which are described below for the purpose of illustration. Such techniques are explained fully in the literature. See e.g., Sambrook, et al., *Molecular Cloning: A Laboratory Manual* (3rd Edition, 2001); Sambrook, et al., *Molecular Cloning: A Laboratory Manual* (2nd Edition, 1989); Maniatis et al., *Molecular Cloning: A Laboratory Manual* (1982); Ausubel et al., *Current Protocols in Molecular Biology* (*John Wiley and Sons*, updated July 2008); *Short Protocols in Molecular Biology: A Compendium of Methods from Current Protocols in Molecular Biology*, Greene Pub. Associates and Wiley-Interscience; Glover, *DNA Cloning: A Practical Approach*, vol. I & II (IRL Press, Oxford, 1985); Anand, Techniques for the Analysis of Complex Genomes, (Academic Press, New York, 1992); Transcription and Translation (B. Hames & S. Higgins, Eds., 1984); Perbal, *A Practical Guide to Molecular Cloning* (1984); *Harlow and Lane, Antibodies*, (Cold Spring Harbor Laboratory Press, Cold Spring Harbor, N.Y., 1998) *Current Protocols in Immunology Q*. E. Coligan, A. M. Kruisbeek, D. H. Margulies, E. M. Shevach and W. Strober, eds., 1991); *Annual Review of Immunology*; as well as monographs in journals such as Advances in Immunology.

B. Definitions

Unless defined otherwise, all technical and scientific terms used herein have the same meaning as commonly understood by those of ordinary skill in the art to which the invention belongs. Although any methods and materials similar or equivalent to those described herein can be used in the practice or testing of particular embodiments, preferred embodiments of compositions, methods and materials are described herein. For the purposes of the present disclosure, the following terms are defined below.

The articles "a," "an," and "the" are used herein to refer to one or to more than one (i.e., to at least one, or to one or more) of the grammatical object of the article. By way of example, "an element" means one element or one or more elements.

The use of the alternative (e.g., "or") should be understood to mean either one, both, or any combination thereof of the alternatives.

The term "and/or" should be understood to mean either one, or both of the alternatives.

As used herein, the term "about" or "approximately" refers to a quantity, level, value, number, frequency, percentage, dimension, size, amount, weight or length that varies by as much as 15%, 10%, 9%, 8%, 7%, 6%, 5%, 4%, 3%, 2% or 1% to a reference quantity, level, value, number, frequency, percentage, dimension, size, amount, weight or length. In one embodiment, the term "about" or "approximately" refers a range of quantity, level, value, number, frequency, percentage, dimension, size, amount, weight or length ±15%, ±10%, ±9%, ±8%, ±7%, ±6%, ±5%, ±4%, ±3%, ±2%, or ±1% about a reference quantity, level, value, number, frequency, percentage, dimension, size, amount, weight or length.

In one embodiment, a range, e.g., 1 to 5, about 1 to 5, or about 1 to about 5, refers to each numerical value encompassed by the range. For example, in one non-limiting and merely illustrative embodiment, the range "1 to 5" is equivalent to the expression 1, 2, 3, 4, 5; or 1.0, 1.5, 2.0, 2.5, 3.0, 3.5, 4.0, 4.5, or 5.0; or 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, or 5.0.

As used herein, the term "substantially" refers to a quantity, level, value, number, frequency, percentage, dimension, size, amount, weight or length that is 80%, 85%, 90%, 91%, 92%, 93%, 94%, 95%, 96%, 97%, 98%, 99% or higher compared to a reference quantity, level, value, number, frequency, percentage, dimension, size, amount, weight or length. In one embodiment, "substantially the same" refers to a quantity, level, value, number, frequency, percentage, dimension, size, amount, weight or length that produces an effect, e.g., a physiological effect, that is approximately the same as a reference quantity, level, value, number, frequency, percentage, dimension, size, amount, weight or length.

Throughout this specification, unless the context requires otherwise, the words "comprise", "comprises" and "comprising" will be understood to imply the inclusion of a stated step or element or group of steps or elements but not the exclusion of any other step or element or group of steps or elements. By "consisting of" is meant including, and limited to, whatever follows the phrase "consisting of" Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that no other elements are present that materially affect the activity or action of the listed elements.

Reference throughout this specification to "one embodiment," "an embodiment," "a particular embodiment," "a related embodiment," "a certain embodiment," "an additional embodiment," or "a further embodiment" or combinations thereof means that a particular feature, structure or characteristic described in connection with the embodiment is included in at least one embodiment. Thus, the appearances of the foregoing phrases in various places throughout this specification are not necessarily all referring to the same embodiment. Furthermore, the particular features, structures, or characteristics may be combined in any suitable manner in one or more embodiments. It is also understood that the positive recitation of a feature in one embodiment, serves as a basis for excluding the feature in a particular embodiment.

The term "ex vivo" refers generally to activities that take place outside an organism, such as experimentation or measurements done in or on living tissue in an artificial environment outside the organism, preferably with minimum alteration of the natural conditions. In particular embodiments, "ex vivo" procedures involve living cells or tissues taken from an organism and cultured or modulated in a laboratory apparatus, usually under sterile conditions, and typically for a few hours or up to about 24 hours, but including up to 48 or 72 hours, depending on the circumstances. In certain embodiments, such tissues or cells can be collected and frozen, and later thawed for ex vivo treatment. Tissue culture experiments or procedures lasting longer than a few days using living cells or tissue are typically considered to be "in vitro," though in certain embodiments, this term can be used interchangeably with ex vivo.

The term "in vivo" refers generally to activities that take place inside an organism. In one embodiment, cellular genomes are engineered, edited, or modified in vivo.

By "enhance" or "promote" or "increase" or "expand" or "potentiate" refers generally to the ability of a nuclease variant, genome editing composition, or genome edited cell contemplated herein to produce, elicit, or cause a greater response (i.e., physiological response) compared to the response caused by either vehicle or control. A measurable response may include an increase in engineered TCR or CAR expression, increase in HR or HDR efficiency, increase in binding site selectivity, increase in binding site specificity, increase in on-target binding, increases in immune effector cell expansion, activation, persistence, and/or an increase in cancer cell death killing ability, among others apparent from the understanding in the art and the description herein. An "increased" or "enhanced" amount is typically a "statistically significant" amount, and may include an increase that is 1.1, 1.2, 1.5, 2, 3, 4, 5, 6, 7, 8, 9, 10, 15, 20, 30 or more times (e.g., 500, 1000 times) (including all integers and decimal points in between and above 1, e.g., 1.5, 1.6, 1.7, 1.8, etc.) the response produced by vehicle or control.

By "decrease" or "lower" or "lessen" or "reduce" or "abate" or "ablate" or "inhibit" or "dampen" refers generally to the ability of a nuclease variant, genome editing composition, or genome edited cell contemplated herein to produce, elicit, or cause a lesser response (i.e., physiological response) compared to the response caused by either vehicle or control. A measurable response may include a decrease in endogenous TCR expression or function, a decrease in off-target binding, a decrease in expression of biomarkers associated with immune effector cell exhaustion, and the like. A "decrease" or "reduced" amount is typically a "statistically significant" amount, and may include an decrease that is 1.1, 1.2, 1.5, 2, 3, 4, 5, 6, 7, 8, 9, 10, 15, 20, 30 or more times (e.g., 500, 1000 times) (including all integers and decimal points in between and above 1, e.g., 1.5, 1.6, 1.7, 1.8, etc.) the response (reference response) produced by vehicle, or control.

By "maintain," or "preserve," or "maintenance," or "no change," or "no substantial change," or "no substantial decrease" refers generally to the ability of a nuclease variant, genome editing composition, or genome edited cell contemplated herein to produce, elicit, or cause a substantially similar or comparable physiological response (i.e., downstream effects) in as compared to the response caused by either vehicle or control. A comparable response is one that is not significantly different or measurable different from the reference response.

The terms "specific binding affinity" or "specifically binds" or "specifically bound" or "specific binding" or "specifically targets" and describe binding of one molecule to another, e.g., DNA binding domain of a polypeptide binding to DNA, at greater binding affinity than background binding. A binding domain "specifically binds" to a target site if it binds to or associates with a target site with an affinity or $K_a$ (i.e., an equilibrium association constant of a particular binding interaction with units of 1/M) of, for example, greater than or equal to about $10^5$ $M^{-1}$. In certain embodiments, a binding domain binds to a target site with a $K_a$ greater than or equal to about $10^6$ $M^{-1}$, $10^7$ $M^{-1}$, $10^8$ $M^{-1}$, $10^9$ $M^{-1}$, $10^{10}$ $M^{-1}$, $10^{11}$ $M^{-1}$, $10^{12}$ $M^{-1}$, or $10^{13}$ $M^{-1}$ "High affinity" binding domains refers to those binding domains with a $K_a$ of at least $10^7 M^{-1}$, at least $10^8$ $M^{-1}$, at least $10^9 M^{-1}$, at least $10^{10}$ $M^{-1}$, at least $10^{11}$ $M^{-1}$, at least $10^{12} M^{-1}$, at least $10^{13}$ $M^{-1}$, or greater.

Alternatively, affinity may be defined as an equilibrium dissociation constant ($K_d$) of a particular binding interaction with units of M (e.g., $10^{-5}$ M to $10^{-13}$ M, or less). Affinities of nuclease variants comprising one or more DNA binding domains for DNA target sites contemplated in particular embodiments can be readily determined using conventional techniques, e.g., yeast cell surface display, or by binding association, or displacement assays using labeled ligands.

In one embodiment, the affinity of specific binding is about 2 times greater than background binding, about 5 times greater than background binding, about 10 times greater than background binding, about 20 times greater than background binding, about 50 times greater than background binding, about 100 times greater than background binding, or about 1000 times greater than background binding or more.

The terms "selectively binds" or "selectively bound" or "selectively binding" or "selectively targets" and describe preferential binding of one molecule to a target molecule (on-target binding) in the presence of a plurality of off-target molecules. In particular embodiments, an HE or megaTAL selectively binds an on-target DNA binding site about 5, 10, 15, 20, 25, 50, 100, or 1000 times more frequently than the HE or megaTAL binds an off-target DNA target binding site.

"On-target" refers to a target site sequence.

"Off-target" refers to a sequence similar to but not identical to a target site sequence.

A "target site" or "target sequence" is a chromosomal or extrachromosomal nucleic acid sequence that defines a portion of a nucleic acid to which a binding molecule will bind and/or cleave, provided sufficient conditions for binding and/or cleavage exist. When referring to a polynucleotide sequence or SEQ ID NO. that references only one strand of a target site or target sequence, it would be understood that the target site or target sequence bound and/or cleaved by a nuclease variant is double-stranded and comprises the reference sequence and its complement. In a preferred embodiment, the target site is a sequence in a human TCRα gene.

A "gene," refers to a DNA region encoding a gene product, as well as all DNA regions which regulate the production of the gene product, whether or not such regulatory sequences are adjacent to coding and/or transcribed sequences. A gene includes, but is not limited to, promoter sequences, enhancers, silencers, insulators, boundary elements, terminators, polyadenylation sequences, post-transcription response elements, translational regulatory sequences such as ribosome binding sites and internal ribosome entry sites, replication origins, matrix attachment sites, and locus control regions.

As used herein, the term "genetically engineered" or "genetically modified" refers to the chromosomal or extra-chromosomal addition of extra genetic material in the form of DNA or RNA to the total genetic material in a cell. Genetic modifications may be targeted or non-targeted to a particular site in a cell's genome. In one embodiment, genetic modification is site specific. In one embodiment, genetic modification is not site specific.

As used herein, the term "genome editing" refers to the substitution, deletion, and/or introduction of genetic material at a target site in the cell's genome, which restores, corrects, disrupts, and/or modifies expression of a gene or gene product. Genome editing contemplated in particular embodiments comprises introducing one or more nuclease variants into a cell to generate DNA lesions at or proximal to a target site in the cell's genome, optionally in the presence of a donor repair template.

As used herein, the term "amount" refers to "an amount effective" or "an effective amount" of a nuclease variant, genome editing composition, or genome edited cell sufficient to achieve a beneficial or desired prophylactic or therapeutic result, including clinical results.

A "prophylactically effective amount" refers to an amount of a nuclease variant, genome editing composition, or genome edited cell sufficient to achieve the desired prophylactic result. Typically but not necessarily, since a prophylactic dose is used in subjects prior to or at an earlier stage of disease, the prophylactically effective amount is less than the therapeutically effective amount.

A "therapeutically effective amount" of a nuclease variant, genome editing composition, or genome edited cell may vary according to factors such as the disease state, age, sex, and weight of the individual, and the ability to elicit a desired response in the individual. A therapeutically effective amount is also one in which any toxic or detrimental effects are outweighed by the therapeutically beneficial effects. The term "therapeutically effective amount" includes an amount that is effective to "treat" a subject (e.g., a patient). When a therapeutic amount is indicated, the precise amount of the compositions contemplated in particular embodiments, to be administered, can be determined by a physician in view of the specification and with consideration of individual differences in age, weight, tumor size, extent of infection or metastasis, and condition of the patient (subject).

C. Nuclease Variants

Nuclease variants contemplated in particular embodiments herein are suitable for genome editing a target site in the TCRα gene and comprise one or more DNA binding domains and one or more DNA cleavage domains (e.g., one or more endonuclease and/or exonuclease domains), and optionally, one or more linkers contemplated herein. The terms "reprogrammed nuclease," "engineered nuclease," or "nuclease variant" are used interchangeably and refer to a nuclease comprising one or more DNA binding domains and one or more DNA cleavage domains, wherein the nuclease has been designed and/or modified from a parental or naturally occurring nuclease, to bind and cleave a double-stranded DNA target sequence in exon 1 of the constant region of the human TCRα gene.

In particular embodiments, a nuclease variant binds and cleaves a target sequence in exon 1 of the constant region of the human TCRα gene, preferably at SEQ ID NO: 17 in exon 1 of the constant region of the human TCRα gene, and more preferably at the sequence "ATTC" in SEQ ID NO: 17 in exon 1 of the constant region of the human TCRα gene.

The nuclease variant may be designed and/or modified from a naturally occurring nuclease or from a previous nuclease variant. Nuclease variants contemplated in particular embodiments may further comprise one or more additional functional domains, e.g., an end-processing enzymatic domain of an end-processing enzyme that exhibits 5'-3' exonuclease, 5'-3' alkaline exonuclease, 3'-5'exonuclease (e.g., Trex2), 5' flap endonuclease, helicase, template-dependent DNA polymerases or template-independent DNA polymerase activity.

Illustrative examples of nuclease variants that bind and cleave a target sequence in the TCRα gene include, but are not limited to homing endonuclease (meganuclease) variants and megaTALs.

1. Homing Endonuclease (Meganuclease) Variants

In various embodiments, a homing endonuclease or meganuclease is reprogrammed to introduce a double-strand break (DSB) in a target site in a TCRα gene. In particular embodiments, a homing endonuclease variant introduces a double strand break in exon 1 of the constant region of the human TCRα gene, preferably at SEQ ID NO: 17 in exon 1 of the constant region of the human TCRα gene, and more preferably at the sequence "ATTC" in SEQ ID NO: 17 in exon 1 of the constant region of the human TCRα gene. "Homing endonuclease" and "meganuclease" are used interchangeably and refer to naturally-occurring homing endonucleases that recognize 12-45 base-pair cleavage sites and are commonly grouped into five families based on sequence and structure motifs: LAGLIDADG, GIY-YIG, HNH, His-Cys box, and PD-(D/E)XK.

A "reference homing endonuclease" or "reference meganuclease" refers to a wild type homing endonuclease or a homing endonuclease found in nature. In one embodiment, a "reference homing endonuclease" refers to a wild type homing endonuclease that has been modified to increase basal activity.

An "engineered homing endonuclease," "reprogrammed homing endonuclease," "homing endonuclease variant," "engineered meganuclease," "reprogrammed meganuclease," or "meganuclease variant" refers to a homing endonuclease comprising one or more DNA binding domains and one or more DNA cleavage domains, wherein the homing endonuclease has been designed and/or modified from a parental or naturally occurring homing endonuclease, to bind and cleave a DNA target sequence in a TCRα gene. The homing endonuclease variant may be designed and/or modified from a naturally occurring homing endonuclease or from another homing endonuclease variant. Homing endonuclease variants contemplated in particular embodiments may further comprise one or more additional functional domains, e.g., an end-processing enzymatic domain of an end-processing enzyme that exhibits 5'-3' exonuclease, 5'-3' alkaline exonuclease, 3'-5' exonuclease (e.g., Trex2), 5' flap endonuclease, helicase, template dependent DNA polymerase or template-independent DNA polymerase activity.

In particular embodiments, the homing endonuclease variants contemplate herein comprise increased selectivity to a target site compared to existing homing endonucleases, e.g., SEQ ID NO: 6. In particular embodiments, the homing endonucleases contemplated herein comprise increased selectivity to a target site while retaining catalytic activity compared to existing homing endonucleases, e.g., SEQ ID NO: 6.

Homing endonuclease (HE) variants do not exist in nature and can be obtained by recombinant DNA technology or by random mutagenesis. HE variants may be obtained by making one or more amino acid alterations, e.g., mutating, substituting, adding, or deleting one or more amino acids, in a naturally occurring HE or HE variant. In particular embodiments, a HE variant comprises one or more amino acid alterations to the DNA recognition interface.

HE variants contemplated in particular embodiments may further comprise one or more linkers and/or additional functional domains, e.g., an end-processing enzymatic domain of an end-processing enzyme that exhibits 5'-3' exonuclease, 5'-3' alkaline exonuclease, 3'-5' exonuclease (e.g., Trex2), 5' flap endonuclease, helicase, template-dependent DNA polymerase or template-independent DNA polymerase activity. In particular embodiments, HE variants are introduced into a T cell with an end-processing enzyme that exhibits 5'-3' exonuclease, 5'-3' alkaline exonuclease, 3'-5' exonuclease (e.g., Trex2), 5' flap endonuclease, helicase, template-dependent DNA polymerase or template-independent DNA polymerase activity. The HE variant and 3' processing enzyme may be introduced separately, e.g., in different vectors or separate mRNAs, or together, e.g., as a fusion protein, or in a polycistronic construct separated by a viral self-cleaving peptide or an IRES element.

A "DNA recognition interface" refers to the HE amino acid residues that interact with nucleic acid target bases as well as those residues that are adjacent. For each HE, the DNA recognition interface comprises an extensive network of side chain-to-side chain and side chain-to-DNA contacts, most of which is necessarily unique to recognize a particular nucleic acid target sequence. Thus, the amino acid sequence of the DNA recognition interface corresponding to a particular nucleic acid sequence varies significantly and is a feature of any natural or HE variant. By way of non-limiting example, a HE variant contemplated in particular embodiments may be derived by constructing libraries of HE variants in which one or more amino acid residues localized in the DNA recognition interface of the natural HE (or a previously generated HE variant) are varied. The libraries may be screened for target cleavage activity against each predicted TCRα target site using cleavage assays (see e.g., Jarjour et al., 2009. Nuc. Acids Res. 37(20): 6871-6880).

LAGLIDADG homing endonucleases (LHE) are the most well studied family of homing endonucleases, are primarily encoded in archaea and in organellar DNA in green algae and fungi, and display the highest overall DNA recognition specificity. LHEs comprise one or two LAGLIDADG catalytic motifs per protein chain and function as homodimers or single chain monomers, respectively. Structural studies of LAGLIDADG proteins identified a highly conserved core structure (Stoddard 2005), characterized by an αββαββα fold, with the LAGLIDADG motif belonging to the first helix of this fold. The highly efficient and specific cleavage of LHE's represent a protein scaffold to derive novel, highly specific and selective endonucleases. However, engineering LHEs to bind and cleave a non-natural or non-canonical target site requires selection of the appropriate LHE scaffold, examination of the target locus, selection of putative target sites, and extensive alteration of the LHE to alter its DNA contact points and cleavage specificity, at up to two-thirds of the base-pair positions in a target site.

Illustrative examples of LHEs include, but are not limited to I-AabMI, I-AaeMI, I-AniI, I-ApaMI, I-CapIII, I-CapIV, I-CkaMI, I-CpaMI, I-CpaMII, I-CpaMIV, I-CpaMV, I-CpaV, I-CraMI, I-EjeMI, I-GpeMI, I-GpiI, I-GzeMI, I-GzeMII, I-HjeMI, I-LtrII, I-LtrI, I-LtrWI, I-MpeMI, I-MveMI, I-NcrII, I-NcrI, I-NcrMI, I-OheMI, I-OnuI, I-OsoMI, I-OsoMII, I-OsoMIII, I-OsoMIV, I-PanMI, I-PanMII, I-PanMIII, I-PnoMI, I-ScuMI, I-SmaMI, I-SscMI, and I-Vdi141I.

In one embodiment, the reprogrammed LHE or LHE variant is an I-OnuI variant. See e.g., SEQ ID NOs: 7-8.

In one embodiment, reprogrammed I-OnuI LHEs or I-OnuI variants targeting the TCRα gene were generated from a natural I-OnuI or biologically active fragment thereof (SEQ ID NOs: 1-5). In a preferred embodiment, reprogrammed I-OnuI LHEs or I-OnuI variants targeting the human TCRα gene were generated from an existing I-OnuI variant.

In one embodiment, the I-OnuI LHE that binds and cleaves a human TCRα gene comprises at least 99% sequence identity with the DNA recognition interface of an I-OnuI LHE variant as set forth in SEQ ID NO: 7 or SEQ ID NO: 8, and biologically active fragments thereof.

In a particular embodiment, an I-OnuI LHE variant that binds and cleaves a human TCRα gene comprises one or more amino acid substitutions or modifications in the DNA recognition interface of an I-OnuI as set forth in SEQ ID NO: 7 or SEQ ID NO: 8, biologically active fragments thereof, and/or further variants thereof.

In certain embodiments, the HE variant cleaves a TCRα exon 1 constant region target site and comprises following amino acid substitutions: L26I, R28D, N32R, K34N, S35E, V37N, G38R, S40R, E42S, G44R, V68K, A70T, G73S, N75R, S78M, K80R, L138M, T143N, S159P, S176A, C180H, F182G, I186K, S188V, S190G, K191T, L192A, G193K, Q195Y, Q197G, V199R, S201A, T203S, K207R, Y223S, K225R, S233R, D236E, and V238E of any one of SEQ ID NOs: 1-5, or a biologically active fragment thereof.

In certain embodiments, the HE variant cleaves a TCRα exon 1 constant region target site and comprises following amino acid substitutions: L26I, R28D, N32R, K34N, S35E, V37N, G38R, S40R, E42S, G44R, V68K, A70T, G73S, N75R, S78M, K80R, L138M, T143N, S159P, S176A, E178D, C180H, F182G, I186K, S188V, S190G, K191T, L192A, G193K, Q195Y, Q197G, V199R, S201A, T203S, K207R, Y223S, K225R, S233R, D236E, and V238E of any one of SEQ ID NOs: 1-5, or a biologically active fragment thereof.

In particular embodiments, an I-OnuI LHE variant that binds and cleaves a human TCRα gene comprises an amino acid sequence that is at least 99% identical to the amino acid sequence set forth in any one of SEQ ID NO: 7 or SEQ ID NO: 8, or a biologically active fragment thereof.

In particular embodiments, an I-OnuI LHE variant comprises an amino acid sequence set forth in any one of SEQ ID NOs: 7-8, or a biologically active fragment thereof.

In particular embodiments, an I-OnuI LHE variant comprises an amino acid sequence set forth in SEQ ID NO: 7, or a biologically active fragment thereof.

In particular embodiments, an I-OnuI LHE variant comprises an amino acid sequence set forth in SEQ ID NO: 8, or a biologically active fragment thereof.

2. MegaTALs

In various embodiments, a megaTAL comprising a homing endonuclease variant is reprogrammed to introduce a double-strand break (DSB) in a target site in exon1 of the constant region of the human TCRα gene. In particular embodiments, a megaTAL introduces a DSB in in exon 1 of the constant region of the human TCRα gene, preferably at SEQ ID NO: 17 in exon 1 of the constant region of the human TCRα gene, and more preferably at the sequence "ATTC" in SEQ ID NO: 17 in exon 1 of the constant region of the human TCRα gene. A "megaTAL" refers to a polypeptide comprising a TALE DNA binding domain and a homing endonuclease variant that binds and cleaves a DNA target sequence in a TCRα gene, and optionally comprises one or more linkers and/or additional functional domains, e.g., an end-processing enzymatic domain of an end-processing enzyme that exhibits 5'-3' exonuclease, 5'-3' alkaline exonuclease, 3'-5' exonuclease (e.g., Trex2), 5' flap endonuclease, helicase or template-independent DNA polymerase activity.

In particular embodiments, a megaTAL can be introduced into a cell along with an end-processing enzyme that exhibits 5'-3' exonuclease, 5'-3' alkaline exonuclease, 3'-5' exonuclease (e.g., Trex2), 5' flap endonuclease, helicase, template-dependent DNA polymerase, or template-independent DNA polymerase activity. The megaTAL and 3' processing enzyme may be introduced separately, e.g., in different vectors or separate mRNAs, or together, e.g., as a fusion protein, or in a polycistronic construct separated by a viral self-cleaving peptide or an IRES element.

A "TALE DNA binding domain" is the DNA binding portion of transcription activator-like effectors (TALE or TAL-effectors), which mimics plant transcriptional activators to manipulate the plant transcriptome (see e.g., Kay et al., 2007. Science 318:648-651). TALE DNA binding domains contemplated in particular embodiments are engineered de novo or from naturally occurring TALEs, e.g., AvrBs3 from *Xanthomonas campestris* pv. vesicatoria, *Xanthomonas gardneri*, *Xanthomonas translucens*, *Xanthomonas axonopodis*, *Xanthomonas perforans*, *Xanthomonas alfalfa*, *Xanthomonas citri*, *Xanthomonas euvesicatoria*, and *Xanthomonas oryzae* and brg11 and hpx17 from *Ralstonia solanacearum*. Illustrative examples of TALE proteins for deriving and designing DNA binding domains are disclosed in U.S. Pat. No. 9,017,967, and references cited therein, all of which are incorporated herein by reference in their entireties.

In particular embodiments, a megaTAL comprises a TALE DNA binding domain comprising one or more repeat units that are involved in binding of the TALE DNA binding domain to its corresponding target DNA sequence. A single "repeat unit" (also referred to as a "repeat") is typically 33-35 amino acids in length. Each TALE DNA binding domain repeat unit includes 1 or 2 DNA-binding residues making up the Repeat Variable Di-Residue (RVD), typically at positions 12 and/or 13 of the repeat. The natural (canonical) code for DNA recognition of these TALE DNA binding domains has been determined such that an HD sequence at positions 12 and 13 leads to a binding to cytosine (C), NG binds to T, NI to A, NN binds to G or A, and NG binds to T. In certain embodiments, non-canonical (atypical) RVDs are contemplated.

Illustrative examples of non-canonical RVDs suitable for use in particular megaTALs contemplated in particular embodiments include, but are not limited to HH, KH, NH, NK, NQ, RH, RN, SS, NN, SN, KN for recognition of guanine (G); NI, KI, RI, HI, SI for recognition of adenine (A); NG, HG, KG, RG for recognition of thymine (T); RD, SD, HD, ND, KD, YG for recognition of cytosine (C); NV, HN for recognition of A or G; and H*, HA, KA, N*, NA, NC, NS, RA, S*for recognition of A or T or G or C, wherein (*) means that the amino acid at position 13 is absent.

Additional illustrative examples of RVDs suitable for use in particular megaTALs contemplated in particular embodiments further include those disclosed in U.S. Pat. No. 8,614,092, which is incorporated herein by reference in its entirety.

In particular embodiments, a megaTAL contemplated herein comprises a TALE DNA binding domain comprising 3 to 30 repeat units. In certain embodiments, a megaTAL comprises 3, 4, 5, 6, 7, 8, 9, 10, 11, 12, 13, 14, 15, 16, 17, 18, 19, 20, 21, 22, 23, 24, 25, 26, 27, 28, 29, or 30 TALE DNA binding domain repeat units. In a preferred embodiment, a megaTAL contemplated herein comprises a TALE DNA binding domain comprising 5-15 repeat units, more preferably 7-15 repeat units, more preferably 9-15 repeat units, and more preferably 9, 10, 11, 12, 13, 14, or 15 repeat units.

In particular embodiments, a megaTAL contemplated herein comprises a TALE DNA binding domain comprising 3 to 30 repeat units and an additional single truncated TALE repeat unit comprising 20 amino acids located at the C-terminus of a set of TALE repeat units, i.e., an additional C-terminal half-TALE DNA binding domain repeat unit (amino acids −20 to −1 of the C-cap disclosed elsewhere herein, infra). Thus, in particular embodiments, a megaTAL contemplated herein comprises a TALE DNA binding domain comprising 3.5 to 30.5 repeat units. In certain embodiments, a megaTAL comprises 3.5, 4.5, 5.5, 6.5, 7.5, 8.5, 9.5, 10.5, 11.5, 12.5, 13.5, 14.5, 15.5, 16.5, 17.5, 18.5, 19.5, 20.5, 21.5, 22.5, 23.5, 24.5, 25.5, 26.5, 27.5, 28.5, 29.5, or 30.5 TALE DNA binding domain repeat units. In a preferred embodiment, a megaTAL contemplated herein comprises a TALE DNA binding domain comprising 5.5-15.5 repeat units, more preferably 7.5-15.5 repeat units, more preferably 9.5-15.5 repeat units, and more preferably 9.5, 10.5, 11.5, 12.5, 13.5, 14.5, or 15.5 repeat units.

In particular embodiments, a megaTAL comprises a TAL effector architecture comprising an "N-terminal domain (NTD)" polypeptide, one or more TALE repeat domains/units, a "C-terminal domain (CTD)" polypeptide, and a homing endonuclease variant. In some embodiments, the NTD, TALE repeats, and/or CTD domains are from the same species. In other embodiments, one or more of the NTD, TALE repeats, and/or CTD domains are from different species.

As used herein, the term "N-terminal domain (NTD)" polypeptide refers to the sequence that flanks the N-terminal portion or fragment of a naturally occurring TALE DNA binding domain. The NTD sequence, if present, may be of any length as long as the TALE DNA binding domain repeat units retain the ability to bind DNA. In particular embodiments, the NTD polypeptide comprises at least 120 to at least 140 or more amino acids N-terminal to the TALE DNA binding domain (0 is amino acid 1 of the most N-terminal repeat unit). In particular embodiments, the NTD polypeptide comprises at least about 120, 121, 122, 123, 124, 125, 126, 127, 128, 129, 130, 131, 132, 133, 134, 135, 136, 137, 138, 139, or at least 140 amino acids N-terminal to the TALE DNA binding domain. In one embodiment, a megaTAL contemplated herein comprises an NTD polypeptide of at least about amino acids+1 to +122 to at least about +1 to +137 of a *Xanthomonas* TALE protein (0 is amino acid 1 of the most N-terminal repeat unit). In particular embodiments, the NTD polypeptide comprises at least about 122, 123, 124, 125, 126, 127, 128, 129, 130, 131, 132, 133, 134, 135, 136, or 137 amino acids N-terminal to the TALE DNA binding domain of a *Xanthomonas* TALE protein. In one embodiment, a megaTAL contemplated herein comprises an NTD polypeptide of at least amino acids+1 to +121 of a *Ralstonia* TALE protein (0 is amino acid 1 of the most N-terminal repeat unit). In particular embodiments, the NTD polypeptide comprises at least about 121, 122, 123, 124, 125, 126, 127, 128, 129, 130, 131, 132, 133, 134, 135, 136, or 137 amino acids N-terminal to the TALE DNA binding domain of a *Ralstonia* TALE protein.

As used herein, the term "C-terminal domain (CTD)" polypeptide refers to the sequence that flanks the C-terminal portion or fragment of a naturally occurring TALE DNA binding domain. The CTD sequence, if present, may be of any length as long as the TALE DNA binding domain repeat units retain the ability to bind DNA. In particular embodiments, the CTD polypeptide comprises at least 20 to at least 85 or more amino acids C-terminal to the last full repeat of the TALE DNA binding domain (the first 20 amino acids are the half-repeat unit C-terminal to the last C-terminal full repeat unit). In particular embodiments, the CTD polypeptide comprises at least about 20, 21, 22, 23, 24, 25, 26, 27, 28, 29, 30, 31, 32, 33, 34, 35, 36, 37, 38, 39, 40, 41, 42, 443, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, or at least 85 amino acids C-terminal to the last full repeat of the TALE DNA binding domain. In one embodiment, a megaTAL contemplated herein comprises a CTD polypeptide of at least about amino acids −20 to −1 of a *Xanthomonas* TALE protein (−20 is amino acid 1 of a half-repeat unit C-terminal to the last C-terminal full repeat unit). In particular embodiments, the CTD polypeptide comprises at least about 20, 19, 18, 17, 16, 15, 14, 13, 12, 11, 10, 9, 8, 7, 6, 5, 4, 3, 2, or 1 amino acids C-terminal to the last full repeat of the TALE DNA binding domain of a *Xanthomonas* TALE protein. In one embodiment, a megaTAL contemplated herein comprises a CTD polypeptide of at least about amino acids −20 to −1 of a *Ralstonia* TALE protein (−20 is amino acid 1 of a half-repeat unit C-terminal to the last C-terminal full repeat unit). In particular embodiments, the CTD polypeptide comprises at least about 20, 19, 18, 17, 16, 15, 14, 13, 12, 11, 10, 9, 8, 7, 6, 5, 4, 3, 2, or 1 amino acids C-terminal to the last full repeat of the TALE DNA binding domain of a *Ralstonia* TALE protein.

In particular embodiments, a megaTAL contemplated herein, comprises a fusion polypeptide comprising a TALE DNA binding domain engineered to bind a target sequence, a homing endonuclease reprogrammed to bind and cleave a target sequence, and optionally an NTD and/or CTD polypeptide, optionally joined to each other with one or more linker polypeptides contemplated elsewhere herein. Without wishing to be bound by any particular theory, it is contemplated that a megaTAL comprising TALE DNA binding domain, and optionally an NTD and/or CTD polypeptide is fused to a linker polypeptide which is further fused to a homing endonuclease variant. Thus, the TALE DNA binding domain binds a DNA target sequence that is within about 1, 2, 3, 4, 5, 6, 7, 8, 9, 10, 11, 12, 13, 14, or 15 nucleotides away from the target sequence bound by the DNA binding domain of the homing endonuclease variant. In this way, the megaTALs contemplated herein, increase the specificity, selectivity, and efficiency of genome editing.

In one embodiment, a megaTAL comprises a homing endonuclease variant and a TALE DNA binding domain that binds a nucleotide sequence that is within about 4, 5, or 6 nucleotides, preferably, 5 or 6 nucleotides upstream of the binding site of the reprogrammed homing endonuclease.

In one embodiment, a megaTAL comprises a homing endonuclease variant and a TALE DNA binding domain that binds the nucleotide sequence set forth in SEQ ID NO: 18, which is 6 nucleotides upstream of the nucleotide sequence bound and cleaved by the homing endonuclease variant (SEQ ID NO: 17). In preferred embodiments, the megaTAL target sequence is SEQ ID NO: 18.

In one embodiment, a megaTAL comprises a homing endonuclease variant and a TALE DNA binding domain that binds the nucleotide sequence set forth in SEQ ID NO: 19, which is 5 nucleotides upstream of the nucleotide sequence bound and cleaved by the homing endonuclease variant (SEQ ID NO: 17). In preferred embodiments, the megaTAL target sequence is SEQ ID NO: 19.

In particular embodiments, a megaTAL contemplated herein, comprises an NTD of about 122 amino acids to 137 amino acids, about 9.5, about 10.5, about 11.5, about 12.5, about 13.5, about 14.5, or about 15.5 binding repeat units, a CTD of about 20 amino acids to about 85 amino acids, and an I-OnuI LHE variant. In particular embodiments, any one of, two of, or all of the NTD, DNA binding domain, and CTD can be designed from the same species or different species, in any suitable combination.

In particular embodiments, a megaTAL contemplated herein, comprises the amino acid sequence set forth in any one of SEQ ID NOs: 10-12.

In particular embodiments, a megaTAL contemplated herein, comprises the amino acid sequence set forth in SEQ ID NO: 10.

In particular embodiments, a megaTAL contemplated herein, comprises the amino acid sequence set forth in SEQ ID NO: 11.

In particular embodiments, a megaTAL contemplated herein, comprises the amino acid sequence set forth in SEQ ID NO: 12.

In certain embodiments, a megaTAL comprises a TALE DNA binding domain and an I-OnuI LHE variant binds and cleaves the nucleotide sequence set forth in SEQ ID NO: 17 or SEQ ID NO: 20.

3. End-Processing Enzymes

Genome editing compositions and methods contemplated in particular embodiments comprise editing cellular genomes using a nuclease variant and one or more copies of an end-processing enzyme. In particular embodiments, a single polynucleotide encodes a homing endonuclease variant and an end-processing enzyme, separated by a linker, a self-cleaving peptide sequence, e.g., 2A sequence, or by an IRES sequence. In particular embodiments, genome editing compositions comprise a polynucleotide encoding a nuclease variant and a separate polynucleotide encoding an end-processing enzyme. In particular embodiments, genome editing compositions comprise a polynucleotide encoding a homing endonuclease variant end-processing enzyme single polypeptide fusion in addition to a tandem copy of the end-processing enzyme separated by a self-cleaving peptide.

The term "end-processing enzyme" refers to an enzyme that modifies the exposed ends of a polynucleotide chain. The polynucleotide may be double-stranded DNA (dsDNA), single-stranded DNA (ssDNA), RNA, double-stranded hybrids of DNA and RNA, and synthetic DNA (for example, containing bases other than A, C, G, and T). An end-processing enzyme may modify exposed polynucleotide chain ends by adding one or more nucleotides, removing one or more nucleotides, removing or modifying a phosphate group and/or removing or modifying a hydroxyl group. An end-processing enzyme may modify ends at endonuclease cut sites or at ends generated by other chemical or mechanical means, such as shearing (for example by passing through fine-gauge needle, heating, sonicating, mini bead tumbling, and nebulizing), ionizing radiation, ultraviolet radiation, oxygen radicals, chemical hydrolysis and chemotherapy agents.

In particular embodiments, genome editing compositions and methods contemplated in particular embodiments comprise editing cellular genomes using a homing endonuclease variant or megaTAL and a DNA end-processing enzyme.

The term "DNA end-processing enzyme" refers to an enzyme that modifies the exposed ends of DNA. A DNA end-processing enzyme may modify blunt ends or staggered ends (ends with 5' or 3' overhangs). A DNA end-processing enzyme may modify single stranded or double stranded DNA. A DNA end-processing enzyme may modify ends at endonuclease cut sites or at ends generated by other chemical or mechanical means, such as shearing (for example by passing through fine-gauge needle, heating, sonicating, mini bead tumbling, and nebulizing), ionizing radiation, ultraviolet radiation, oxygen radicals, chemical hydrolysis and chemotherapy agents. DNA end-processing enzyme may modify exposed DNA ends by adding one or more nucleotides, removing one or more nucleotides, removing or modifying a phosphate group and/or removing or modifying a hydroxyl group.

Illustrative examples of DNA end-processing enzymes suitable for use in particular embodiments contemplated herein include, but are not limited to: 5'-3' exonucleases, 5'-3' alkaline exonucleases, 3'-5' exonucleases, 5' flap endonucleases, helicases, phosphatases, hydrolases and template-independent DNA polymerases.

Additional illustrative examples of DNA end-processing enzymes suitable for use in particular embodiments contemplated herein include, but are not limited to, Trex2, Trex1, Trex1 without transmembrane domain, Apollo, Artemis, DNA2, Exo1, ExoT, ExoIII, Fen1, Fan1, MreII, Rad2, Rad9, TdT (terminal deoxynucleotidyl transferase), PNKP, RecE, RecJ, RecQ, Lambda exonuclease, Sox, Vaccinia DNA polymerase, exonuclease I, exonuclease III, exonuclease VII, NDK1, NDK5, NDK7, NDK8, WRN, T7-exonuclease Gene 6, avian myeloblastosis virus integration protein (IN), Bloom, Antartic Phophatase, Alkaline Phosphatase, Poly nucleotide Kinase (PNK), ApeI, Mung Bean nuclease, Hex1, TTRAP (TDP2), Sgs1, Sae2, CUP, Pol mu, Pol lambda, MUS81, EME1, EME2, SLX1, SLX4 and UL-12.

In particular embodiments, genome editing compositions and methods for editing cellular genomes contemplated herein comprise polypeptides comprising a homing endonuclease variant or megaTAL and an exonuclease. The term "exonuclease" refers to enzymes or domains that cleave phosphodiester bonds at the end of a polynucleotide chain via a hydrolyzing reaction that breaks phosphodiester bonds at either the 3' or 5' end.

Illustrative examples of exonucleases suitable for use in particular embodiments contemplated herein include, but are not limited to: hExoI, Yeast ExoI, *E. coli* ExoI, hTREX2, mouse TREX2, rat TREX2, hTREX1, mouse TREX1, rat TREX1, and Rat TREX1.

In particular embodiments, the DNA end-processing enzyme is a 3' to 5' exonuclease, preferably Trex 1 or Trex2, more preferably Trex2, and even more preferably human or mouse Trex2.

D. Polypeptides

Various polypeptides are contemplated herein, including, but not limited to, homing endonuclease variants, mega-TALs, and fusion polypeptides. In preferred embodiments, a polypeptide comprises the amino acid sequence set forth in SEQ ID NOs: 1-12 and 22-24. "Polypeptide," "polypeptide fragment," "peptide" and "protein" are used interchangeably, unless specified to the contrary, and according to conventional meaning, i.e., as a sequence of amino acids. In one embodiment, a "polypeptide" includes fusion polypeptides and other variants. Polypeptides can be prepared using any of a variety of well-known recombinant and/or synthetic techniques. Polypeptides are not limited to a specific length, e.g., they may comprise a full length protein sequence, a fragment of a full length protein, or a fusion protein, and may include post-translational modifications of the polypeptide, for example, glycosylations, acetylations, phosphorylations and the like, as well as other modifications known in the art, both naturally occurring and non-naturally occurring.

An "isolated protein," "isolated peptide," or "isolated polypeptide" and the like, as used herein, refer to in vitro synthesis, isolation, and/or purification of a peptide or polypeptide molecule from a cellular environment, and from association with other components of the cell, i.e., it is not significantly associated with in vivo substances.

Illustrative examples of polypeptides contemplated in particular embodiments include, but are not limited to homing endonuclease variants, megaTALs, end-processing nucleases, fusion polypeptides and variants thereof.

Polypeptides include "polypeptide variants." Polypeptide variants may differ from a naturally occurring polypeptide in one or more amino acid substitutions, deletions, additions and/or insertions. Such variants may be naturally occurring or may be synthetically generated, for example, by modifying one or more amino acids of the above polypeptide sequences. For example, in particular embodiments, it may be desirable to improve the biological properties of a homing endonuclease, megaTAL or the like that binds and cleaves a target site in the human TCRα gene by introducing one or more substitutions, deletions, additions and/or insertions into the polypeptide. In particular embodiments, polypeptides include polypeptides having at least about 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% amino acid identity to any of the reference sequences contemplated herein, typically where the variant maintains at least one biological activity of the reference sequence.

Polypeptides variants include biologically active "polypeptide fragments." Illustrative examples of biologically active polypeptide fragments include DNA binding domains, nuclease domains, and the like. As used herein, the term "biologically active fragment" or "minimal biologically active fragment" refers to a polypeptide fragment that retains at least 100%, at least 90%, at least 80%, at least 70%, at least 60%, at least 50%, at least 40%, at least 30%, at least 20%, at least 10%, or at least 5% of the naturally occurring polypeptide activity. In preferred embodiments, the biological activity is binding affinity and/or cleavage activity for a target sequence. In certain embodiments, a polypeptide fragment can comprise an amino acid chain at least 5 to about 1700 amino acids long. It will be appreciated that in certain embodiments, fragments are at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 150, 200, 250, 300, 350, 400, 450, 500, 550, 600, 650, 700, 750, 800, 850, 900, 950, 1000, 1100, 1200, 1300, 1400, 1500, 1600, 1700 or more amino acids long. In particular embodiments, a polypeptide comprises a biologically active fragment of a homing endonuclease variant. In particular embodiments, the polypeptides set forth herein may comprise one or more amino acids denoted as "X." "X" if present in an amino acid SEQ ID NO, refers to any amino acid. One or more "X" residues may be present at the N- and C-terminus of an amino acid sequence set forth in particular SEQ ID NOs contemplated herein. If the "X" amino acids are not present the remaining amino acid sequence set forth in a SEQ ID NO may be considered a biologically active fragment.

In particular embodiments, a polypeptide comprises a biologically active fragment of a homing endonuclease variant, e.g., SEQ ID NOs: 6-7, or a megaTAL (SEQ ID NOs: 10-12). The biologically active fragment may comprise an N-terminal truncation and/or C-terminal truncation. In a particular embodiment, a biologically active fragment lacks or comprises a deletion of the 1, 2, 3, 4, 5, 6, 7, or 8 N-terminal amino acids of a homing endonuclease variant compared to a corresponding wild type homing endonuclease sequence, more preferably a deletion of the 4 N-terminal amino acids of a homing endonuclease variant compared to a corresponding wild type homing endonuclease sequence. In a particular embodiment, a biologically active fragment lacks or comprises a deletion of the 1, 2, 3, 4, or 5 C-terminal amino acids of a homing endonuclease variant compared to a corresponding wild type homing endonuclease sequence, more preferably a deletion of the 2 C-terminal amino acids of a homing endonuclease variant compared to a corresponding wild type homing endonuclease sequence. In a particular preferred embodiment, a biologically active fragment lacks or comprises a deletion of the 4 N-terminal amino acids and 2 C-terminal amino acids of a homing endonuclease variant compared to a corresponding wild type homing endonuclease sequence.

In a particular embodiment, an I-OnuI variant comprises a deletion of 1, 2, 3, 4, 5, 6, 7, or 8 the following N-terminal amino acids: M, A, Y, M, S, R, R, E; and/or a deletion of the following 1, 2, 3, 4, or 5 C-terminal amino acids: R, G, S, F, V.

In a particular embodiment, an I-OnuI variant comprises a deletion or substitution of 1, 2, 3, 4, 5, 6, 7, or 8 the following N-terminal amino acids: M, A, Y, M, S, R, R, E; and/or a deletion or substitution of the following 1, 2, 3, 4, or 5 C-terminal amino acids: R, G, S, F, V.

In a particular embodiment, an I-OnuI variant comprises a deletion of 1, 2, 3, 4, 5, 6, 7, or 8 the following N-terminal amino acids: M, A, Y, M, S, R, R, E; and/or a deletion of the following 1 or 2 C-terminal amino acids: F, V.

In a particular embodiment, an I-OnuI variant comprises a deletion or substitution of 1, 2, 3, 4, 5, 6, 7, or 8 the following N-terminal amino acids: M, A, Y, M, S, R, R, E; and/or a deletion or substitution of the following 1 or 2 C-terminal amino acids: F, V.

As noted above, polypeptides may be altered in various ways including amino acid substitutions, deletions, truncations, and insertions. Methods for such manipulations are generally known in the art. For example, amino acid sequence variants of a reference polypeptide can be prepared by mutations in the DNA. Methods for mutagenesis and nucleotide sequence alterations are well known in the art. See, for example, Kunkel (1985, *Proc. Natl. Acad Sci. USA.* 82: 488-492), Kunkel et al., (1987, *Methods in Enzymol,* 154: 367-382), U.S. Pat. No. 4,873,192, Watson, J. D. et al., (Molecular Biology of the Gene, Fourth Edition, Benjamin/Cummings, Menlo Park, Calif., 1987) and the references cited therein. Guidance as to appropriate amino acid substitutions that do not affect biological activity of the protein of interest may be found in the model of Dayhoff et al., (1978) *Atlas of Protein Sequence and Structure* (Natl. Biomed. Res. Found., Washington, D.C.).

In certain embodiments, a variant will contain one or more conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. Modifications may be made in the structure of the polynucleotides and polypeptides contemplated in particular embodiments, polypeptides include polypeptides having at least about and still obtain a functional molecule that encodes a variant or derivative polypeptide with desirable characteristics. When it is desired to alter the amino acid sequence of a polypeptide to create an equivalent, or even an improved, variant polypeptide, one skilled in the art, for example, can change one or more of the codons of the encoding DNA sequence, e.g., according to Table 1.

TABLE 1

Amino Acid Codons

| Amino Acids | One letter code | Three letter code | Codons | | | | | |
|---|---|---|---|---|---|---|---|---|
| Alanine | A | Ala | GCA | GCC | GCG | GCU | | |
| Cysteine | C | Cys | UGC | UGU | | | | |
| Aspartic acid | D | Asp | GAC | | | | | |
| Glutamic acid | E | Glu | GAA | GAG | | | | |
| Phenylalanine | F | Phe | UUC | UUU | | | | |
| Glycine | G | Gly | GGA | GGC | GGG | GGU | | |
| Histidine | H | His | CAC | CAU | | | | |
| Isoleucine | I | Iso | AUA | AUC | AUU | | | |
| Lysine | K | Lys | AAA | AAG | | | | |
| Leucine | L | Leu | UUA | UUG | CUA | CUC | CUG | CUU |
| Methionine | M | Met | AUG | | | | | |
| Asparagine | N | Asn | AAC | AAU | | | | |
| Proline | P | Pro | CCA | CCC | CCG | CCU | | |
| Glutamine | Q | Gln | CAA | CAG | | | | |
| Arginine | R | Arg | AGA | AGG | CGA | CGC | CGG | CGU |
| Serine | S | Ser | AGC | AGU | UCA | UCC | UCG | UCU |
| Threonine | T | Thr | ACA | ACC | ACG | ACU | | |
| Valine | V | Val | GUA | GUC | GUG | GUU | | |

TABLE 1-continued

Amino Acid Codons

| Amino Acids | One letter code | Three letter code | Codons | |
|---|---|---|---|---|
| Tryptophan | W | Trp | UGG | |
| Tyrosine | Y | Tyr | UAC | UAU |

Guidance in determining which amino acid residues can be substituted, inserted, or deleted without abolishing biological activity can be found using computer programs well known in the art, such as DNASTAR, DNA Strider, Geneious, Mac Vector, or Vector NTI software. Preferably, amino acid changes in the protein variants disclosed herein are conservative amino acid changes, i.e., substitutions of similarly charged or uncharged amino acids. A conservative amino acid change involves substitution of one of a family of amino acids which are related in their side chains. Naturally occurring amino acids are generally divided into four families: acidic (aspartate, glutamate), basic (lysine, arginine, histidine), non-polar (alanine, valine, leucine, isoleucine, proline, phenylalanine, methionine, tryptophan), and uncharged polar (glycine, asparagine, glutamine, cysteine, serine, threonine, tyrosine) amino acids. Phenylalanine, tryptophan, and tyrosine are sometimes classified jointly as aromatic amino acids. In a peptide or protein, suitable conservative substitutions of amino acids are known to those of skill in this art and generally can be made without altering a biological activity of a resulting molecule. Those of skill in this art recognize that, in general, single amino acid substitutions in non-essential regions of a polypeptide do not substantially alter biological activity (see, e.g., Watson et al. *Molecular Biology of the Gene*, 4th Edition, 1987, The Benjamin/Cummings Pub. Co., p.224).

In one embodiment, where expression of two or more polypeptides is desired, the polynucleotide sequences encoding them can be separated by and IRES sequence as disclosed elsewhere herein.

Polypeptides contemplated in particular embodiments include fusion polypeptides. In particular embodiments, fusion polypeptides and polynucleotides encoding fusion polypeptides are provided. Fusion polypeptides and fusion proteins refer to a polypeptide having at least two, three, four, five, six, seven, eight, nine, or ten polypeptide segments.

In another embodiment, two or more polypeptides can be expressed as a fusion protein that comprises one or more self-cleaving polypeptide sequences as disclosed elsewhere herein.

In one embodiment, a fusion protein contemplated herein comprises one or more DNA binding domains and one or more nucleases, and one or more linker and/or self-cleaving polypeptides.

In one embodiment, a fusion protein contemplated herein comprises nuclease variant; a linker or self-cleaving peptide; and an end-processing enzyme including but not limited to a 5'-3' exonuclease, a 5'-3' alkaline exonuclease, and a 3'-5' exonuclease (e.g., Trex2).

Fusion polypeptides can comprise one or more polypeptide domains or segments including, but are not limited to signal peptides, cell permeable peptide domains (CPP), DNA binding domains, nuclease domains, etc., epitope tags (e.g., maltose binding protein ("MBP"), glutathione S transferase (GST), HIS6, MYC, FLAG, V5, VSV-G, and HA), polypeptide linkers, and polypeptide cleavage signals. Fusion polypeptides are typically linked C-terminus to N-terminus, although they can also be linked C-terminus to C-terminus, N-terminus to N-terminus, or N-terminus to C-terminus. In particular embodiments, the polypeptides of the fusion protein can be in any order. Fusion polypeptides or fusion proteins can also include conservatively modified variants, polymorphic variants, alleles, mutants, subsequences, and interspecies homologs, so long as the desired activity of the fusion polypeptide is preserved. Fusion polypeptides may be produced by chemical synthetic methods or by chemical linkage between the two moieties or may generally be prepared using other standard techniques. Ligated DNA sequences comprising the fusion polypeptide are operably linked to suitable transcriptional or translational control elements as disclosed elsewhere herein.

Fusion polypeptides may optionally comprises a linker that can be used to link the one or more polypeptides or domains within a polypeptide. A peptide linker sequence may be employed to separate any two or more polypeptide components by a distance sufficient to ensure that each polypeptide folds into its appropriate secondary and tertiary structures so as to allow the polypeptide domains to exert their desired functions. Such a peptide linker sequence is incorporated into the fusion polypeptide using standard techniques in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., *Gene* 40:39-46, 1985; Murphy et al., *Proc. Natl. Acad. Sci. USA* 83:8258-8262, 1986; U.S. Pat. Nos. 4,935,233 and 4,751,180. Linker sequences are not required when a particular fusion polypeptide segment contains non-essential N-terminal amino acid regions that can be used to separate the functional domains and prevent steric interference. Preferred linkers are typically flexible amino acid subsequences which are synthesized as part of a recombinant fusion protein. Linker polypeptides can be between 1 and 200 amino acids in length, between 1 and 100 amino acids in length, or between 1 and 50 amino acids in length, including all integer values in between.

Exemplary linkers include, but are not limited to the following amino acid sequences: glycine polymers (G)n; glycine-serine polymers $(G_{1-5}S_{1-5})_n$, where n is an integer of at least one, two, three, four, or five; glycine-alanine polymers; alanine-serine polymers; GGG (SEQ ID NO: 30); DGGGS (SEQ ID NO: 31); TGEKP (SEQ ID NO: 32) (see e.g., Liu et al., *PNAS* 5525-5530 (1997)); GGRR (SEQ ID NO: 33) (Pomerantz et al. 1995, supra); $(GGGGS)_n$ wherein n=1, 2, 3, 4 or 5 (SEQ ID NO: 34) (Kim et al., *PNAS* 93, 1156-1160 (1996).); EGKSSGSGSESKVD (SEQ ID NO: 35) (Chaudhary et al., 1990, *Proc. Natl. Acad. Sci. U.S.A.* 87:1066-1070); KESGSVSSEQLAQFRSLD (SEQ ID NO: 36) (Bird et al., 1988, *Science* 242:423-426), GGRRGGGS (SEQ ID NO: 37); LRQRDGERP (SEQ ID NO: 38); LRQKDGGGSERP (SEQ ID NO: 39); LRQKD(GGGS)$_2$ERP (SEQ ID NO: 40). Alternatively, flexible linkers can be rationally designed using a computer program capable of modeling both DNA-binding sites and the peptides themselves (Desjarlais & Berg, *PNAS* 90:2256-2260 (1993), *PNAS* 91:11099-11103 (1994) or by phage display methods.

Fusion polypeptides may further comprise a polypeptide cleavage signal between each of the polypeptide domains described herein or between an endogenous open reading frame and a polypeptide encoded by a donor repair template. In addition, a polypeptide cleavage site can be put into any linker peptide sequence. Exemplary polypeptide cleavage signals include polypeptide cleavage recognition sites such as protease cleavage sites, nuclease cleavage sites (e.g., rare restriction enzyme recognition sites, self-cleaving ribozyme recognition sites), and self-cleaving viral oligopeptides (see deFelipe and Ryan, 2004. *Traffic*, 5(8); 616-26).

Suitable protease cleavages sites and self-cleaving peptides are known to the skilled person (see, e.g., in Ryan et al., 1997. *J. Gener. Virol.* 78, 699-722; Scymczak et al. (2004) *Nature Biotech.* 5, 589-594). Exemplary protease cleavage sites include, but are not limited to the cleavage sites of potyvirus Ma proteases (e.g., tobacco etch virus protease), potyvirus HC proteases, potyvirus P1 (P35) proteases, byovirus NIa proteases, byovirus RNA-2-encoded proteases, aphthovirus L proteases, enterovirus 2A proteases, rhinovirus 2A proteases, picorna 3C proteases, comovirus 24K proteases, nepovirus 24K proteases, RTSV (rice tungro spherical virus) 3C-like protease, PYVF (parsnip yellow fleck virus) 3C-like protease, heparin, thrombin, factor Xa and enterokinase. Due to its high cleavage stringency, TEV (tobacco etch virus) protease cleavage sites are preferred in one embodiment, e.g., EXXYXQ(G/S) (SEQ ID NO: 41), for example, ENLYFQG (SEQ ID NO: 42) and ENLYFQS (SEQ ID NO: 43), wherein X represents any amino acid (cleavage by TEV occurs between Q and G or Q and S).

In certain embodiments, the self-cleaving polypeptide site comprises a 2A or 2A-like site, sequence or domain (Donnelly et al., 2001. *J. Gen. Virol.* 82:1027-1041). In a particular embodiment, the viral 2A peptide is an aphthovirus 2A peptide, a potyvirus 2A peptide, or a cardiovirus 2A peptide.

In one embodiment, the viral 2A peptide is selected from the group consisting of: a foot-and-mouth disease virus (FMDV) 2A peptide, an equine rhinitis A virus (ERAV) 2A peptide, a Thosea asigna virus (TaV) 2A peptide, a porcine teschovirus-1 (PTV-1) 2A peptide, a Theilovirus 2A peptide, and an encephalomyocarditis virus 2A peptide.

Illustrative examples of 2A sites are provided in Table 2.

TABLE 2

| Exemplary 2A sites include the following sequences: | |
|---|---|
| SEQ ID NO: 44 | GSGATNFSLLKQAGDVEENPGP |
| SEQ ID NO: 45 | ATNFSLLKQAGDVEENPGP |
| SEQ ID NO: 46 | LLKQAGDVEENPGP |
| SEQ ID NO: 47 | GSGEGRGSLLTCGDVEENPGP |

TABLE 2-continued

| Exemplary 2A sites include the following sequences: | |
|---|---|
| SEQ ID NO: 48 | EGRGSLLTCGDVEENPGP |
| SEQ ID NO: 49 | LLTCGDVEENPGP |
| SEQ ID NO: 50 | GSGQCTNYALLKLAGDVESNPGP |
| SEQ ID NO: 51 | QCTNYALLKLAGDVESNPGP |
| SEQ ID NO: 52 | LLKLAGDVESNPGP |
| SEQ ID NO: 53 | GSGVKQTLNFDLLKLAGDVESNPGP |
| SEQ ID NO: 54 | VKQTLNFDLLKLAGDVESNPGP |
| SEQ ID NO: 55 | LLKLAGDVESNPGP |
| SEQ ID NO: 56 | LLNFDLLKLAGDVESNPGP |
| SEQ ID NO: 57 | TLNFDLLKLAGDVESNPGP |
| SEQ ID NO: 58 | LLKLAGDVESNPGP |
| SEQ ID NO: 59 | NFDLLKLAGDVESNPGP |
| SEQ ID NO: 60 | QLLNFDLLKLAGDVESNPGP |
| SEQ ID NO: 61 | APVKQTLNFDLLKLAGDVESNPGP |
| SEQ ID NO: 62 | VTELLYRMKRAETYCPRPLLAIHPT EARHKQKIVAPVKQT |
| SEQ ID NO: 63 | LNFDLLKLAGDVESNPGP |
| SEQ ID NO: 64 | LLAIHPTEARHKQKIVAPVKQTLN FDLLKLAGDVESNPGP |
| SEQ ID NO: 65 | EARHKQKIVAPVKQTLNFDLLKLAGDVESNPGP |

E. Polynucleotides

In particular embodiments, polynucleotides encoding one or more homing endonuclease variants, megaTALs, end-processing enzymes, and fusion polypeptides contemplated herein are provided. As used herein, the terms "polynucleotide" or "nucleic acid" refer to deoxyribonucleic acid (DNA), ribonucleic acid (RNA) and DNA/RNA hybrids. Polynucleotides may be single-stranded or double-stranded and either recombinant, synthetic, or isolated. Polynucleotides include, but are not limited to: pre-messenger RNA (pre-mRNA), messenger RNA (mRNA), RNA, short interfering RNA (siRNA), short hairpin RNA (shRNA), microRNA (miRNA), ribozymes, genomic RNA (gRNA), plus strand RNA (RNA(+)), minus strand RNA (RNA(−)), tracrRNA, crRNA, single guide RNA (sgRNA), synthetic RNA, synthetic mRNA, genomic DNA (gDNA), PCR amplified DNA, complementary DNA (cDNA), synthetic DNA, or recombinant DNA. Polynucleotides refer to a polymeric form of nucleotides of at least 5, at least 10, at least 15, at least 20, at least 25, at least 30, at least 40, at least 50, at least 100, at least 200, at least 300, at least 400, at least 500, at least 1000, at least 5000, at least 10000, or at least 15000 or more nucleotides in length, either ribonucleotides or deoxyribonucleotides or a modified form of either type of nucleotide, as well as all intermediate lengths. It will be readily understood that "intermediate lengths," in this context, means any length between the quoted values, such as 6, 7, 8, 9, etc., 101, 102, 103, etc.; 151, 152, 153, etc.; 201, 202, 203, etc. In particular embodiments, polynucleotides or variants have at least or about 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity to a reference sequence.

In particular embodiments, polynucleotides may be codon-optimized. As used herein, the term "codon-optimized" refers to substituting codons in a polynucleotide encoding a polypeptide in order to increase the expression, stability and/or activity of the polypeptide. Factors that influence codon optimization include, but are not limited to one or more of: (i) variation of codon biases between two or more organisms or genes or synthetically constructed bias tables, (ii) variation in the degree of codon bias within an organism, gene, or set of genes, (iii) systematic variation of codons including context, (iv) variation of codons according to their decoding tRNAs, (v) variation of codons according to GC %, either overall or in one position of the triplet, (vi) variation in degree of similarity to a reference sequence for example a naturally occurring sequence, (vii) variation in the codon frequency cutoff, (viii) structural properties of mRNAs transcribed from the DNA sequence, (ix) prior knowledge about the function of the DNA sequences upon which design of the codon substitution set is to be based, (x) systematic variation of codon sets for each amino acid, and/or (xi) isolated removal of spurious translation initiation sites.

As used herein the term "nucleotide" refers to a heterocyclic nitrogenous base in N-glycosidic linkage with a phosphorylated sugar. Nucleotides are understood to include natural bases, and a wide variety of art-recognized modified bases. Such bases are generally located at the position of a nucleotide sugar moiety. Nucleotides generally comprise a base, sugar and a phosphate group. In ribonucleic acid (RNA), the sugar is a ribose, and in deoxyribonucleic acid (DNA) the sugar is a deoxyribose, i.e., a sugar lacking a hydroxyl group that is present in ribose. Exemplary natural nitrogenous bases include the purines, adenosine (A) and guanidine (G), and the pyrimidines, cytidine (C) and thymidine (T) (or in the context of RNA, uracil (U)). The C-1 atom of deoxyribose is bonded to N-1 of a pyrimidine or N-9 of a purine. Nucleotides are usually mono, di- or triphosphates. The nucleotides can be unmodified or modified at the sugar, phosphate and/or base moiety, (also referred to interchangeably as nucleotide analogs, nucleotide derivatives, modified nucleotides, non-natural nucleotides, and non-standard nucleotides; see for example, WO 92/07065 and WO 93/15187). Examples of modified nucleic acid bases are summarized by Limbach et al., (1994, *Nucleic Acids Res.* 22, 2183-2196).

A nucleotide may also be regarded as a phosphate ester of a nucleoside, with esterification occurring on the hydroxyl group attached to C-5 of the sugar. As used herein, the term "nucleoside" refers to a heterocyclic nitrogenous base in N-glycosidic linkage with a sugar. Nucleosides are recognized in the art to include natural bases, and also to include well known modified bases. Such bases are generally located at the position of a nucleoside sugar moiety. Nucleosides generally comprise a base and sugar group. The nucleosides can be unmodified or modified at the sugar, and/or base moiety, (also referred to interchangeably as nucleoside analogs, nucleoside derivatives, modified nucleosides, non-natural nucleosides, or non-standard nucleosides). As also noted above, examples of modified nucleic acid bases are summarized by Limbach et al., (1994, *Nucleic Acids Res.* 22, 2183-2196).

Illustrative examples of polynucleotides include, but are not limited to polynucleotides encoding SEQ ID NOs: 1-12 and 22-24, and polynucleotide sequences set forth in SEQ ID NOs: 13-16 and 25-27.

In various illustrative embodiments, polynucleotides contemplated herein include, but are not limited to polynucleotides encoding homing endonuclease variants, megaTALs, end-processing enzymes, fusion polypeptides, and expression vectors, viral vectors, and transfer plasmids comprising polynucleotides contemplated herein.

As used herein, the terms "polynucleotide variant" and "variant" and the like refer to polynucleotides displaying substantial sequence identity with a reference polynucleotide sequence or polynucleotides that hybridize with a reference sequence under stringent conditions that are defined hereinafter. These terms also encompass polynucleotides that are distinguished from a reference polynucleotide by the addition, deletion, substitution, or modification of at least one nucleotide. Accordingly, the terms "polynucleotide variant" and "variant" include polynucleotides in which one or more nucleotides have been added or deleted, or modified, or replaced with different nucleotides. In this regard, it is well understood in the art that certain alterations inclusive of mutations, additions, deletions and substitutions can be made to a reference polynucleotide whereby the altered polynucleotide retains the biological function or activity of the reference polynucleotide.

In one embodiment, a polynucleotide comprises a nucleotide sequence that hybridizes to a target nucleic acid sequence under stringent conditions. To hybridize under "stringent conditions" describes hybridization protocols in which nucleotide sequences at least 60% identical to each other remain hybridized. Generally, stringent conditions are selected to be about 5° C. lower than the thermal melting point (Tm) for the specific sequence at a defined ionic strength and pH. The Tm is the temperature (under defined ionic strength, pH and nucleic acid concentration) at which 50% of the probes complementary to the target sequence hybridize to the target sequence at equilibrium. Since the target sequences are generally present at excess, at Tm, 50% of the probes are occupied at equilibrium.

The recitations "sequence identity" or, for example, comprising a "sequence 50% identical to," as used herein, refer to the extent that sequences are identical on a nucleotide-by-nucleotide basis or an amino acid-by-amino acid basis over a window of comparison. Thus, a "percentage of sequence identity" may be calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity. Included are nucleotides and polypeptides having at least about 50%, 55%, 60%, 65%, 70%, 75%, 80%, 85%, 90%, 95%, 96%, 97%, 98%, 99% or 100% sequence identity to any of the reference sequences described herein, typically where the polypeptide variant maintains at least one biological activity of the reference polypeptide.

Terms used to describe sequence relationships between two or more polynucleotides or polypeptides include "reference sequence," "comparison window," "sequence identity," "percentage of sequence identity," and "substantial identity". A "reference sequence" is at least 12 but frequently 15 to 18 and often at least 25 monomer units, inclusive of nucleotides and amino acid residues, in length. Because two polynucleotides may each comprise (1) a sequence (i.e., only a portion of the complete polynucleotide sequence) that is similar between the two polynucleotides, and (2) a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window" refers to a conceptual segment of at least 6 contiguous positions, usually about 50 to about 100, more usually about 100 to about 150 in which a sequence is compared to a reference sequence of the same number of contiguous positions after the two sequences are optimally aligned. The comparison window may comprise additions or deletions (i.e., gaps) of about 20% or less as compared to the reference sequence (which does not comprise additions or deletions) for optimal alignment of the two sequences. Optimal alignment of sequences for aligning a comparison window may be conducted by computerized implementations of algorithms (GAP, BESTFIT, FASTA, and TFASTA in the Wisconsin Genetics Software Package Release 7.0, Genetics Computer Group, 575 Science Drive Madison, Wis., USA) or by inspection and the best alignment (i.e., resulting in the highest percentage homology over the comparison window) generated by any of the various methods selected. Reference also may be made to the BLAST family of programs as for example disclosed by Altschul et al., 1997, *Nucl. Acids Res.* 25:3389. A detailed discussion of sequence analysis can be found in Unit 19.3 of Ausubel et al., *Current Protocols in Molecular Biology*, John Wiley & Sons Inc., 1994-1998, Chapter 15.

An "isolated polynucleotide," as used herein, refers to a polynucleotide that has been purified from the sequences which flank it in a naturally-occurring state, e.g., a DNA fragment that has been removed from the sequences that are normally adjacent to the fragment. In particular embodiments, an "isolated polynucleotide" refers to a complementary DNA (cDNA), a recombinant polynucleotide, a synthetic polynucleotide, or other polynucleotide that does not exist in nature and that has been made by the hand of man.

In various embodiments, a polynucleotide comprises an mRNA encoding a polypeptide contemplated herein including, but not limited to, a homing endonuclease variant, a megaTAL, and an end-processing enzyme. In certain embodiments, the mRNA comprises a cap, one or more nucleotides, and a poly(A) tail.

As used herein, the terms "5' cap" or "5' cap structure" or "5' cap moiety" refer to a chemical modification, which has been incorporated at the 5' end of an mRNA. The 5' cap is involved in nuclear export, mRNA stability, and translation.

In particular embodiments, a mRNA contemplated herein comprises a 5' cap comprising a 5'-ppp-5'-triphosphate linkage between a terminal guanosine cap residue and the 5'-terminal transcribed sense nucleotide of the mRNA molecule. This 5'-guanylate cap may then be methylated to generate an N7-methyl-guanylate residue.

Illustrative examples of 5' cap suitable for use in particular embodiments of the mRNA polynucleotides contemplated herein include, but are not limited to: unmethylated 5' cap analogs, e.g., G(5)ppp(5')G, G(5')ppp(5')C, G(5')ppp(5')A; methylated 5' cap analogs, e.g., m$^7$G(5')ppp(5')G, m$^7$G(5)ppp(5')C, and m$^7$G(5)ppp(5')A; dimethylated 5' cap analogs, e.g., m$^{2,7}$G(5')ppp(5')G, m$^{2,7}$G(5')ppp(5')C, and m$^{2,7}$G (5')ppp(5')A; trimethylated 5' cap analogs, e.g., m$^{2,2,7}$G(5') ppp(5')G, m$^{2,2,7}$G(5')ppp(5')C, and m$^{2,2,7}$G(5')ppp(5')A; dimethylated symmetrical 5' cap analogs, e.g., m$^7$G(5') pppm$^7$(5')G, m$^7$G(5')pppm$^7$(5')C, and m$^7$G(5')pppm$^7$(5')A; and anti-reverse 5' cap analogs, e.g., Anti-Reverse Cap Analog (ARCA) cap, designated 3'O-Me-m$^7$G(5')ppp(5')G, 2'O-Me-m$^7$G(5')ppp(5')G, 2'O-Me-m$^7$G(5')ppp(5')C, 2'O-Me-m$^7$G(5)ppp(5')A, m$^7$2'd(5)ppp(5')G, m$^7$2'd(5)ppp(5')C, m$^7$2'd(5)ppp(5')A, 3'O-Me-m$^7$G(5')ppp(5')C, 3'O-Me-m$^7$G (5')ppp(5')A, m$^7$3'd(5')ppp(5')G, m$^7$3'd(5')ppp(5')C, m$^7$3'd (5')ppp(5')A and their tetraphosphate derivatives) (see, e.g., Jemielity et al., RNA, 9: 1108-1122 (2003)).

In particular embodiments, mRNAs comprise a 5' cap that is a 7-methyl guanylate ("m$^7$G") linked via a triphosphate bridge to the 5'-end of the first transcribed nucleotide, resulting in m$^7$G(5')ppp(5')N, where N is any nucleoside.

In some embodiments, mRNAs comprise a 5' cap wherein the cap is a Cap0 structure (Cap0 structures lack a 2'-O-methyl residue of the ribose attached to bases 1 and 2), a Cap1 structure (Cap1 structures have a 2'-O-methyl residue at base 2), or a Cap2 structure (Cap2 structures have a 2'-O-methyl residue attached to both bases 2 and 3).

In one embodiment, an mRNA comprises a m$^7$G(5')ppp (5')G cap.

In one embodiment, an mRNA comprises an ARCA cap.

In particular embodiments, an mRNA contemplated herein comprises one or more modified nucleosides.

In one embodiment, an mRNA comprises one or more modified nucleosides selected from the group consisting of: pseudouridine, pyridin-4-one ribonucleoside, 5-aza-uridine, 2-thio-5-aza-uridine, 2-thiouridine, 4-thio-pseudouridine, 2-thio-pseudouridine, 5-hydroxyuridine, 3-methyluridine, 5-carboxymethyl-uridine, 1-carboxymethyl-pseudouridine, 5-propynyl-uridine, 1-propynyl-pseudouridine, 5-taurinomethyluridine, 1-taurinomethyl-pseudouridine, 5-taurinomethyl-2-thio-uridine, 1-taurinomethyl-4-thio-uridine, 5-methyl-uridine, 1-methyl-pseudouridine, 4-thio-1-methyl-pseudouridine, 2-thio-1-methyl-pseudouridine, 1-methyl-1-deaza-pseudouridine, 2-thio-1-methyl-1-deaza-pseudouridine, dihydrouridine, dihydropseudouridine, 2-thio-dihydrouridine, 2-thio-dihydropseudouridine, 2-methoxyuridine, 2-methoxy-4-thio-uridine, 4-methoxy-pseudouridine, 4-methoxy-2-thio-pseudouridine, 5-aza-cytidine, pseudoisocytidine, 3-methyl-cytidine, N4-acetylcytidine, 5-formylcytidine, N4-methylcytidine, 5-hydroxymethylcytidine, 1-methyl-pseudoisocytidine, pyrrolo-cytidine, pyrrolo-pseudoisocytidine, 2-thio-cytidine, 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, 4-methoxy-1-methyl-pseudoisocytidine, 2-aminopurine, 2,6-diaminopurine, 7-deaza-adenine, 7-deaza-8-aza-adenine, 7-deaza-2-aminopurine, 7-deaza-8-aza-2-aminopurine, 7-deaza-2,6-diaminopurine, 7-deaza-8-aza-2, 6-diaminopurine, 1-methyladenosine, N6-methyladenosine, N6-isopentenyladenosine, N6-(cis-hydroxyisopentenyl)adenosine, 2-methylthio-N6-(cis-hydroxyisopentenyl) adenosine, N6-glycinylcarbamoyladenosine, N6-threonylcarbamoyladenosine, 2-methylthio-N6-threonyl carbamoyladenosine, N6,N6-dimethyladenosine, 7-methyl-adenine, 2-methylthio-adenine, 2-methoxy-adenine, inosine, 1-methyl-inosine, wyosine, wybutosine, 7-deaza-guanosine, 7-deaza-8-aza-guanosine, 6-thio-guanosine, 6-thio-7-deaza-guanosine, 6-thio-7-deaza-8-aza-guanosine, 7-methylguanosine, 6-thio-7-methyl-guanosine, 7-methylinosine, 6-methoxy-guanosine, 1-methylguanosine, N2-methylguanosine, N2,N2-dimethylguanosine, 8-oxo-guanosine, 7-methyl-8-oxo-guanosine, 1-methyl-6-thio-guanosine, N2-methyl-6-thio-guanosine, and N2,N2-dimethyl-6-thio-guanosine.

In one embodiment, an mRNA comprises one or more modified nucleosides selected from the group consisting of: pseudouridine, pyridin-4-one ribonucleoside, 5-aza-uridine, 2-thio-5-aza-uridine, 2-thiouridine, 4-thio-pseudouridine, 2-thio-pseudouridine, 5-hydroxyuridine, 3-methyluridine, 5-carboxymethyl-uridine, 1-carboxymethyl-pseudouridine, 5-propynyl-uridine, 1-propynyl-pseudouridine, 5-taurinomethyluridine, 1-taurinomethyl-pseudouridine, 5-taurinomethyl-2-thio-uridine, 1-taurinomethyl-4-thio-uridine, 5-methyl-uridine, 1-methyl-pseudouridine, 4-thio-1-methyl-pseudouridine, 2-thio-1-methyl-pseudouridine, 1-methyl-1-deaza-pseudouridine, 2-thio-1-methyl-1-deaza-pseudouridine, dihydrouridine, dihydropseudouridine, 2-thio-dihydrouridine, 2-thio-dihydropseudouridine, 2-methoxyuridine, 2-methoxy-4-thio-uridine, 4-methoxy-pseudouridine, and 4-methoxy-2-thio-pseudouridine.

In one embodiment, an mRNA comprises one or more modified nucleosides selected from the group consisting of: 5-aza-cytidine, pseudoisocytidine, 3-methyl-cytidine, N4-acetylcytidine, 5-formylcytidine, N4-methylcytidine, 5-hydroxymethylcytidine, 1-methyl-pseudoisocytidine, pyrrolo-cytidine, pyrrolo-pseudoisocytidine, 2-thio-cytidine, 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, and 4-methoxy-1-methyl-pseudoisocytidine.

In one embodiment, an mRNA comprises one or more modified nucleosides selected from the group consisting of: 2-aminopurine, 2,6-diaminopurine, 7-deaza-adenine, 7-deaza-8-aza-adenine, 7-deaza-2-aminopurine, 7-deaza-8-aza-2-aminopurine, 7-deaza-2,6-diaminopurine, 7-deaza-8-aza-2,6-diaminopurine, 1-methyladenosine, N6-methyladenosine, N6-isopentenyladenosine, N6-(cis-hydroxyisopentenyl)adenosine, 2-methylthio-N6-(cis-hydroxyisopentenyl) adenosine, N6-glycinylcarbamoyladenosine, N6-threonylcarbamoyladenosine, 2-methylthio-N6-threonyl carbamoyladenosine, N6,N6-dimethyladenosine, 7-methyladenine, 2-methylthio-adenine, and 2-methoxy-adenine.

In one embodiment, an mRNA comprises one or more modified nucleosides selected from the group consisting of: inosine, 1-methyl-inosine, wyosine, wybutosine, 7-deaza-guanosine, 7-deaza-8-aza-guanosine, 6-thio-guanosine, 6-thio-7-deaza-guanosine, 6-thio-7-deaza-8-aza-guanosine, 7-methyl-guanosine, 6-thio-7-methyl-guanosine, 7-methyl-inosine, 6-methoxy-guanosine, 1-methylguanosine, N2-methylguanosine, N2,N2-dimethylguanosine, 8-oxo-guanosine, 7-methyl-8-oxo-guanosine, 1-methyl-6-thio-guanosine, N2-methyl-6-thio-guanosine, and N2,N2-dimethyl-6-thio-guanosine.

In one embodiment, an mRNA comprises one or more pseudouridines, one or more 5-methyl-cytosines, and/or one or more 5-methyl-cytidines.

In one embodiment, an mRNA comprises one or more pseudouridines.

In one embodiment, an mRNA comprises one or more 5-methyl-cytidines.

In one embodiment, an mRNA comprises one or more 5-methyl-cytosines.

In particular embodiments, an mRNA contemplated herein comprises a poly(A) tail to help protect the mRNA from exonuclease degradation, stabilize the mRNA, and facilitate translation. In certain embodiments, an mRNA comprises a 3' poly(A) tail structure.

In particular embodiments, the length of the poly(A) tail is at least about 10, 25, 50, 75, 100, 150, 200, 250, 300, 350, 400, 450, or at least about 500 or more adenine nucleotides or any intervening number of adenine nucleotides. In particular embodiments, the length of the poly(A) tail is at least about 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 202, 203, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, or 275 or more adenine nucleotides.

In particular embodiments, the length of the poly(A) tail is about 10 to about 500 adenine nucleotides, about 50 to about 500 adenine nucleotides, about 100 to about 500 adenine nucleotides, about 150 to about 500 adenine nucleotides, about 200 to about 500 adenine nucleotides, about 250 to about 500 adenine nucleotides, about 300 to about 500 adenine nucleotides, about 50 to about 450 adenine nucleotides, about 50 to about 400 adenine nucleotides, about 50 to about 350 adenine nucleotides, about 100 to about 500 adenine nucleotides, about 100 to about 450 adenine nucleotides, about 100 to about 400 adenine nucleotides, about 100 to about 350 adenine nucleotides, about 100 to about 300 adenine nucleotides, about 150 to about 500 adenine nucleotides, about 150 to about 450 adenine nucleotides, about 150 to about 400 adenine nucleotides, about 150 to about 350 adenine nucleotides, about 150 to about 300 adenine nucleotides, about 150 to about 250 adenine nucleotides, about 150 to about 200 adenine nucleotides, about 200 to about 500 adenine nucleotides, about 200 to about 450 adenine nucleotides, about 200 to about 400 adenine nucleotides, about 200 to about 350 adenine nucleotides, about 200 to about 300 adenine nucleotides, about 250 to about 500 adenine nucleotides, about 250 to about 450 adenine nucleotides, about 250 to about 400 adenine nucleotides, about 250 to about 350 adenine nucleotides, or about 250 to about 300 adenine nucleotides or any intervening range of adenine nucleotides.

Terms that describe the orientation of polynucleotides include: 5' (normally the end of the polynucleotide having a free phosphate group) and 3' (normally the end of the polynucleotide having a free hydroxyl (OH) group). Polynucleotide sequences can be annotated in the 5' to 3' orientation or the 3' to 5' orientation. For DNA and mRNA, the 5' to 3' strand is designated the "sense," "plus," or "coding" strand because its sequence is identical to the sequence of the pre-messenger (pre-mRNA) [except for uracil (U) in RNA, instead of thymine (T) in DNA]. For DNA and mRNA, the complementary 3' to 5' strand which is the strand transcribed by the RNA polymerase is designated as "template," "antisense," "minus," or "non-coding" strand. As used herein, the term "reverse orientation" refers to a 5' to 3' sequence written in the 3' to 5' orientation or a 3' to 5' sequence written in the 5' to 3' orientation.

The terms "complementary" and "complementarity" refer to polynucleotides (i.e., a sequence of nucleotides) related by the base-pairing rules. For example, the complementary strand of the DNA sequence 5' A G T C A T G 3' is 3' T C A G T A C 5'. The latter sequence is often written as the reverse complement with the 5' end on the left and the 3' end on the right, 5' C A T G A C T 3'. A sequence that is equal to its reverse complement is said to be a palindromic sequence. Complementarity can be "partial," in which only some of the nucleic acids' bases are matched according to the base pairing rules. Or, there can be "complete" or "total" complementarity between the nucleic acids.

Polynucleotides can be prepared, manipulated, expressed and/or delivered using any of a variety of well-established techniques known and available in the art. In order to express a desired polypeptide, a nucleotide sequence encoding the polypeptide, can be inserted into appropriate vector. A desired polypeptide can also be expressed by delivering an mRNA encoding the polypeptide into the cell.

Illustrative examples of vectors include, but are not limited to plasmid, autonomously replicating sequences, and transposable elements, e.g., Sleeping Beauty, PiggyBac.

Additional illustrative examples of vectors include, without limitation, plasmids, phagemids, cosmids, artificial chromosomes such as yeast artificial chromosome (YAC), bacterial artificial chromosome (BAC), or P1-derived artificial chromosome (PAC), bacteriophages such as lambda phage or M13 phage, and animal viruses.

Illustrative examples of viruses useful as vectors include, without limitation, retrovirus (including lentivirus and integration deficient lentivirus), adenovirus, adeno-associated virus, herpesvirus (e.g., herpes simplex virus), poxvirus, baculovirus, papillomavirus, and papovavirus (e.g., SV40).

Illustrative examples of expression vectors include, but are not limited to pClneo vectors (Promega) for expression in mammalian cells; PLENTI4/V5-DEST™, PLENTI6/V5-DEST™, AND PLENTI6.2/V5-GW/LACZ (Invitrogen) lentiviral expression vectors for lentivirus-mediated gene transfer and expression in mammalian cells. In particular embodiments, coding sequences of polypeptides disclosed herein can be ligated into such expression vectors for the expression of the polypeptides in mammalian cells.

In particular embodiments, the vector is an episomal vector or a vector that is maintained extrachromosomally. As used herein, the term "episomal" refers to a vector that is able to replicate without integration into host's chromosomal DNA and without gradual loss from a dividing host cell also meaning that said vector replicates extrachromosomally or episomally.

In particular embodiments, to achieve efficient translation of each of the plurality of polypeptides, the polynucleotide sequences can be separated by one or more IRES sequences or polynucleotide sequences encoding self-cleaving polypeptides.

As used herein, an "internal ribosome entry site" or "IRES" refers to an element that promotes direct internal ribosome entry to the initiation codon, such as ATG, of a cistron (a protein encoding region), thereby leading to the cap-independent translation of the gene. See, e.g., Jackson et al., 1990. *Trends Biochem Sci* 15(12):477-83) and Jackson and Kaminski. 1995. *RNA* 1(10):985-1000. Examples of IRES generally employed by those of skill in the art include those described in U.S. Pat. No. 6,692,736. Further examples of "IRES" known in the art include, but are not limited to IRES obtainable from picornavirus (Jackson et al., 1990) and IRES obtainable from viral or cellular mRNA sources, such as for example, immunoglobulin heavy-chain binding protein (BiP), the vascular endothelial growth factor (VEGF) (Huez et al. 1998. *Mol. Cell. Biol.* 18(11):6178-6190), the fibroblast growth factor 2 (FGF-2), and insulin-like growth factor (IGFII), the translational initiation factor eIF4G and yeast transcription factors TFIID and HAP4, the encephelomycarditis virus (EMCV) which is commercially available from Novagen (Duke et al., 1992. *J. Virol* 66(3): 1602-9) and the VEGF IRES (Huez et al., 1998. *Mol Cell Biol* 18(11):6178-90). IRES have also been reported in viral genomes of Picornaviridae, Dicistroviridae and Flaviviridae species and in HCV, Friend murine leukemia virus (FrMLV) and Moloney murine leukemia virus (MoMLV).

In one embodiment, the IRES used in polynucleotides contemplated herein is an EMCV IRES.

In particular embodiments, the polynucleotides comprise polynucleotides that have a consensus Kozak sequence and that encode a desired polypeptide. As used herein, the term "Kozak sequence" refers to a short nucleotide sequence that greatly facilitates the initial binding of mRNA to the small subunit of the ribosome and increases translation. The consensus Kozak sequence is (GCC)RCCATGG (SEQ ID NO: 66), where R is a purine (A or G) (Kozak, 1986. *Cell.* 44(2):283-92, and Kozak, 1987. *Nucleic Acids Res.* 15(20): 8125-48).

Elements directing the efficient termination and polyadenylation of the heterologous nucleic acid transcripts increases heterologous gene expression.

In particular embodiments, vectors comprise a polyadenylation sequence 3' of a polynucleotide encoding a polypeptide to be expressed. The term "poly(A) site" or "poly(A) sequence" as used herein denotes a DNA sequence which directs both the termination and polyadenylation of the nascent RNA transcript by RNA polymerase II. Polyadenylation sequences can promote mRNA stability by addition of a poly(A) tail to the 3' end of the coding sequence and thus, contribute to increased translational efficiency. Cleavage and polyadenylation is directed by a poly(A) sequence in the RNA. The core poly(A) sequence for mammalian pre-mRNAs has two recognition elements flanking a cleavage-polyadenylation site. Typically, an almost invariant AAUAAA hexamer lies 20-50 nucleotides upstream of a more variable element rich in U or GU residues. Cleavage of the nascent transcript occurs between these two elements and is coupled to the addition of up to 250 adenosines to the 5' cleavage product. In particular embodiments, the core poly(A) sequence is a synthetic poly(A) sequence (e.g., AATAAA, ATTAAA, AGTAAA). Illustrative examples of poly(A) sequences include, but are not limited to an SV40 poly(A) sequence, a bovine growth hormone poly(A) sequence (BGHpA), a rabbit β-globin poly(A) sequence (rβgpA), or another suitable heterologous or endogenous poly(A) sequence known in the art.

In particular embodiments, polynucleotides encoding one or more nuclease variants, megaTALs, end-processing enzymes, or fusion polypeptides may be introduced into hematopoietic cells, e.g., T cells, by both non-viral and viral methods. In particular embodiments, delivery of one or more polynucleotides encoding nucleases and/or donor repair templates may be provided by the same method or by different methods, and/or by the same vector or by different vectors.

The term "vector" is used herein to refer to a nucleic acid molecule capable transferring or transporting another nucleic acid molecule. The transferred nucleic acid is generally linked to, e.g., inserted into, the vector nucleic acid molecule. A vector may include sequences that direct autonomous replication in a cell, or may include sequences sufficient to allow integration into host cell DNA. In particular embodiments, non-viral vectors are used to deliver one or more polynucleotides contemplated herein to a T cell.

Illustrative examples of non-viral vectors include, but are not limited to plasmids (e.g., DNA plasmids or RNA plasmids), transposons, cosmids, and bacterial artificial chromosomes.

Illustrative methods of non-viral delivery of polynucleotides contemplated in particular embodiments include, but are not limited to: electroporation, sonoporation, lipofection, microinjection, biolistics, virosomes, liposomes, immunoliposomes, nanoparticles, polycation or lipid:nucleic acid conjugates, naked DNA, artificial virions, DEAE-dextran-mediated transfer, gene gun, and heat-shock.

Illustrative examples of polynucleotide delivery systems suitable for use in particular embodiments contemplated in particular embodiments include, but are not limited to those provided by Amaxa Biosystems, Maxcyte, Inc., BTX Molecular Delivery Systems, and Copernicus Therapeutics Inc. Lipofection reagents are sold commercially (e.g., Transfectam™ and Lipofectin™). Cationic and neutral lipids that are suitable for efficient receptor-recognition lipofection of polynucleotides have been described in the literature. See e.g., Liu et al. (2003) *Gene Therapy.* 10:180-187; and Balazs et al. (2011) *Journal of Drug Delivery.* 2011:1-12. Antibody-targeted, bacterially derived, non-living nanocell-based delivery is also contemplated in particular embodiments.

F. Cells

The genome edited cells manufactured by the methods contemplated in particular embodiments comprise one or more gene edits in a TCRα gene and provide improved cell-based therapeutics for the prevention, treatment, or amelioration of at least one symptom, of a cancer, GVHD, infectious disease, autoimmune disease, immunodeficiency or condition associated therewith. Without wishing to be bound to any particular theory, it is believed that the genome edited immune effector cells manufactured by the methods contemplated herein are imbued with superior properties, including increased improved safety, efficacy, and durability in vivo.

Genome edited cells contemplated in particular embodiments may be autologous/autogeneic ("self") or non-autologous ("non-self," e.g., allogeneic, syngeneic or xenogeneic). "Autologous," as used herein, refers to cells from the same subject. "Allogeneic," as used herein, refers to cells of the same species that differ genetically to the cell in comparison. "Syngeneic," as used herein, refers to cells of a different subject that are genetically identical to the cell in comparison. "Xenogeneic," as used herein, refers to cells of a different species to the cell in comparison. In preferred embodiments, the cells are obtained from a mammalian subject. In a more preferred embodiment, the cells are obtained from a primate subject, optionally a non-human primate. In the most preferred embodiment, the cells are obtained from a human subject.

An "isolated cell" refers to a non-naturally occurring cell, e.g., a cell that does not exist in nature, a modified cell, an engineered cell, etc., that has been obtained from an in vivo tissue or organ and is substantially free of extracellular matrix.

As used herein, the term "population of cells" refers to a plurality of cells that may be made up of any number and/or combination of homogenous or heterogeneous cell types, as described elsewhere herein. For example, for transduction of T cells, a population of cells may be isolated or obtained from peripheral blood. A population of cells may comprise about 10%, about 20%, about 30%, about 40%, about 50%, about 60%, about 70%, about 80%, about 90%, or about 100% of the target cell type to be edited. In certain embodiments, T cells may be isolated or purified from a population of heterogeneous cells using methods known in the art.

Illustrative examples of cell types whose genome can be edited using the compositions and methods contemplated herein include, but are not limited to, cell lines, primary cells, stem cells, progenitor cells, and differentiated cells, and mixtures thereof.

In a preferred embodiment, the genome editing compositions and methods are used to edit hematopoietic cells, more preferably immune cells, and even more preferably T cells.

The terms "T cell" or "T lymphocyte" are art-recognized and are intended to include thymocytes, immune effector cells, regulatory T cells, naïve T lymphocytes, immature T lymphocytes, mature T lymphocytes, resting T lymphocytes, or activated T lymphocytes. A T cell can be a T helper (Th) cell, for example a T helper 1 (Th1) or a T helper 2 (Th2) cell. The T cell can be a helper T cell (HTL; CD4$^+$ T cell) CD4$^+$ T cell, a cytotoxic T cell (CTL; CD8$^+$ T cell), a tumor infiltrating cytotoxic T cell (TIL; CD8$^+$ T cell), CD4$^+$CD8$^+$ T cell, CD4$^-$CD8$^-$ T cell, or any other subset of T cells. In one embodiment, the T cell is an immune effector cell. In one embodiment, the T cell is an NKT cell. Other illustrative populations of T cells suitable for use in particular embodiments include naïve T cells and memory T cells.

In various embodiments, genome edited cells comprise immune effector cells comprising a TCRα gene edited by the compositions and methods contemplated herein. An "immune effector cell," is any cell of the immune system that has one or more effector functions (e.g., cytotoxic cell killing activity, secretion of cytokines, induction of ADCC and/or CDC). Illustrative immune effector cells contemplated in particular embodiments are T lymphocytes, in particular cytotoxic T cells (CTLs; CD8$^+$ T cells), TILs, and helper T cells (HTLs; CD4$^+$ T cells). In one embodiment, immune effector cells include natural killer (NK) cells. In one embodiment, immune effector cells include natural killer T (NKT) cells.

"Potent T cells," and "young T cells," are used interchangeably in particular embodiments and refer to T cell phenotypes wherein the T cell is capable of proliferation and a concomitant decrease in differentiation. In particular embodiments, the young T cell has the phenotype of a "naïve T cell." In particular embodiments, young T cells comprise one or more of, or all of the following biological markers: CD62L, CCR7, CD28, CD27, CD122, CD127, CD197, and CD38. In one embodiment, young T cells comprise one or more of, or all of the following biological markers: CD62L, CD127, CD197, and CD38. In one embodiment, the young T cells lack expression of CD57, CD244, CD160, PD-1, CTLA4, and LAG3.

T cells can be obtained from a number of sources including, but not limited to, peripheral blood mononuclear cells, bone marrow, lymph nodes tissue, cord blood, thymus issue, tissue from a site of infection, ascites, pleural effusion, spleen tissue, and tumors.

In particular embodiments, a population of cells comprises immune effector cells or T cells comprising a homing endonuclease variant or megaTAL that targets exon 1 of the constant region of the TCRα gene as contemplated herein.

In particular embodiments, a population of cells comprises immune effector cells or T cells comprising a homing endonuclease variant polypeptide or megaTAL polypeptide that targets exon 1 of the constant region of the TCRα gene as contemplated herein.

In particular embodiments, a population of cells comprises immune effector cells or T cells comprising a vector encoding a homing endonuclease variant or megaTAL that targets exon 1 of the constant region of the TCRα gene as contemplated herein.

In particular embodiments, a population of cells comprises immune effector cells or T cells comprising an mRNA encoding a homing endonuclease variant or megaTAL that targets exon 1 of the constant region of the TCRα gene as contemplated herein.

G. Compositions and Formulations

The compositions contemplated in particular embodiments may comprise one or more polypeptides, polynucleotides, vectors comprising same, and genome editing compositions and genome edited cell compositions, as contemplated herein. The genome editing compositions and methods contemplated in particular embodiments are useful for editing a target site in the human T cell receptor alpha (TCRα) gene in a cell or a population of cells. In preferred embodiments, a genome editing composition is used to edit a TCRα gene in a hematopoietic cell, e.g., a T cell or an immune effector cell.

In various embodiments, the compositions contemplated herein comprise a nuclease variant, and optionally an end-processing enzyme, e.g., a 3'-5' exonuclease (Trex2). The nuclease variant may be in the form of an mRNA that is introduced into a cell via polynucleotide delivery methods disclosed supra, e.g., electroporation, lipid nanoparticles, etc. In one embodiment, a composition comprising an mRNA encoding a homing endonuclease variant or megaTAL, and optionally a 3'-5' exonuclease, is introduced in a cell via polynucleotide delivery methods disclosed supra. The composition may be used to generate a genome edited cell or population of genome edited cells by error prone NHEJ.

In various embodiments, the compositions contemplated herein comprise a donor repair template. The composition may be delivered to a cell that expresses or will express nuclease variant, and optionally an end-processing enzyme. In one embodiment, the composition may be delivered to a cell that expresses or will express a homing endonuclease variant or megaTAL, and optionally a 3'-5' exonuclease. Expression of the gene editing enzymes in the presence of the donor repair template can be used to generate a genome edited cell or population of genome edited cells by HDR.

Compositions include, but are not limited to pharmaceutical compositions. A "pharmaceutical composition" refers to a composition formulated in pharmaceutically-acceptable or physiologically-acceptable solutions for administration to a cell or an animal, either alone, or in combination with one or more other modalities of therapy. It will also be understood that, if desired, the compositions may be administered in combination with other agents as well, such as, e.g., cytokines, growth factors, hormones, small molecules, chemotherapeutics, pro-drugs, drugs, antibodies, or other various pharmaceutically-active agents. There is virtually no limit to other components that may also be included in the compositions, provided that the additional agents do not adversely affect the composition.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "pharmaceutically acceptable carrier" refers to a diluent, adjuvant, excipient, or vehicle with which the therapeutic cells are administered. Illustrative examples of pharmaceutical carriers can be sterile liquids, such as cell culture media, water and oils, including those of petroleum, animal, vegetable or synthetic origin, such as peanut oil, soybean oil, mineral oil, sesame oil and the like. Saline solutions and aqueous dextrose and glycerol solutions can also be employed as liquid carriers, particularly for injectable solutions. Suitable pharmaceutical excipients in particular embodiments, include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Except insofar as any conventional media or agent is incompatible with the active ingredient, its use in the therapeutic compositions is contemplated. Supplementary active ingredients can also be incorporated into the compositions.

In one embodiment, a composition comprising a pharmaceutically acceptable carrier is suitable for administration to a subject. In particular embodiments, a composition comprising a carrier is suitable for parenteral administration, e.g., intravascular (intravenous or intraarterial), intraperitoneal or intramuscular administration. In particular embodiments, a composition comprising a pharmaceutically acceptable carrier is suitable for intraventricular, intraspinal, or intrathecal administration. Pharmaceutically acceptable carriers include sterile aqueous solutions, cell culture media, or dispersions. The use of such media and agents for pharmaceutically active substances is well known in the art. Except insofar as any conventional media or agent is incompatible with the transduced cells, use thereof in the pharmaceutical compositions is contemplated.

In particular embodiments, compositions contemplated herein comprise genetically modified T cells and a pharmaceutically acceptable carrier. A composition comprising a cell-based composition contemplated herein can be administered separately by enteral or parenteral administration methods or in combination with other suitable compounds to effect the desired treatment goals.

The pharmaceutically acceptable carrier must be of sufficiently high purity and of sufficiently low toxicity to render it suitable for administration to the human subject being treated. It further should maintain or increase the stability of the composition. The pharmaceutically acceptable carrier can be liquid or solid and is selected, with the planned manner of administration in mind, to provide for the desired bulk, consistency, etc., when combined with other components of the composition. For example, the pharmaceutically acceptable carrier can be, without limitation, a binding agent (e.g., pregelatinized maize starch, polyvinylpyrrolidone or hydroxypropyl methylcellulose, etc.), a filler (e.g., lactose and other sugars, microcrystalline cellulose, pectin, gelatin, calcium sulfate, ethyl cellulose, polyacrylates, calcium hydrogen phosphate, etc.), a lubricant (e.g., magnesium stearate, talc, silica, colloidal silicon dioxide, stearic acid, metallic stearates, hydrogenated vegetable oils, corn starch, polyethylene glycols, sodium benzoate, sodium acetate, etc.), a disintegrant (e.g., starch, sodium starch glycolate, etc.), or a wetting agent (e.g., sodium lauryl sulfate, etc.). Other suitable pharmaceutically acceptable carriers for the compositions contemplated herein include, but are not limited to, water, salt solutions, alcohols, polyethylene glycols, gelatins, amyloses, magnesium stearates, talcs, silicic acids, viscous paraffins, hydroxymethylcelluloses, polyvinylpyrrolidones and the like.

Such carrier solutions also can contain buffers, diluents and other suitable additives. The term "buffer" as used herein refers to a solution or liquid whose chemical makeup neutralizes acids or bases without a significant change in pH. Examples of buffers contemplated herein include, but are not limited to, Dulbecco's phosphate buffered saline (PBS), Ringer's solution, 5% dextrose in water (D5W), normal/physiologic saline (0.9% NaCl).

The pharmaceutically acceptable carriers may be present in amounts sufficient to maintain a pH of the composition of about 7. Alternatively, the composition has a pH in a range from about 6.8 to about 7.4, e.g., 6.8, 6.9, 7.0, 7.1, 7.2, 7.3, and 7.4. In still another embodiment, the composition has a pH of about 7.4.

Compositions contemplated herein may comprise a non-toxic pharmaceutically acceptable medium. The compositions may be a suspension. The term "suspension" as used herein refers to non-adherent conditions in which cells are not attached to a solid support. For example, cells maintained as a suspension may be stirred or agitated and are not adhered to a support, such as a culture dish.

In particular embodiments, compositions contemplated herein are formulated in a suspension, where the genome edited T cells are dispersed within an acceptable liquid medium or solution, e.g., saline or serum-free medium, in an intravenous (IV) bag or the like. Acceptable diluents include, but are not limited to water, PlasmaLyte, Ringer's solution, isotonic sodium chloride (saline) solution, serum-free cell culture medium, and medium suitable for cryogenic storage, e.g., Cryostor® medium.

In certain embodiments, a pharmaceutically acceptable carrier is substantially free of natural proteins of human or animal origin, and suitable for storing a composition comprising a population of genome edited T cells. The therapeutic composition is intended to be administered into a human patient, and thus is substantially free of cell culture components such as bovine serum albumin, horse serum, and fetal bovine serum.

In some embodiments, compositions are formulated in a pharmaceutically acceptable cell culture medium. Such compositions are suitable for administration to human subjects. In particular embodiments, the pharmaceutically acceptable cell culture medium is a serum free medium.

Serum-free medium has several advantages over serum containing medium, including a simplified and better defined composition, a reduced degree of contaminants, elimination of a potential source of infectious agents, and lower cost. In various embodiments, the serum-free medium is animal-free, and may optionally be protein-free. Optionally, the medium may contain biopharmaceutically acceptable recombinant proteins. "Animal-free" medium refers to medium wherein the components are derived from non-animal sources. Recombinant proteins replace native animal proteins in animal-free medium and the nutrients are obtained from synthetic, plant or microbial sources. "Protein-free" medium, in contrast, is defined as substantially free of protein.

Illustrative examples of serum-free media used in particular compositions includes, but is not limited to QBSF-60 (Quality Biological, Inc.), StemPro-34 (Life Technologies), and X-VIVO 10.

In a preferred embodiment, the compositions comprising genome edited T cells are formulated in PlasmaLyte.

In various embodiments, compositions comprising genome edited T cells are formulated in a cryopreservation medium. For example, cryopreservation media with cryopreservation agents may be used to maintain a high cell viability outcome post-thaw. Illustrative examples of cryopreservation media used in particular compositions includes, but is not limited to, CryoStor CS10, CryoStor CS5, and CryoStor CS2.

In one embodiment, the compositions are formulated in a solution comprising 50:50 PlasmaLyte A to CryoStor CS10.

In particular embodiments, the composition is substantially free of *mycoplasma*, endotoxin, and microbial contamination. By "substantially free" with respect to endotoxin is meant that there is less endotoxin per dose of cells than is allowed by the FDA for a biologic, which is a total endotoxin of 5 EU/kg body weight per day, which for an average 70 kg person is 350 EU per total dose of cells. In particular embodiments, compositions comprising hematopoietic stem or progenitor cells transduced with a retroviral vector contemplated herein contain about 0.5 EU/mL to about 5.0 EU/mL, or about 0.5 EU/mL, 1.0 EU/mL, 1.5 EU/mL, 2.0 EU/mL, 2.5 EU/mL, 3.0 EU/mL, 3.5 EU/mL, 4.0 EU/mL, 4.5 EU/mL, or 5.0 EU/mL.

In certain embodiments, compositions and formulations suitable for the delivery of polynucleotides are contemplated including, but not limited to, one or more mRNAs encoding one or more reprogrammed nucleases, and optionally end-processing enzymes.

Exemplary formulations for ex vivo delivery may also include the use of various transfection agents known in the art, such as calcium phosphate, electroporation, heat shock and various liposome formulations (i.e., lipid-mediated transfection). Liposomes, as described in greater detail below, are lipid bilayers entrapping a fraction of aqueous fluid. DNA spontaneously associates to the external surface of cationic liposomes (by virtue of its charge) and these liposomes will interact with the cell membrane.

In particular embodiments, formulation of pharmaceutically-acceptable carrier solutions is well-known to those of skill in the art, as is the development of suitable dosing and treatment regimens for using the particular compositions described herein in a variety of treatment regimens, including e.g., enteral and parenteral, e.g., intravascular, intravenous, intrarterial, intraosseously, intraventricular, intracerebral, intracranial, intraspinal, intrathecal, and intramedullary administration and formulation. It would be understood by the skilled artisan that particular embodiments contemplated herein may comprise other formulations, such as those that are well known in the pharmaceutical art, and are described, for example, in Remington: *The Science and Practice of Pharmacy*, volume I and volume II. $22^{nd}$ Edition. Edited by Loyd V. Allen Jr. Philadelphia, Pa.: Pharmaceutical Press; 2012, which is incorporated by reference herein, in its entirety.

All publications, patent applications, and issued patents cited in this specification are herein incorporated by reference as if each individual publication, patent application, or issued patent were specifically and individually indicated to be incorporated by reference.

Although the foregoing embodiments have been described in some detail by way of illustration and example for purposes of clarity of understanding, it will be readily apparent to one of ordinary skill in the art in light of the teachings contemplated herein that certain changes and modifications may be made thereto without departing from the spirit or scope of the appended claims. The following examples are provided by way of illustration only and not by way of limitation. Those of skill in the art will readily recognize a variety of noncritical parameters that could be changed or modified to yield essentially similar results.

EXAMPLES

Example 1

Improving Selectivity of an I-OnuI Variant that Targets the Human TCRα Gene

Regions of sub-optimal selectivity were identified in the DNA recognition interfacing regions of an I-OnuI variant (SEQ ID NO: 6) that targets exon 1 in the constant region of the human TCRα gene ("the original TCRα I-OnuI variant"). Positions p4, p5, and p6 in the target site were found to be relatively tolerant to base pair substitutions. The nucleotides differ at these positions in the TCRα on-target site (CCG at p456) (SEQ ID NO: 17) and a frequent off-target site in intron 6 of the KAT2B gene (ACA at p456, see Osborne et. al., 2015) (FIG. 1, SEQ ID NO: 21). An I-OnuI variant comprising a domain with enhanced selectivity at these positions was developed to improve overall selectivity properties as well as a specific reduction of activity at the KAT2B off-target site (SEQ ID NO: 21).

Inspection of the crystal structure of the wild-type I-OnuI protein (e.g., SEQ ID NOs: 1-5) complexed with its natural target site identified a subset of 8 amino acid residues that are likely contacting or proximal to positions p456. Local analysis of another I-OnuI variant that targets the human TCRα gene identified amino acids that have significantly greater selectivity for CCG in comparison with the original TCRα targeting I-OnuI variant. The amino acids responsible for high CCG triplet selectivity in the TCRα targeting I-OnuI variant were inserted into the original TCRα I-OnuI variant to generated the TCRα2.0 I-OnuI variant (SEQ ID NO: 7) (FIG. 2). TCRα2.0 I-OnuI variant enzymatic activity was assessed against all 64-nucleotide combinations at the p456 substrate positions using yeast surface display (FIG. 3A-FIG. 3I). The TCRα2.0 I-OnuI variant exhibited significantly better substrate discrimination, marked by cleaving far fewer substrates than the original TCRα I-OnuI variant.

Example 2

Improving Catalytic Activity of an TCRα 2.0 MegaTAL

Disruption of the TCRα locus prevents trafficking of CD3 to the cell surface. CD3 expression can be measured using fluorescently labeled anti-CD3 antibody and flow cytometry. Gene editing efficiency is inversely proportional to CD3 fluorescence.

Figure 4:
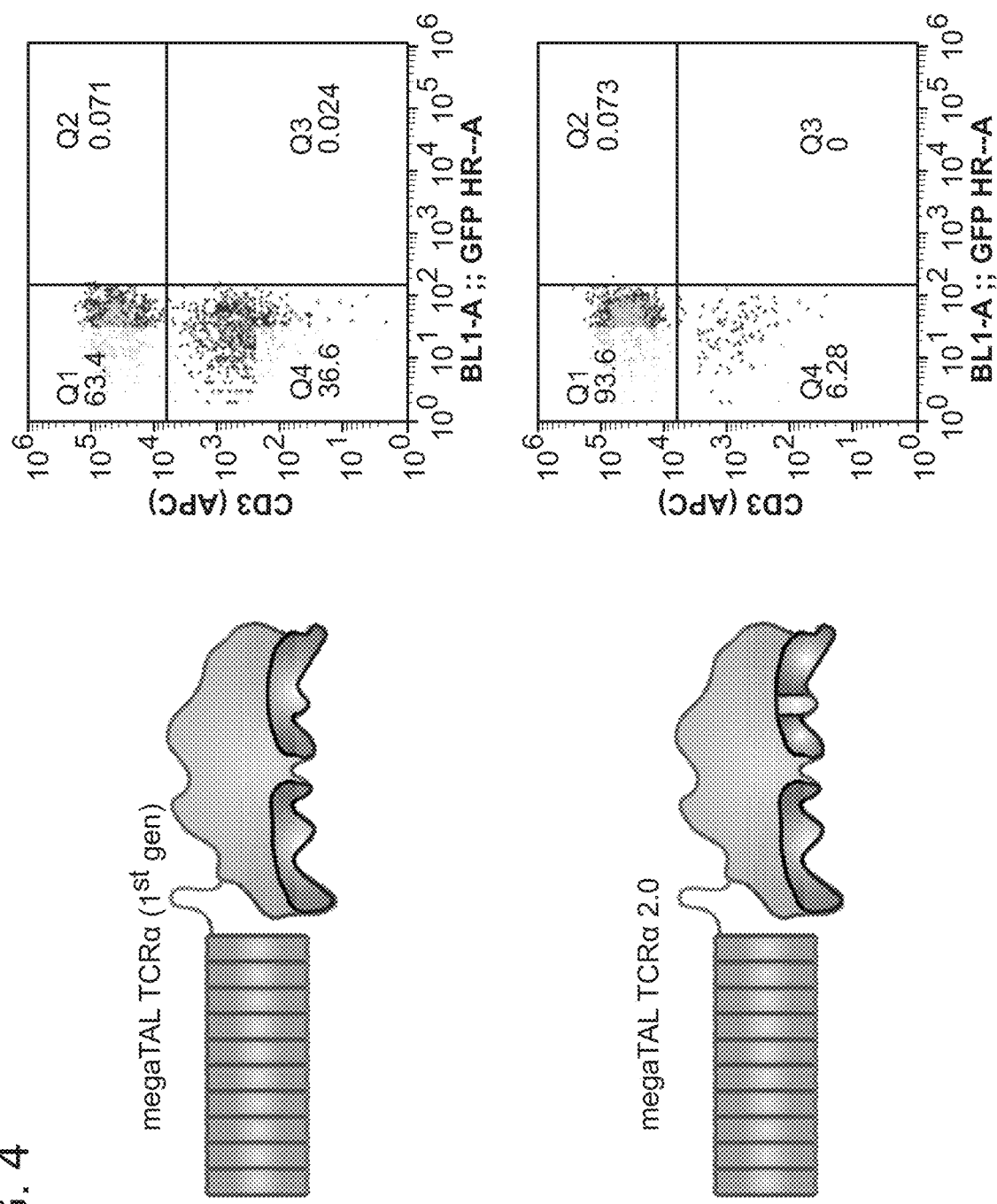
FIG. 4 shows representative data of gene editing efficiency at the TCRα locus using CD3 surface expression as a readout. A first generation TCRα megaTAL (A) (SEQ ID NO: 6) shows increased gene editing efficiency in human primary T cells compared to T cells treated with a TCRα2.0 megaTAL (SEQ ID NO: 7).

Primary human T cells were activated with CD3 and CD28, and electroporated with in vitro transcribed mRNA encoding either the original TCRα HE variant formatted as a megaTAL (e.g., SEQ ID NO: 13) or the TCRα2.0 HE variant formatted as a megaTAL (e.g., SEQ ID NO: 14). Despite displaying significantly enhanced selectivity at the p456 substrate positions, the TCRα2.0 megaTAL displayed reduced catalytic activity, indicated by increased CD3 expression compared to the original TCRα megaTAL (FIG. 4). Genomic DNA was subsequently isolated from megaTAL treated cells and the reduced catalytic activity was confirmed using PCR coupled with Tracking of Indels by DEcomposition (TIDE, see Brinkman et al., 2014) at the target site.

Figure 5:
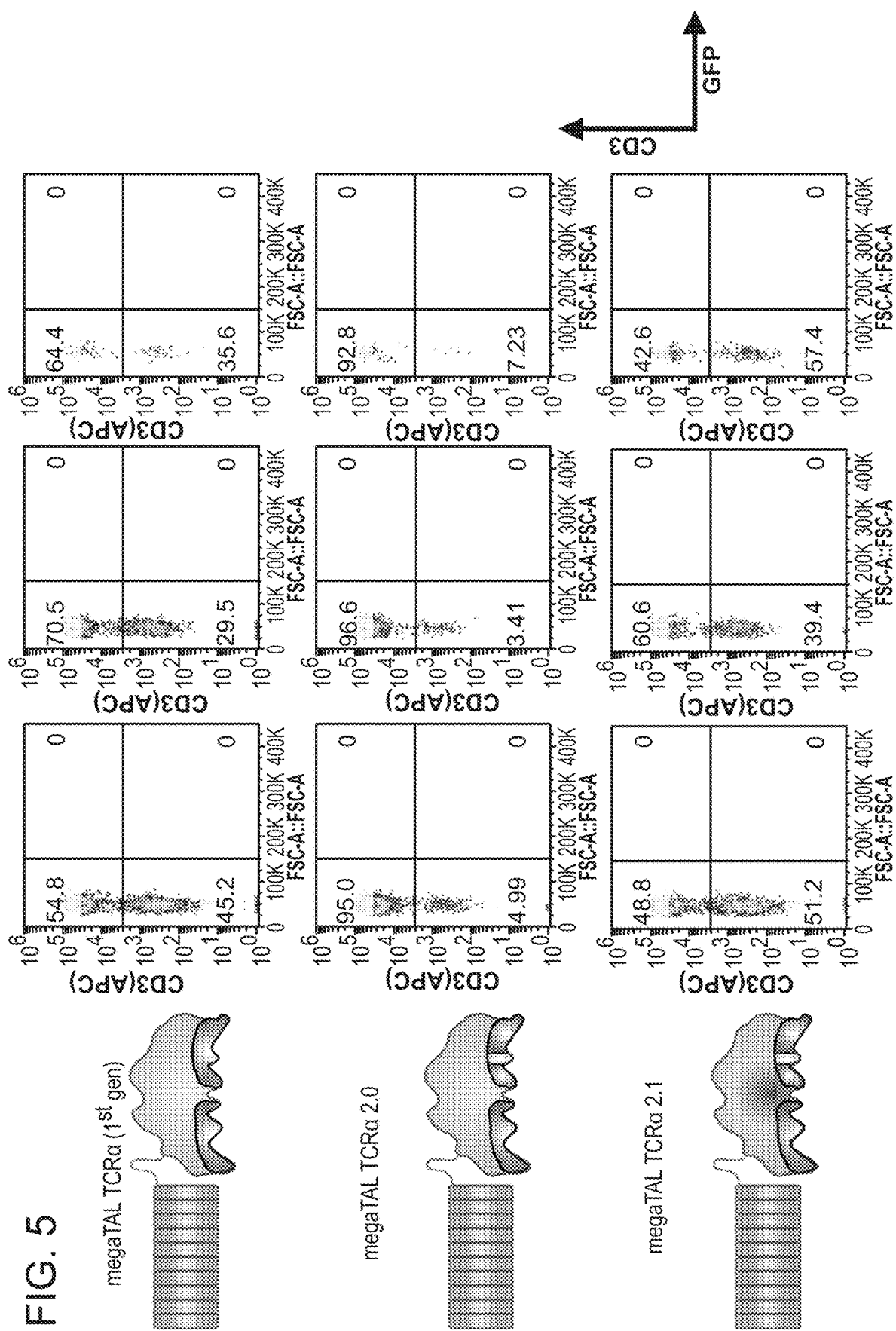
FIG. 5 shows that introduction of the targeted mutation (E178D) in the TCRα2.0 megaTAL (B) to generate the TCRα2.1 megaTAL (C) (SEQ ID NO: 8) restores on-target cleavage activity of the first generation TCRα megaTAL (A) while retaining the on-target selectivity of the TCRα2.0 megaTAL.
Figure 6A:
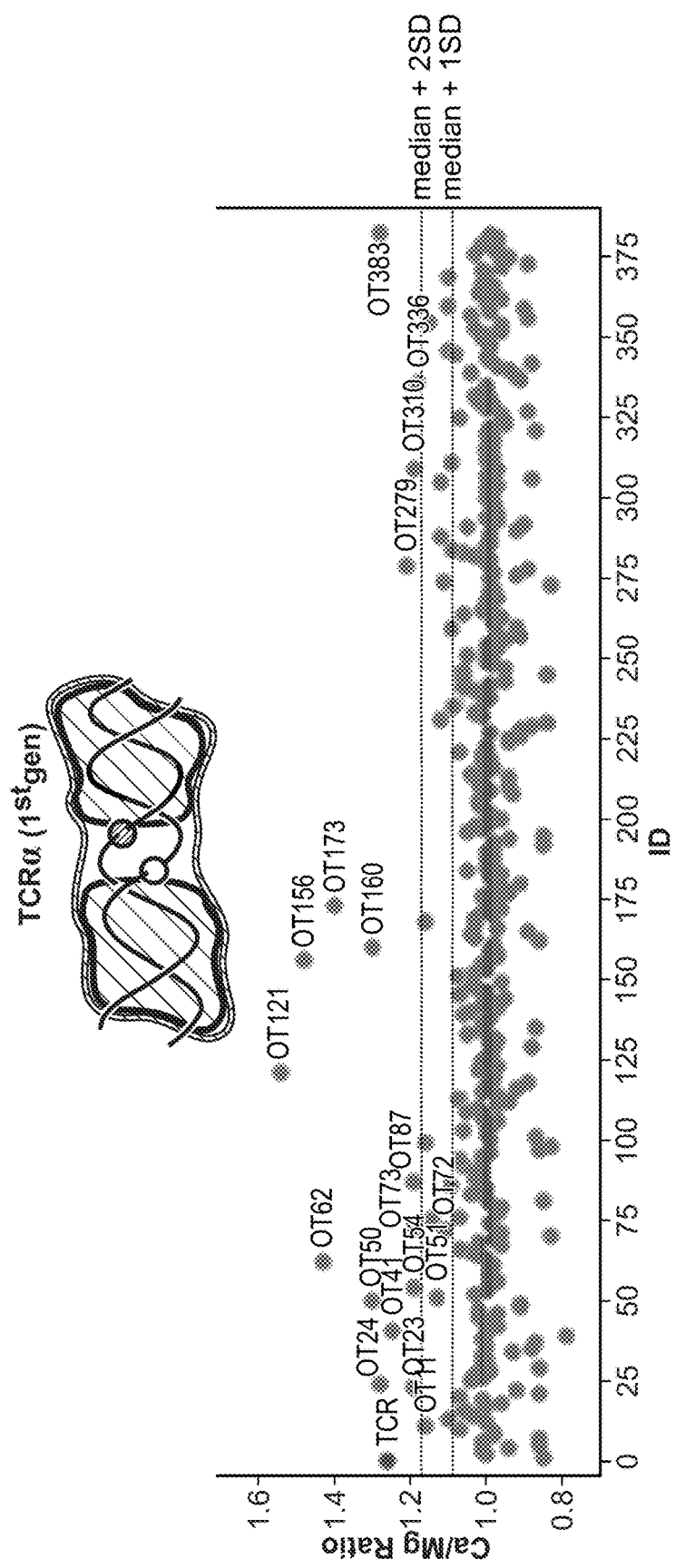
FIG. 6A to FIG. 6F shows the increased selectivity of the TCRα2.1 megaTAL by yeast-surface-display profiling using bioinformatically derived putative off-target sites.
Figure 6B:
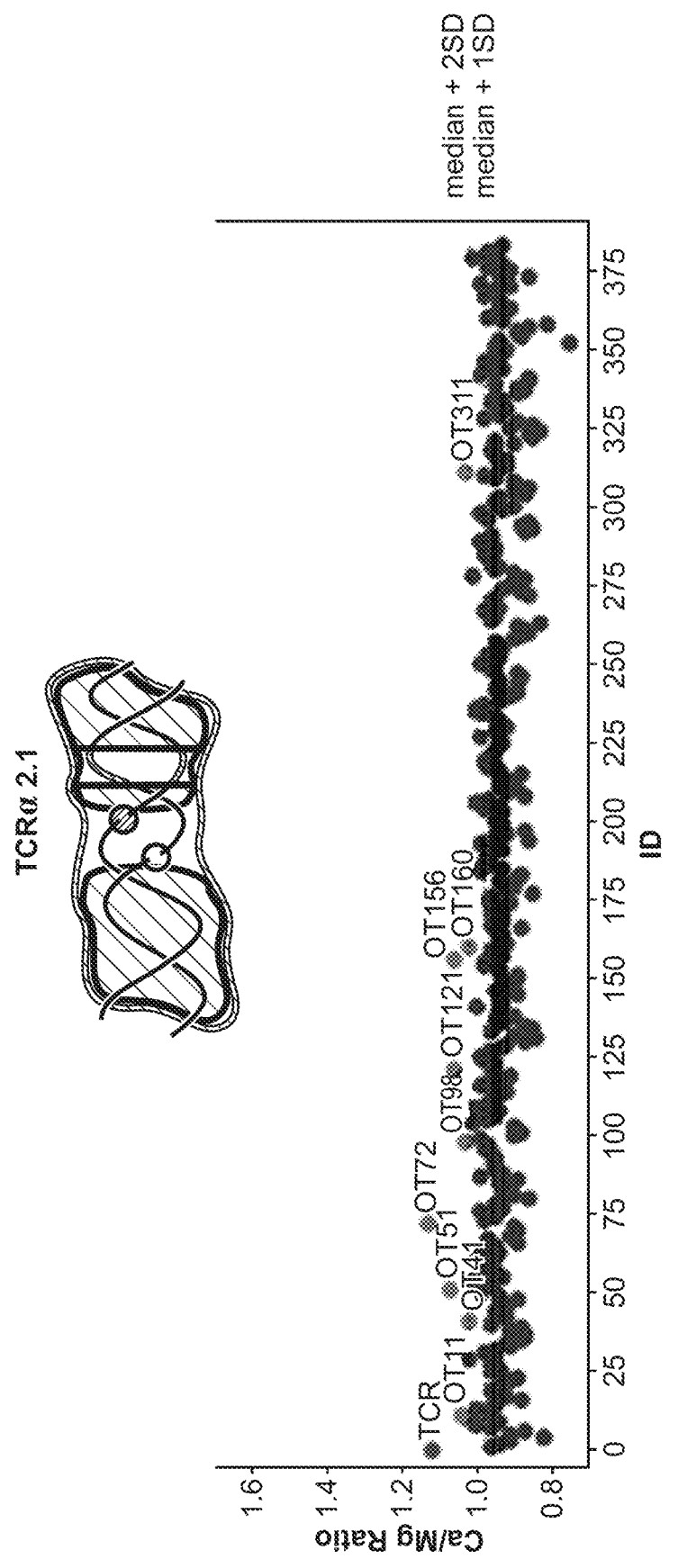
Figure 6C:
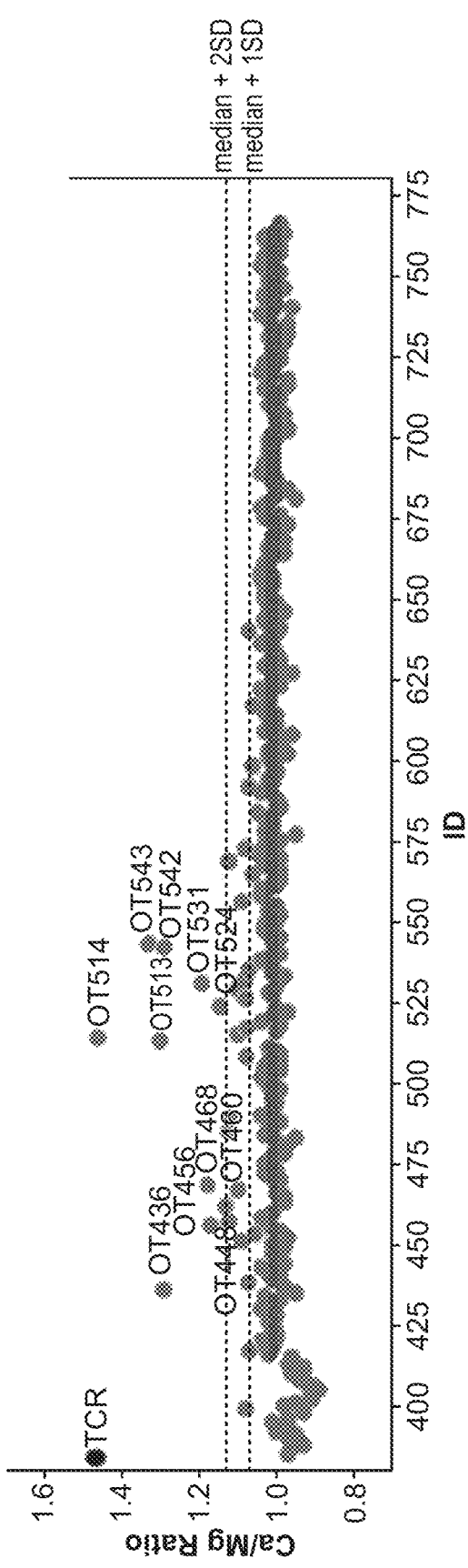
Figure 6D:
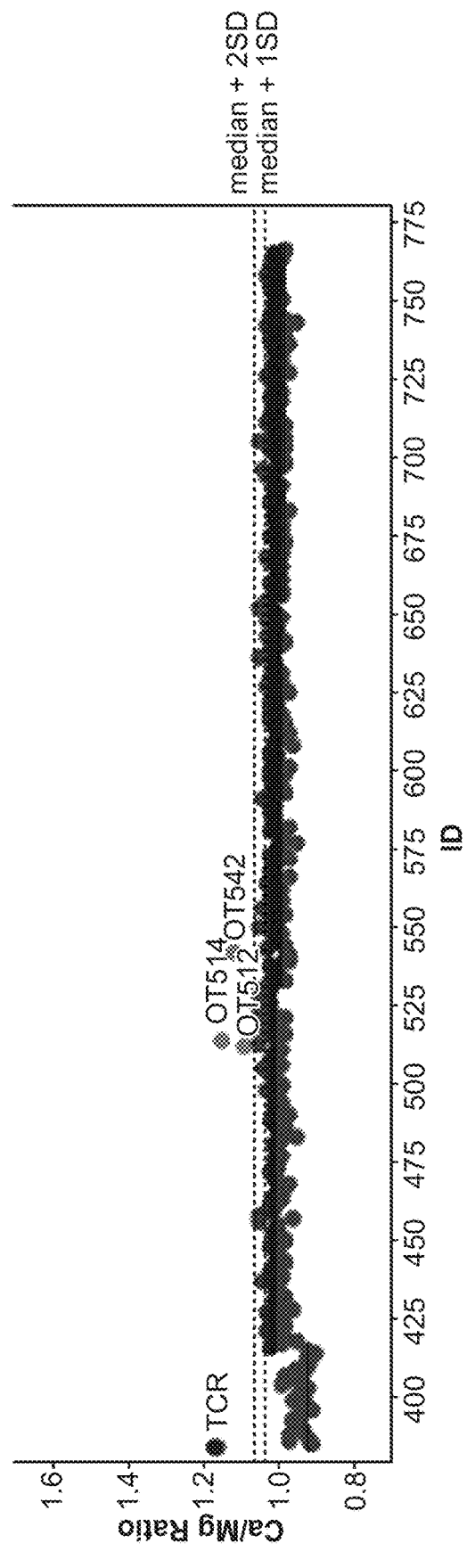
Figure 6E:
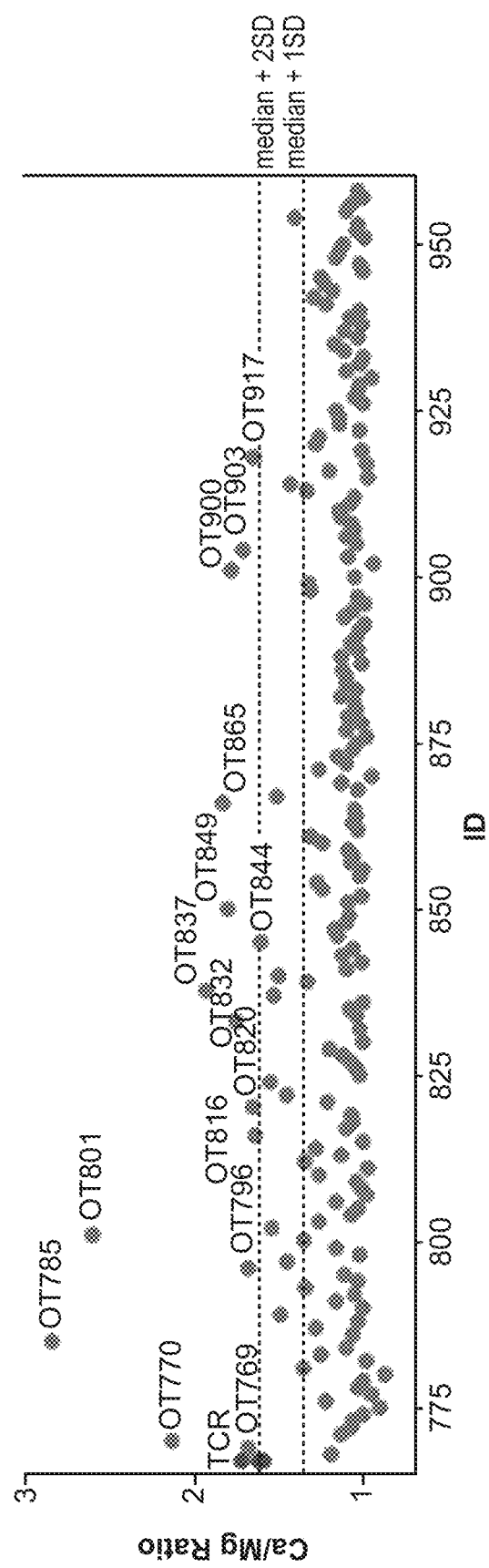
Figure 6F:
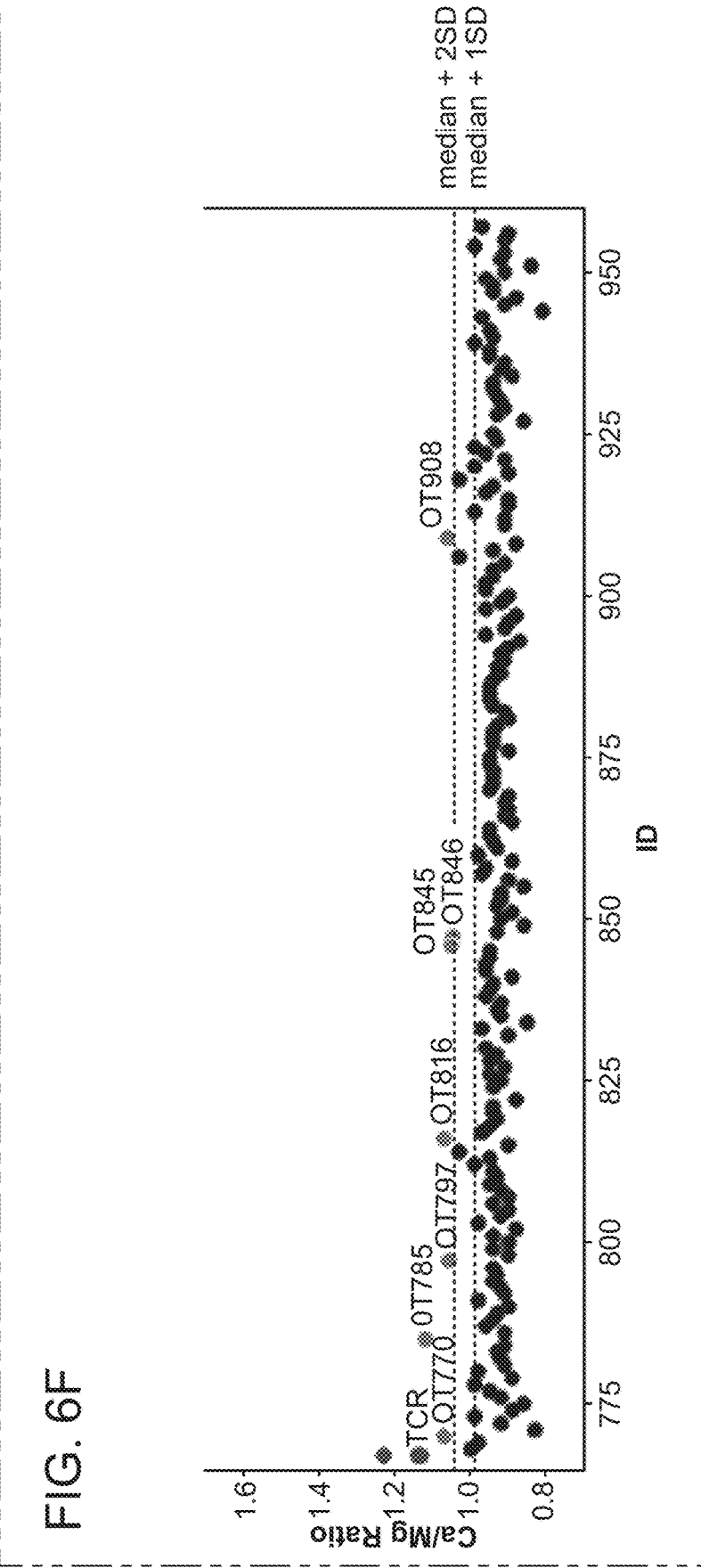

A single amino acid substitution, E178D, that increased catalytic activity in another I-OnuI variant was inserted at the active site of the TCRα2.0 megaTAL to generate the TCRα2.1 megaTAL (SEQ ID NO: 8). In vitro transcribed mRNA encoding the TCRα2.1 megaTAL (e.g., SEQ ID NO: 15) was electroporated into primary human T cells. The TCRα2.1 megaTAL increased CD3 knockdown 10-fold compared to the TCRα2.0 megaTAL. FIG. 5.

Example 3

The TCRα2.1 I-OnuI Variant and TCRα2.1 MegaTAL Show Enhanced on- to Off-Target Discrimination Therapeutic genome editing carries a degree of risk attributed to very low frequency off-target editing events. Genome editing enzymes can be characterized in depth for off-target editing events using existing methods (see Tsai et al. 2016).

Potential off-target sites were identified using bioinformatic algorithms that scan the human genome for 22-bp sequences resembling the TCRα target sequence (SEQ ID NO: 17). The top 764 22-bp sequences returned from the bioinformatics search were assayed individually for cleavage by the original TCRα HE variant and the TCRα2.1 HE variant using yeast surface display. The TCRα2.1 HE variant displayed increased selectivity for the TCRα target sequence compared to the original TCRα HE variant (FIG. 6A-FIG. 6F), consistent with results obtained in Example 1.

A second bioinformatics search was conducted using the sequence information of the top 50 cleaved substrates from the 764 substrate panel to further inform the search. These were assayed individually for cleavage by the original TCRα and TCRα2.1 HE variants. The refined TCRα2.1 HE variant displayed an enhanced selectivity profile compared to the original TCRα HE variant.

A second assay employing integrase deficient lentiviral vectors (IDLV, see Gabriel 2011) was used to identify additional off-target sites generated in vivo. Briefly, IDLV is captured at the site of double strand breaks within enzyme treated and mock treated cells. The frequency and location of IDLV integration can then be mapped and compared between the two populations. Increased IDLV uptake frequency at a particular genomic site in enzyme treated samples compared to mock treated samples indicates enzymatic cleavage. A primary off-target site of the original TCRα megaTAL was identified in intron six of the KAT2B gene (SEQ ID NO: 21, Osborne et al. 2015) using this method.

Figure 7:
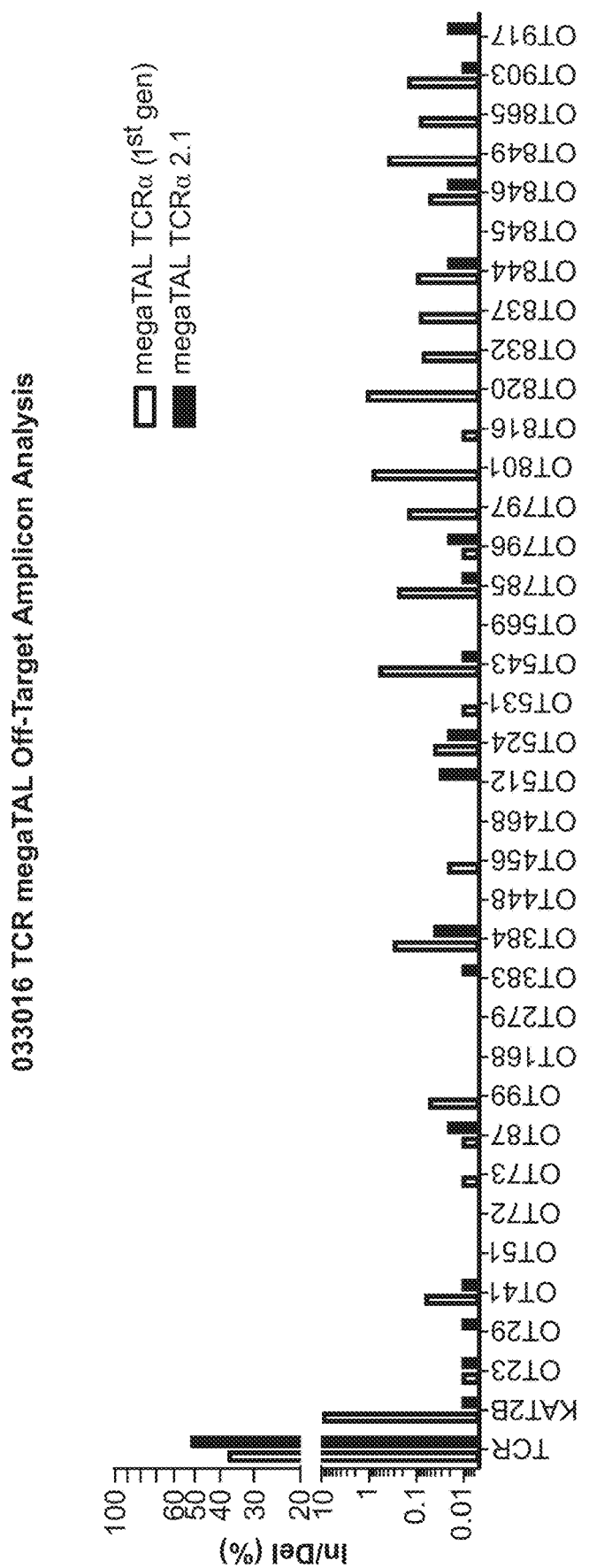
FIG. 7 shows the increased selectivity of the TCRα2.1 megaTAL by deep sequencing of amplicons generated from genomic DNA of megaTAL treated primary T cells.

The putative off-target sites identified were evaluated by deep sequencing of amplicons generated from megaTAL treated donor derived primary T cells (FIG. 7). The TCRα2.1 megaTAL eliminated off-target editing at the KAT2B gene locus and displayed enhanced selectivity for the on-target site, with reduced activity at the potential off-target sites compared to the original TCRα megaTAL.

Example 4

Extension of the TAL DNA Binding Domain Increases TCRα Genome Editing

MegaTALs include TALE DNA binding domain fusions to the meganuclease architecture to increase binding affinity, or addressing, toward the desired target sequence (see Boissel et al. 2013). To further increase on-target editing efficiency at the TCRα locus an additional TALE RVD was appended to the C-terminal end the TALE DNA binding domain to increase the total length of the TALE DNA binding domain array from 10.5 to 11.5 RVD repeats and generate the 11.5 RVD TCRα 2.1 megaTAL (e.g., SEQ ID NO: 12). The 11.5 RVD TALE DNA binding domain recognizes the original TALE binding site (SEQ ID NO: 18) with an additional nucleotide on the 3' end (SEQ ID NO: 19).

Figure 8A:
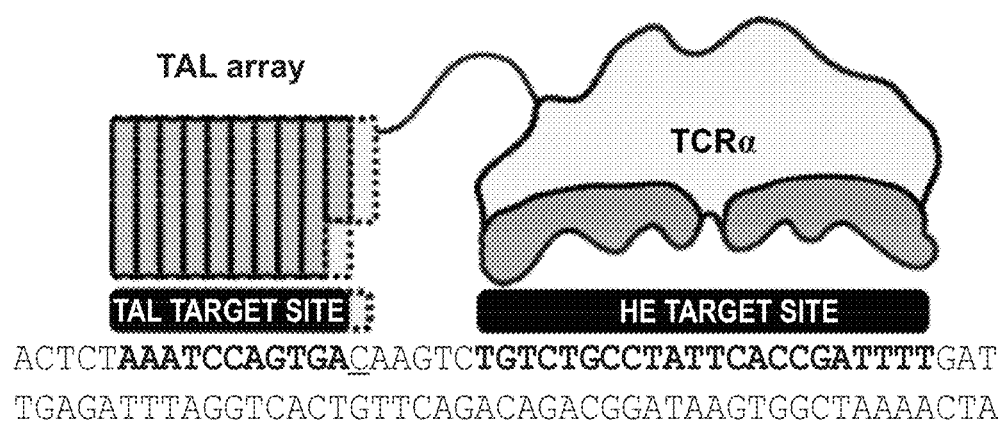
FIG. 8A and FIG. 8B shows that appending an additional TALE RVD to the TCRα2.1 megaTAL to increase the TALE repeats from 10.5 to 11.5 (A) further increases on-target activity (SEQ ID NOS: 68 and 69) of the TCRα2.1 megaTAL in primary T cells (B).
Figure 8B:
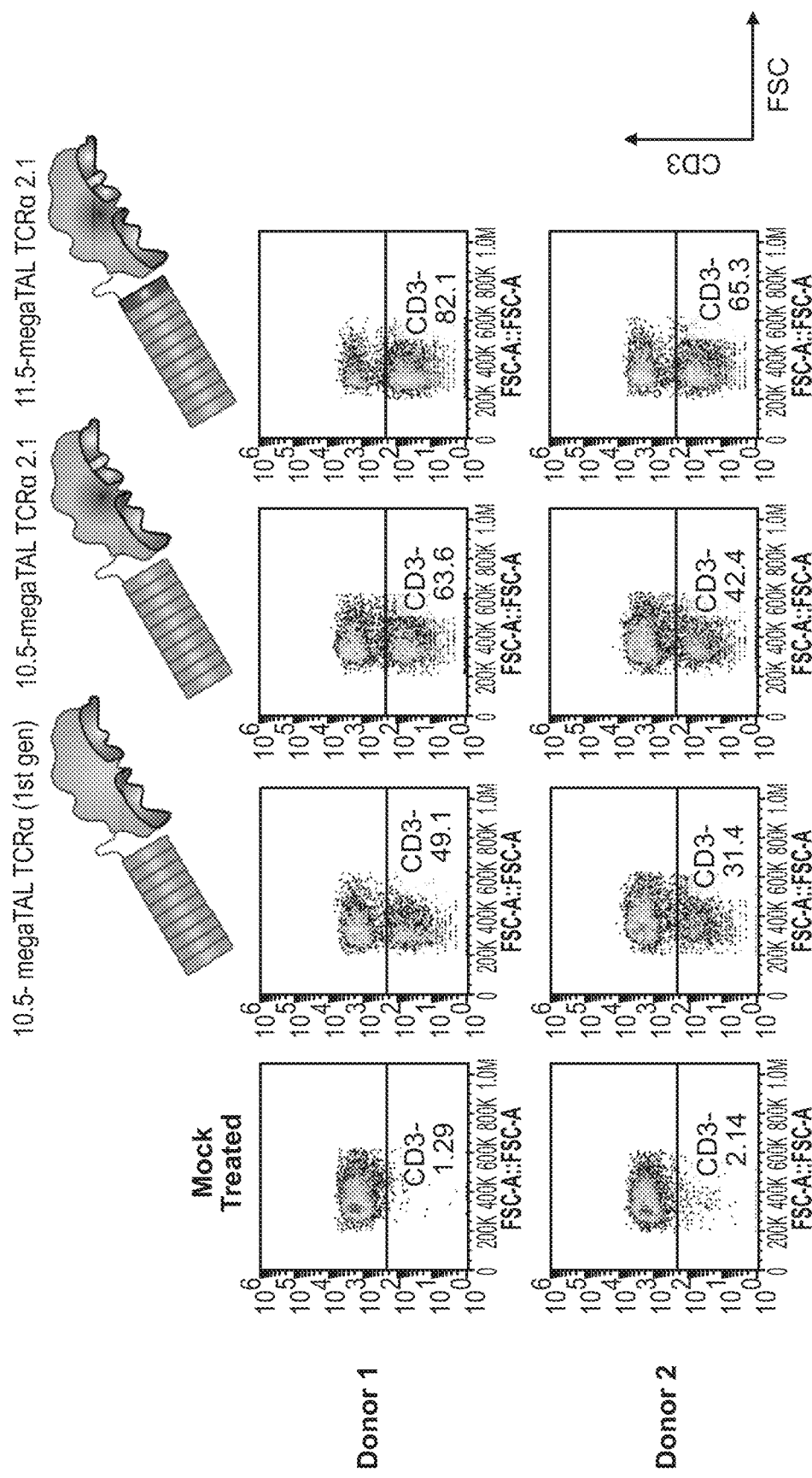
Figure 9:
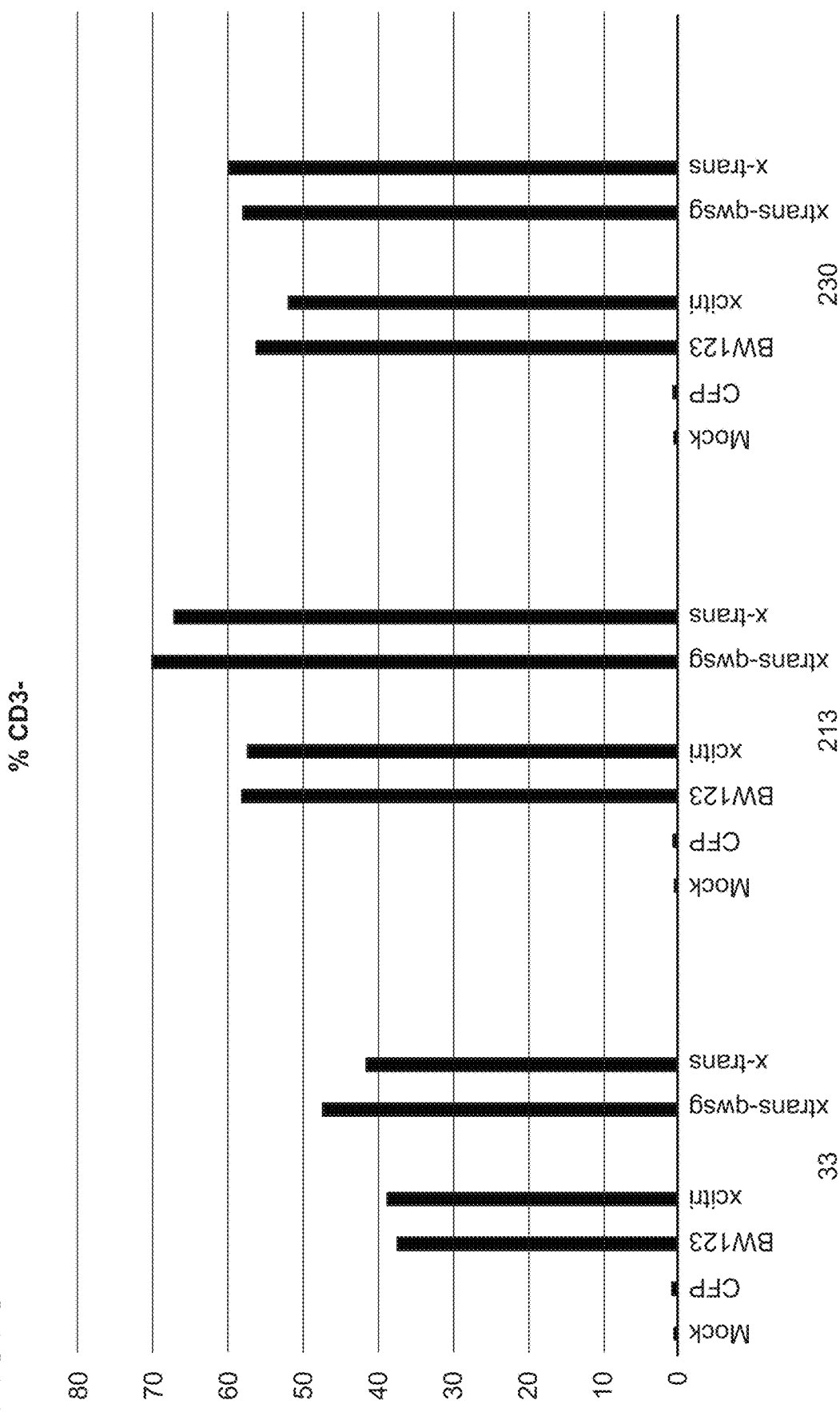
FIG. 9 shows that appending rationally designed minimal N-terminal TAL domains derived from different *Xanthomonas* family members yields similar or, in some instances, a modest increase in activity compared to the first generation TCRα megaTAL containing an *X oryzae* N-terminal TAL domain.

Human primary T cells were electroporated with in vitro transcribed mRNA encoding the 10.5 RVD and 11.5 RVD TCRα2.1 megaTALs. The 11.5 RVD TCRα2.1 megaTAL increased TCRα editing 30-50%, as measured by CD3 knockdown using flow cytometry, compared to TCRα editing with the 10.5 RVD TCRα2.1 megaTAL (FIG. 8B).

Example 5

Variant N-Terminal Tale Architectures

MegaTALs are hybrid nucleases that include homing endonuclease fused to a TAL effector (TALE) architecture comprising an N-terminal domain, a DNA binding domain, and a C-terminal domain. Some TALE architectures comprise a minimal N-terminal region (delta-154') of approximately 136 amino acids, a variable number of 34 amino acid RVD-containing repeats (terminating with a truncated 20 amino acid repeat), and a minimal C-terminal region of approximately 63 amino acids.

The TALE architecture fused to the homing endonuclease described in the previous examples includes sequences derived from the *Xanthomonas oryzae* TALE proteins. In addition to the *X oryzae* TALE domain sequences, minimal N-terminal TALE domain (NTD) regions can be derived from other members of *Xanthomonas* family such as *Xanthomonas translucens* and *Xanthomonas citri*. Multiple sequence alignments of N-terminal TALE domains showed that the X *Oryzae* shares 85% and 87% sequence similarity with *X translucens* and X *citri*, respectively. To assess if TAL activity could be further enhanced using alternative species NTDs, hybrid NTDs were generated by rationally substituting and combining the following amino acid positions in endogenous *X translucens* and X *citri* sequences: V152G, D153K, D165E, E166K, I167L, P169L, A173P, T174I, Q180E, M183I, H191Q, V205I, V207A, I224V, V227I, A236V, G249S, G257S, V271I (e.g., SEQ ID NO:21); V152G, D153K, T170K, V171A, V183I, A200P, A236T, A239V, A244V, E245Q, G257S, L260V, V271I, (e.g., SEQ ID NO:24); T170K, A200P, Q230H, W231C, S232G, A236T, A239V, A244V, E245Q, G257S (e.g., SEQ ID NO: 23). The hybrid sequences (e.g., SEQ ID NOs: 22, 23, 24) showed 80% similarity to X *Oryzae* N-terminal TAL domain. Each of these minimal TALE domains was individually grafted onto the N-terminus of the TALE DNA binding domain of the original TCRα I-OnuI variant megaTAL. In vitro transcribed mRNAs encoding the variant megaTALs comprising TALE N-terminal domain (NTD) variants or *X oryzae* NTDs were electroporated into human primary T cells to assess editing rates at the TCRα locus. Flow cytometric analysis of CD3 expression demonstrated that the TCRα megaTALs comprising NTD variant domains showed similar activity, and in some cases slightly higher activity, relative to the original TCRα megaTAL comprising *X oryzae* NTD (FIG. 9).

In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. A polypeptide comprising an I-OnuI homing endonuclease (HE) variant that cleaves a target site in the human T cell receptor alpha (TCRα) gene, wherein the I-OnuI HE variant comprises an amino acid sequence that is at least 99% identical to the amino acid sequence set forth in SEQ ID NO: 7 or SEQ ID NO: 8.

2. The polypeptide of claim 1, wherein the I-OnuI HE variant comprises the amino acid sequence set forth in SEQ ID NO: 7 or SEQ ID NO: 8.

3. The polypeptide of claim 1, wherein the polypeptide binds and cleaves said TCRα gene at the polynucleotide sequence set forth in SEQ ID NO: 17.

4. The polypeptide of claim 1, further comprising a TALE DNA binding domain.

5. The polypeptide of claim 4, wherein the TALE DNA binding domain comprises 11.5 TALE repeat units, and wherein the TALE DNA binding domain binds the polynucleotide sequence set forth in SEQ ID NO: 19.

6. The polypeptide of claim 4, wherein the TALE DNA binding domain comprises 10.5 TALE repeat units, and wherein the TALE DNA binding domain binds the polynucleotide sequence set forth in SEQ ID NO: 18.

7. The polypeptide of claim 4, wherein the polypeptide binds and cleaves said TCRα gene at the polynucleotide sequence set forth in SEQ ID NO: 20.

8. The polypeptide of claim 1 or claim 4, further comprising:

(a) a peptide linker or a viral self-cleaving 2A peptide; and
(b) a 3'-5' exonuclease.

9. The polypeptide of claim 8, wherein the 3'-5' exonuclease is Trex2.

10. A polypeptide, comprising an I-OnuI homing endonuclease (HE) variant that cleaves a target site in the human T cell receptor alpha (TCRα) gene and further comprising a TALE DNA binding domain, wherein the polypeptide comprises an amino acid sequence set forth in SEQ ID NO: 10 or an amino acid sequence that is at least 99% identical to the amino acid sequence set forth in SEQ ID NO: 12.

11. The polypeptide of claim 4, wherein the polypeptide comprises the amino acid sequence set forth in SEQ ID NO: 10 or SEQ ID NO: 12.

12. A polynucleotide comprising a nucleotide sequence encoding a polypeptide comprising an I-OnuI homing endonuclease (HE) variant that cleaves a target site in the human T cell receptor alpha (TCRα) gene, wherein the I-OnuI HE variant comprises an amino acid sequence that is at least 99% identical to the amino acid sequence set forth in SEQ ID NO: 7 or SEQ ID NO: 8.

13. A vector comprising the polynucleotide of claim 12.

14. A cell comprising the polynucleotide of claim 12.

15. The polynucleotide of claim 12, wherein the nucleotide sequence encoding the polypeptide further comprises a nucleotide sequence encoding a TALE DNA binding domain.

* * * * *

SEQUENCE LISTING

<160> NUMBER OF SEQ ID NOS: 69

<210> SEQ ID NO 1
<211> LENGTH: 303
<212> TYPE: PRT
<213> ORGANISM: Ophiostoma novo-ulmi subsp. americana (mitochondrion)

<400> SEQUENCE: 1

Met Ala Tyr Met Ser Arg Arg Glu Ser Ile Asn Pro Trp Ile Leu Thr
1 5 10 15

Gly Phe Ala Asp Ala Glu Gly Ser Phe Leu Leu Arg Ile Arg Asn Asn
20 25 30

Asn Lys Ser Ser Val Gly Tyr Ser Thr Glu Leu Gly Phe Gln Ile Thr
35 40 45

Leu His Asn Lys Asp Lys Ser Ile Leu Glu Asn Ile Gln Ser Thr Trp
50 55 60

Lys Val Gly Val Ile Ala Asn Ser Gly Asp Asn Ala Val Ser Leu Lys
65 70 75 80

Val Thr Arg Phe Glu Asp Leu Lys Val Ile Ile Asp His Phe Glu Lys
85 90 95

Tyr Pro Leu Ile Thr Gln Lys Leu Gly Asp Tyr Met Leu Phe Lys Gln
100 105 110

Ala Phe Cys Val Met Glu Asn Lys Glu His Leu Lys Ile Asn Gly Ile

```
                    115                 120                 125
Lys Glu Leu Val Arg Ile Lys Ala Lys Leu Asn Trp Gly Leu Thr Asp
            130                 135                 140
Glu Leu Lys Lys Ala Phe Pro Glu Ile Ile Ser Lys Glu Arg Ser Leu
145                 150                 155                 160
Ile Asn Lys Asn Ile Pro Asn Phe Lys Trp Leu Ala Gly Phe Thr Ser
                165                 170                 175
Gly Glu Gly Cys Phe Phe Val Asn Leu Ile Lys Ser Lys Ser Lys Leu
            180                 185                 190
Gly Val Gln Val Gln Leu Val Phe Ser Ile Thr Gln His Ile Lys Asp
                195                 200                 205
Lys Asn Leu Met Asn Ser Leu Ile Thr Tyr Leu Gly Cys Gly Tyr Ile
            210                 215                 220
Lys Glu Lys Asn Lys Ser Glu Phe Ser Trp Leu Asp Phe Val Val Thr
225                 230                 235                 240
Lys Phe Ser Asp Ile Asn Asp Lys Ile Ile Pro Val Phe Gln Glu Asn
                245                 250                 255
Thr Leu Ile Gly Val Lys Leu Glu Asp Phe Glu Asp Trp Cys Lys Val
            260                 265                 270
Ala Lys Leu Ile Glu Glu Lys His Leu Thr Glu Ser Gly Leu Asp
            275                 280                 285
Glu Ile Lys Lys Ile Lys Leu Asn Met Asn Lys Gly Arg Val Phe
            290                 295                 300

<210> SEQ ID NO 2
<211> LENGTH: 303
<212> TYPE: PRT
<213> ORGANISM: Ophiostoma novo-ulmi subsp. americana (mitochondrion)

<400> SEQUENCE: 2

Met Ala Tyr Met Ser Arg Arg Glu Ser Ile Asn Pro Trp Ile Leu Thr
1               5                   10                  15
Gly Phe Ala Asp Ala Glu Gly Ser Phe Leu Leu Arg Ile Arg Asn Asn
                20                  25                  30
Asn Lys Ser Ser Val Gly Tyr Ser Thr Glu Leu Gly Phe Gln Ile Thr
            35                  40                  45
Leu His Asn Lys Asp Lys Ser Ile Leu Glu Asn Ile Gln Ser Thr Trp
50                  55                  60
Lys Val Gly Val Ile Ala Asn Ser Gly Asp Asn Ala Val Ser Leu Lys
65                  70                  75                  80
Val Thr Arg Phe Glu Asp Leu Lys Val Ile Asp His Phe Glu Lys
                85                  90                  95
Tyr Pro Leu Ile Thr Gln Lys Leu Gly Asp Tyr Lys Leu Phe Lys Gln
            100                 105                 110
Ala Phe Ser Val Met Glu Asn Lys Glu His Leu Lys Glu Asn Gly Ile
            115                 120                 125
Lys Glu Leu Val Arg Ile Lys Ala Lys Leu Asn Trp Gly Leu Thr Asp
            130                 135                 140
Glu Leu Lys Lys Ala Phe Pro Glu Asn Ile Ser Lys Glu Arg Ser Leu
145                 150                 155                 160
Ile Asn Lys Asn Ile Pro Asn Phe Lys Trp Leu Ala Gly Phe Thr Ser
                165                 170                 175
Gly Glu Gly Cys Phe Phe Val Asn Leu Ile Lys Ser Lys Ser Lys Leu
            180                 185                 190
```

```
Gly Val Gln Val Gln Leu Val Phe Ser Ile Thr Gln His Ile Lys Asp
            195                 200                 205

Lys Asn Leu Met Asn Ser Leu Ile Thr Tyr Leu Gly Cys Gly Tyr Ile
210                 215                 220

Lys Glu Lys Asn Lys Ser Glu Phe Ser Trp Leu Asp Phe Val Val Thr
225                 230                 235                 240

Lys Phe Ser Asp Ile Asn Asp Lys Ile Ile Pro Val Phe Gln Glu Asn
            245                 250                 255

Thr Leu Ile Gly Val Lys Leu Glu Asp Phe Glu Asp Trp Cys Lys Val
            260                 265                 270

Ala Lys Leu Ile Glu Glu Lys Lys His Leu Thr Glu Ser Gly Leu Asp
        275                 280                 285

Glu Ile Lys Lys Ile Lys Leu Asn Met Asn Lys Gly Arg Val Phe
290                 295                 300

<210> SEQ ID NO 3
<211> LENGTH: 303
<212> TYPE: PRT
<213> ORGANISM: Ophiostoma novo-ulmi subsp. americana (mitochondrion)
<220> FEATURE:
<221> NAME/KEY: MOD_RES
<222> LOCATION: (1)..(3)
<223> OTHER INFORMATION: Any amino acid or absent

<400> SEQUENCE: 3

Xaa Xaa Xaa Met Ser Arg Arg Glu Ser Ile Asn Pro Trp Ile Leu Thr
1               5                   10                  15

Gly Phe Ala Asp Ala Glu Gly Ser Phe Leu Leu Arg Ile Arg Asn Asn
            20                  25                  30

Asn Lys Ser Ser Val Gly Tyr Ser Thr Glu Leu Gly Phe Gln Ile Thr
        35                  40                  45

Leu His Asn Lys Asp Lys Ser Ile Leu Glu Asn Ile Gln Ser Thr Trp
    50                  55                  60

Lys Val Gly Val Ile Ala Asn Ser Gly Asp Asn Ala Val Ser Leu Lys
65                  70                  75                  80

Val Thr Arg Phe Glu Asp Leu Lys Val Ile Ile Asp His Phe Glu Lys
                85                  90                  95

Tyr Pro Leu Ile Thr Gln Lys Leu Gly Asp Tyr Lys Leu Phe Lys Gln
            100                 105                 110

Ala Phe Ser Val Met Glu Asn Lys Glu His Leu Lys Glu Asn Gly Ile
        115                 120                 125

Lys Glu Leu Val Arg Ile Lys Ala Lys Leu Asn Trp Gly Leu Thr Asp
130                 135                 140

Glu Leu Lys Lys Ala Phe Pro Glu Asn Ile Ser Lys Glu Arg Ser Leu
145                 150                 155                 160

Ile Asn Lys Asn Ile Pro Asn Phe Lys Trp Leu Ala Gly Phe Thr Ser
                165                 170                 175

Gly Glu Gly Cys Phe Phe Val Asn Leu Ile Lys Ser Lys Ser Lys Leu
            180                 185                 190

Gly Val Gln Val Gln Leu Val Phe Ser Ile Thr Gln His Ile Lys Asp
        195                 200                 205

Lys Asn Leu Met Asn Ser Leu Ile Thr Tyr Leu Gly Cys Gly Tyr Ile
    210                 215                 220

Lys Glu Lys Asn Lys Ser Glu Phe Ser Trp Leu Asp Phe Val Val Thr
225                 230                 235                 240

Lys Phe Ser Asp Ile Asn Asp Lys Ile Ile Pro Val Phe Gln Glu Asn
```

```
                        245                 250                 255
Thr Leu Ile Gly Val Lys Leu Glu Asp Phe Glu Asp Trp Cys Lys Val
            260                 265                 270

Ala Lys Leu Ile Glu Glu Lys Lys His Leu Thr Glu Ser Gly Leu Asp
        275                 280                 285

Glu Ile Lys Lys Ile Lys Leu Asn Met Asn Lys Gly Arg Val Phe
    290                 295                 300
```

<210> SEQ ID NO 4
<211> LENGTH: 303
<212> TYPE: PRT
<213> ORGANISM: Ophiostoma novo-ulmi subsp. americana (mitochondrion)
<220> FEATURE:
<221> NAME/KEY: MOD_RES
<222> LOCATION: (1)..(4)
<223> OTHER INFORMATION: Any amino acid or absent
<220> FEATURE:
<221> NAME/KEY: MOD_RES
<222> LOCATION: (302)..(303)
<223> OTHER INFORMATION: Any amino acid or absent

<400> SEQUENCE: 4

```
Xaa Xaa Xaa Xaa Ser Arg Arg Glu Ser Ile Asn Pro Trp Ile Leu Thr
1               5                   10                  15

Gly Phe Ala Asp Ala Glu Gly Ser Phe Leu Leu Arg Ile Arg Asn Asn
            20                  25                  30

Asn Lys Ser Ser Val Gly Tyr Ser Thr Glu Leu Gly Phe Gln Ile Thr
        35                  40                  45

Leu His Asn Lys Asp Lys Ser Ile Leu Glu Asn Ile Gln Ser Thr Trp
    50                  55                  60

Lys Val Gly Val Ile Ala Asn Ser Gly Asp Asn Ala Val Ser Leu Lys
65                  70                  75                  80

Val Thr Arg Phe Glu Asp Leu Lys Val Ile Ile Asp His Phe Glu Lys
                85                  90                  95

Tyr Pro Leu Ile Thr Gln Lys Leu Gly Asp Tyr Lys Leu Phe Lys Gln
            100                 105                 110

Ala Phe Ser Val Met Glu Asn Lys Glu His Leu Lys Glu Asn Gly Ile
        115                 120                 125

Lys Glu Leu Val Arg Ile Lys Ala Lys Leu Asn Trp Gly Leu Thr Asp
    130                 135                 140

Glu Leu Lys Lys Ala Phe Pro Glu Asn Ile Ser Lys Glu Arg Ser Leu
145                 150                 155                 160

Ile Asn Lys Asn Ile Pro Asn Phe Lys Trp Leu Ala Gly Phe Thr Ser
                165                 170                 175

Gly Glu Gly Cys Phe Phe Val Asn Leu Ile Lys Ser Lys Ser Lys Leu
            180                 185                 190

Gly Val Gln Val Gln Leu Val Phe Ser Ile Thr Gln His Ile Lys Asp
        195                 200                 205

Lys Asn Leu Met Asn Ser Leu Ile Thr Tyr Leu Gly Cys Gly Tyr Ile
    210                 215                 220

Lys Glu Lys Asn Lys Ser Glu Phe Ser Trp Leu Asp Phe Val Val Thr
225                 230                 235                 240

Lys Phe Ser Asp Ile Asn Asp Lys Ile Ile Pro Val Phe Gln Glu Asn
                245                 250                 255

Thr Leu Ile Gly Val Lys Leu Glu Asp Phe Glu Asp Trp Cys Lys Val
            260                 265                 270

Ala Lys Leu Ile Glu Glu Lys Lys His Leu Thr Glu Ser Gly Leu Asp
```

```
              275                 280                 285
Glu Ile Lys Lys Ile Lys Leu Asn Met Asn Lys Gly Arg Xaa Xaa
    290                 295                 300
```

<210> SEQ ID NO 5
<211> LENGTH: 303
<212> TYPE: PRT
<213> ORGANISM: Ophiostoma novo-ulmi subsp. americana (mitochondrion)
<220> FEATURE:
<221> NAME/KEY: MOD_RES
<222> LOCATION: (1)..(8)
<223> OTHER INFORMATION: Any amino acid or absent
<220> FEATURE:
<221> NAME/KEY: MOD_RES
<222> LOCATION: (302)..(303)
<223> OTHER INFORMATION: Any amino acid or absent

<400> SEQUENCE: 5

```
Xaa Xaa Xaa Xaa Xaa Xaa Xaa Ser Ile Asn Pro Trp Ile Leu Thr
1               5                   10                  15

Gly Phe Ala Asp Ala Glu Gly Ser Phe Leu Leu Arg Ile Arg Asn Asn
                20                  25                  30

Asn Lys Ser Ser Val Gly Tyr Ser Thr Glu Leu Gly Phe Gln Ile Thr
                35                  40                  45

Leu His Asn Lys Asp Lys Ser Ile Leu Glu Asn Ile Gln Ser Thr Trp
    50                  55                  60

Lys Val Gly Val Ile Ala Asn Ser Gly Asp Asn Ala Val Ser Leu Lys
65                  70                  75                  80

Val Thr Arg Phe Glu Asp Leu Lys Val Ile Ile Asp His Phe Glu Lys
                85                  90                  95

Tyr Pro Leu Ile Thr Gln Lys Leu Gly Asp Tyr Lys Leu Phe Lys Gln
                100                 105                 110

Ala Phe Ser Val Met Glu Asn Lys Glu His Leu Lys Glu Asn Gly Ile
                115                 120                 125

Lys Glu Leu Val Arg Ile Lys Ala Lys Leu Asn Trp Gly Leu Thr Asp
    130                 135                 140

Glu Leu Lys Lys Ala Phe Pro Glu Asn Ile Ser Lys Glu Arg Ser Leu
145                 150                 155                 160

Ile Asn Lys Asn Ile Pro Asn Phe Lys Trp Leu Ala Gly Phe Thr Ser
                165                 170                 175

Gly Glu Gly Cys Phe Phe Val Asn Leu Ile Lys Ser Lys Ser Lys Leu
                180                 185                 190

Gly Val Gln Val Gln Leu Val Phe Ser Ile Thr Gln His Ile Lys Asp
            195                 200                 205

Lys Asn Leu Met Asn Ser Leu Ile Thr Tyr Leu Gly Cys Gly Tyr Ile
    210                 215                 220

Lys Glu Lys Asn Lys Ser Glu Phe Ser Trp Leu Asp Phe Val Val Thr
225                 230                 235                 240

Lys Phe Ser Asp Ile Asn Asp Lys Ile Ile Pro Val Phe Gln Glu Asn
                245                 250                 255

Thr Leu Ile Gly Val Lys Leu Glu Asp Phe Glu Asp Trp Cys Lys Val
                260                 265                 270

Ala Lys Leu Ile Glu Glu Lys Lys His Leu Thr Glu Ser Gly Leu Asp
                275                 280                 285

Glu Ile Lys Lys Ile Lys Leu Asn Met Asn Lys Gly Arg Xaa Xaa
    290                 295                 300
```

```
<210> SEQ ID NO 6
<211> LENGTH: 303
<212> TYPE: PRT
<213> ORGANISM: Artificial Sequence
<220> FEATURE:
<223> OTHER INFORMATION: Synthesized I-OnuI variant

<400> SEQUENCE: 6
```

Met Ala Tyr Met Ser Arg Arg Glu Ser Ile Asn Pro Trp Ile Leu Thr
1               5                   10                  15

Gly Phe Ala Asp Ala Glu Gly Ser Phe Ile Leu Asp Ile Arg Asn Arg
            20                  25                  30

Asn Asn Glu Ser Asn Arg Tyr Arg Thr Ser Leu Arg Phe Gln Ile Thr
        35                  40                  45

Leu His Asn Lys Asp Lys Ser Ile Leu Glu Asn Ile Gln Ser Thr Trp
    50                  55                  60

Lys Val Gly Lys Ile Thr Asn Ser Gly Asp Arg Ala Val Met Leu Arg
65                  70                  75                  80

Val Thr Arg Phe Glu Asp Leu Lys Val Ile Ile Asp His Phe Glu Lys
                85                  90                  95

Tyr Pro Leu Ile Thr Gln Lys Leu Gly Asp Tyr Lys Leu Phe Lys Gln
            100                 105                 110

Ala Phe Ser Val Met Glu Asn Lys Glu His Leu Lys Glu Asn Gly Ile
        115                 120                 125

Lys Glu Leu Val Arg Ile Lys Ala Lys Met Asn Trp Gly Leu Thr Asp
    130                 135                 140

Glu Leu Lys Lys Ala Phe Pro Glu Asn Ile Ser Lys Glu Arg Pro Leu
145                 150                 155                 160

Ile Asn Lys Asn Ile Pro Asn Phe Lys Trp Leu Ala Gly Phe Thr Ser
                165                 170                 175

Gly Asp Gly Tyr Phe Gly Val Asn Leu Lys Lys Val Lys Gly Asn Ala
            180                 185                 190

Lys Val Tyr Val Gly Leu Arg Phe Ser Ile Ser Gln His Ile Arg Asp
        195                 200                 205

Lys Asn Leu Met Asn Ser Leu Ile Thr Tyr Leu Gly Cys Gly Ser Ile
    210                 215                 220

Trp Glu Lys Asn Lys Ser Glu Phe Ser Trp Leu Glu Phe Val Val Thr
225                 230                 235                 240

Lys Phe Ser Asp Ile Asn Asp Lys Ile Ile Pro Val Phe Gln Glu Asn
                245                 250                 255

Thr Leu Ile Gly Val Lys Leu Glu Asp Phe Glu Asp Trp Cys Lys Val
            260                 265                 270

Ala Lys Leu Ile Glu Glu Lys Lys His Leu Thr Glu Ser Gly Leu Asp
        275                 280                 285

Glu Ile Lys Lys Ile Lys Leu Asn Met Asn Lys Gly Arg Val Phe
    290                 295                 300

```
<210> SEQ ID NO 7
<211> LENGTH: 303
<212> TYPE: PRT
<213> ORGANISM: Artificial Sequence
<220> FEATURE:
<223> OTHER INFORMATION: Synthesized I-OnuI LHE variant
<220> FEATURE:
<221> NAME/KEY: MOD_RES
<222> LOCATION: (1)..(4)
<223> OTHER INFORMATION: Any amino acid or absent
<220> FEATURE:
<221> NAME/KEY: MOD_RES
```

<222> LOCATION: (302)..(303)
<223> OTHER INFORMATION: Any amino acid or absent

<400> SEQUENCE: 7

Xaa Xaa Xaa Xaa Ser Arg Arg Glu Ser Ile Asn Pro Trp Ile Leu Thr
1               5                   10                  15

Gly Phe Ala Asp Ala Glu Gly Ser Phe Ile Leu Asp Ile Arg Asn Arg
            20                  25                  30

Asn Asn Glu Ser Asn Arg Tyr Arg Thr Ser Leu Arg Phe Gln Ile Thr
        35                  40                  45

Leu His Asn Lys Asp Lys Ser Ile Leu Glu Asn Ile Gln Ser Thr Trp
50                  55                  60

Lys Val Gly Lys Ile Thr Asn Ser Ser Asp Arg Ala Val Met Leu Arg
65                  70                  75                  80

Val Thr Arg Phe Glu Asp Leu Lys Val Ile Ile Asp His Phe Glu Lys
                85                  90                  95

Tyr Pro Leu Ile Thr Gln Lys Leu Gly Asp Tyr Lys Leu Phe Lys Gln
            100                 105                 110

Ala Phe Ser Val Met Glu Asn Lys Glu His Leu Lys Glu Asn Gly Ile
        115                 120                 125

Lys Glu Leu Val Arg Ile Lys Ala Lys Met Asn Trp Gly Leu Asn Asp
130                 135                 140

Glu Leu Lys Lys Ala Phe Pro Glu Asn Ile Ser Lys Glu Arg Pro Leu
145                 150                 155                 160

Ile Asn Lys Asn Ile Pro Asn Phe Lys Trp Leu Ala Gly Phe Thr Ala
                165                 170                 175

Gly Glu Gly His Phe Gly Val Asn Leu Lys Lys Val Lys Gly Thr Ala
            180                 185                 190

Lys Val Tyr Val Gly Leu Arg Phe Ala Ile Ser Gln His Ile Arg Asp
        195                 200                 205

Lys Asn Leu Met Asn Ser Leu Ile Thr Tyr Leu Gly Cys Gly Ser Ile
210                 215                 220

Arg Glu Lys Asn Lys Ser Glu Phe Arg Trp Leu Glu Phe Glu Val Thr
225                 230                 235                 240

Lys Phe Ser Asp Ile Asn Asp Lys Ile Ile Pro Val Phe Gln Glu Asn
                245                 250                 255

Thr Leu Ile Gly Val Lys Leu Glu Asp Phe Glu Asp Trp Cys Lys Val
            260                 265                 270

Ala Lys Leu Ile Glu Glu Lys Lys His Leu Thr Glu Ser Gly Leu Asp
        275                 280                 285

Glu Ile Lys Lys Ile Lys Leu Asn Met Asn Lys Gly Arg Xaa Xaa
290                 295                 300

<210> SEQ ID NO 8
<211> LENGTH: 303
<212> TYPE: PRT
<213> ORGANISM: Artificial Sequence
<220> FEATURE:
<223> OTHER INFORMATION: Synthesized I-OnuI LHE variant
<220> FEATURE:
<221> NAME/KEY: MOD_RES
<222> LOCATION: (1)..(4)
<223> OTHER INFORMATION: Any amino acid or absent
<220> FEATURE:
<221> NAME/KEY: MOD_RES
<222> LOCATION: (302)..(303)
<223> OTHER INFORMATION: Any amino acid or absent

<400> SEQUENCE: 8

Xaa Xaa Xaa Xaa Ser Arg Arg Glu Ser Ile Asn Pro Trp Ile Leu Thr
1               5                   10                  15

Gly Phe Ala Asp Ala Glu Gly Ser Phe Ile Leu Asp Ile Arg Asn Arg
                20                  25                  30

Asn Asn Glu Ser Asn Arg Tyr Arg Thr Ser Leu Arg Phe Gln Ile Thr
            35                  40                  45

Leu His Asn Lys Asp Lys Ser Ile Leu Glu Asn Ile Gln Ser Thr Trp
        50                  55                  60

Lys Val Gly Lys Ile Thr Asn Ser Ser Asp Arg Ala Val Met Leu Arg
65                  70                  75                  80

Val Thr Arg Phe Glu Asp Leu Lys Val Ile Ile Asp His Phe Glu Lys
                85                  90                  95

Tyr Pro Leu Ile Thr Gln Lys Leu Gly Asp Tyr Lys Leu Phe Lys Gln
                100                 105                 110

Ala Phe Ser Val Met Glu Asn Lys Glu His Leu Lys Glu Asn Gly Ile
            115                 120                 125

Lys Glu Leu Val Arg Ile Lys Ala Lys Met Asn Trp Gly Leu Asn Asp
        130                 135                 140

Glu Leu Lys Lys Ala Phe Pro Glu Asn Ile Ser Lys Glu Arg Pro Leu
145                 150                 155                 160

Ile Asn Lys Asn Ile Pro Asn Phe Lys Trp Leu Ala Gly Phe Thr Ala
                165                 170                 175

Gly Asp Gly His Phe Gly Val Asn Leu Lys Val Lys Gly Thr Ala
                180                 185                 190

Lys Val Tyr Val Gly Leu Arg Phe Ala Ile Ser Gln His Ile Arg Asp
            195                 200                 205

Lys Asn Leu Met Asn Ser Leu Ile Thr Tyr Leu Gly Cys Gly Ser Ile
        210                 215                 220

Arg Glu Lys Asn Lys Ser Glu Phe Arg Trp Leu Glu Phe Glu Val Thr
225                 230                 235                 240

Lys Phe Ser Asp Ile Asn Asp Lys Ile Ile Pro Val Phe Gln Glu Asn
                245                 250                 255

Thr Leu Ile Gly Val Lys Leu Glu Asp Phe Glu Asp Trp Cys Lys Val
                260                 265                 270

Ala Lys Leu Ile Glu Glu Lys Lys His Leu Thr Glu Ser Gly Leu Asp
            275                 280                 285

Glu Ile Lys Lys Ile Lys Leu Asn Met Asn Lys Gly Arg Xaa Xaa
        290                 295                 300

<210> SEQ ID NO 9
<211> LENGTH: 877
<212> TYPE: PRT
<213> ORGANISM: Artificial Sequence
<220> FEATURE:
<223> OTHER INFORMATION: Synthesized I-OnuI variant megaTAL construct

<400> SEQUENCE: 9

Met Gly Ser Ala Pro Lys Lys Lys Arg Lys Val Val Asp Leu Arg
1               5                   10                  15

Thr Leu Gly Tyr Ser Gln Gln Gln Glu Lys Ile Lys Pro Lys Val
                20                  25                  30

Arg Ser Thr Val Ala Gln His His Glu Ala Leu Val Gly His Gly Phe
            35                  40                  45

Thr His Ala His Ile Val Ala Leu Ser Gln His Pro Ala Ala Leu Gly
        50                  55                  60

```
Thr Val Ala Val Thr Tyr Gln His Ile Ile Thr Ala Leu Pro Glu Ala
 65                  70                  75                  80

Thr His Glu Asp Ile Val Gly Val Gly Lys Gln Trp Ser Gly Ala Arg
                 85                  90                  95

Ala Leu Glu Ala Leu Leu Thr Asp Ala Gly Glu Leu Arg Gly Pro Pro
            100                 105                 110

Leu Gln Leu Asp Thr Gly Gln Leu Val Lys Ile Ala Lys Arg Gly Gly
            115                 120                 125

Val Thr Ala Met Glu Ala Val His Ala Ser Arg Asn Ala Leu Thr Gly
130                 135                 140

Ala Pro Leu Asn Leu Thr Pro Asp Gln Val Val Ala Ile Ala Ser Asn
145                 150                 155                 160

Ile Gly Gly Lys Gln Ala Leu Glu Thr Val Gln Arg Leu Leu Pro Val
                165                 170                 175

Leu Cys Gln Asp His Gly Leu Thr Pro Asp Gln Val Val Ala Ile Ala
            180                 185                 190

Ser Asn Ile Gly Gly Lys Gln Ala Leu Glu Thr Val Gln Arg Leu Leu
            195                 200                 205

Pro Val Leu Cys Gln Asp His Gly Leu Thr Pro Asp Gln Val Val Ala
210                 215                 220

Ile Ala Ser Asn Ile Gly Gly Lys Gln Ala Leu Glu Thr Val Gln Arg
225                 230                 235                 240

Leu Leu Pro Val Leu Cys Gln Asp His Gly Leu Thr Pro Asp Gln Val
                245                 250                 255

Val Ala Ile Ala Ser Asn Gly Gly Gly Lys Gln Ala Leu Glu Thr Val
            260                 265                 270

Gln Arg Leu Leu Pro Val Leu Cys Gln Asp His Gly Leu Thr Pro Asp
            275                 280                 285

Gln Val Val Ala Ile Ala Ser His Asp Gly Gly Lys Gln Ala Leu Glu
290                 295                 300

Thr Val Gln Arg Leu Leu Pro Val Leu Cys Gln Asp His Gly Leu Thr
305                 310                 315                 320

Pro Asp Gln Val Val Ala Ile Ala Ser His Asp Gly Gly Lys Gln Ala
                325                 330                 335

Leu Glu Thr Val Gln Arg Leu Leu Pro Val Leu Cys Gln Asp His Gly
            340                 345                 350

Leu Thr Pro Asp Gln Val Val Ala Ile Ala Ser Asn Ile Gly Gly Lys
            355                 360                 365

Gln Ala Leu Glu Thr Val Gln Arg Leu Leu Pro Val Leu Cys Gln Asp
            370                 375                 380

His Gly Leu Thr Pro Asp Gln Val Val Ala Ile Ala Ser Asn Asn Gly
385                 390                 395                 400

Gly Lys Gln Ala Leu Glu Thr Val Gln Arg Leu Leu Pro Val Leu Cys
                405                 410                 415

Gln Asp His Gly Leu Thr Pro Asp Gln Val Val Ala Ile Ala Ser Asn
            420                 425                 430

Gly Gly Gly Lys Gln Ala Leu Glu Thr Val Gln Arg Leu Leu Pro Val
            435                 440                 445

Leu Cys Gln Asp His Gly Leu Thr Pro Asp Gln Val Val Ala Ile Ala
            450                 455                 460

Ser Asn Asn Gly Gly Lys Gln Ala Leu Glu Thr Val Gln Arg Leu Leu
465                 470                 475                 480
```

Pro Val Leu Cys Gln Asp His Gly Leu Thr Pro Asp Gln Val Val Ala
            485                 490                 495

Ile Ala Ser Asn Ile Gly Gly Lys Gln Ala Leu Glu Ser Ile Val Ala
        500                 505                 510

Gln Leu Ser Arg Pro Asp Pro Ala Leu Ala Ala Leu Thr Asn Asp His
    515                 520                 525

Leu Val Ala Leu Ala Cys Leu Gly Gly Arg Pro Ala Met Asp Ala Val
530                 535                 540

Lys Lys Gly Leu Pro His Ala Pro Glu Leu Ile Arg Arg Val Asn Arg
545                 550                 555                 560

Arg Ile Gly Glu Arg Thr Ser His Arg Val Ala Ile Ser Arg Val Gly
                565                 570                 575

Gly Ser Ser Arg Arg Glu Ser Ile Asn Pro Trp Ile Leu Thr Gly Phe
            580                 585                 590

Ala Asp Ala Glu Gly Ser Phe Ile Leu Asp Ile Arg Asn Arg Asn Asn
        595                 600                 605

Glu Ser Asn Arg Tyr Arg Thr Ser Leu Arg Phe Gln Ile Thr Leu His
    610                 615                 620

Asn Lys Asp Lys Ser Ile Leu Glu Asn Ile Gln Ser Thr Trp Lys Val
625                 630                 635                 640

Gly Lys Ile Thr Asn Ser Gly Asp Arg Ala Val Met Leu Arg Val Thr
                645                 650                 655

Arg Phe Glu Asp Leu Lys Val Ile Ile Asp His Phe Glu Lys Tyr Pro
            660                 665                 670

Leu Ile Thr Gln Lys Leu Gly Asp Tyr Lys Leu Phe Lys Gln Ala Phe
        675                 680                 685

Ser Val Met Glu Asn Lys Glu His Leu Lys Glu Asn Gly Ile Lys Glu
    690                 695                 700

Leu Val Arg Ile Lys Ala Lys Met Asn Trp Gly Leu Thr Asp Glu Leu
705                 710                 715                 720

Lys Lys Ala Phe Pro Glu Asn Ile Ser Lys Glu Arg Pro Leu Ile Asn
                725                 730                 735

Lys Asn Ile Pro Asn Phe Lys Trp Leu Ala Gly Phe Thr Ser Gly Asp
            740                 745                 750

Gly Tyr Phe Gly Val Asn Leu Lys Lys Val Lys Gly Asn Ala Lys Val
        755                 760                 765

Tyr Val Gly Leu Arg Phe Ser Ile Ser Gln His Ile Arg Asp Lys Asn
    770                 775                 780

Leu Met Asn Ser Leu Ile Thr Tyr Leu Gly Cys Gly Ser Ile Trp Glu
785                 790                 795                 800

Lys Asn Lys Ser Glu Phe Ser Trp Leu Glu Phe Val Val Thr Lys Phe
                805                 810                 815

Ser Asp Ile Asn Asp Lys Ile Ile Pro Val Phe Gln Glu Asn Thr Leu
            820                 825                 830

Ile Gly Val Lys Leu Glu Asp Phe Glu Asp Trp Cys Lys Val Ala Lys
        835                 840                 845

Leu Ile Glu Glu Lys Lys His Leu Thr Glu Ser Gly Leu Asp Glu Ile
    850                 855                 860

Lys Lys Ile Lys Leu Asn Met Asn Lys Gly Arg Val Phe
865                 870                 875

<210> SEQ ID NO 10
<211> LENGTH: 877
<212> TYPE: PRT

<213> ORGANISM: Artificial Sequence
<220> FEATURE:
<223> OTHER INFORMATION: Synthesized megaTAL construct

<400> SEQUENCE: 10

```
Met Gly Ser Ala Pro Lys Lys Arg Lys Val Val Asp Leu Arg
1               5                   10                  15

Thr Leu Gly Tyr Ser Gln Gln Gln Glu Lys Ile Lys Pro Lys Val
            20                  25                  30

Arg Ser Thr Val Ala Gln His His Glu Ala Leu Val Gly His Gly Phe
            35                  40                  45

Thr His Ala His Ile Val Ala Leu Ser Gln His Pro Ala Ala Leu Gly
    50                  55                  60

Thr Val Ala Val Thr Tyr Gln His Ile Ile Thr Ala Leu Pro Glu Ala
65              70                  75                  80

Thr His Glu Asp Ile Val Gly Val Gly Lys Gln Trp Ser Gly Ala Arg
    His         85                  90                  95

Ala Leu Glu Ala Leu Leu Thr Asp Ala Gly Glu Leu Arg Gly Pro Pro
            100                 105                 110

Leu Gln Leu Asp Thr Gly Gln Leu Val Lys Ile Ala Lys Arg Gly Gly
            115                 120                 125

Val Thr Ala Met Glu Ala Val His Ala Ser Arg Asn Ala Leu Thr Gly
    130                 135                 140

Ala Pro Leu Asn Leu Thr Pro Asp Gln Val Val Ala Ile Ala Ser Asn
145                 150                 155                 160

Ile Gly Gly Lys Gln Ala Leu Glu Thr Val Gln Arg Leu Leu Pro Val
                165                 170                 175

Leu Cys Gln Asp His Gly Leu Thr Pro Asp Gln Val Val Ala Ile Ala
            180                 185                 190

Ser Asn Ile Gly Gly Lys Gln Ala Leu Glu Thr Val Gln Arg Leu Leu
    195                 200                 205

Pro Val Leu Cys Gln Asp His Gly Leu Thr Pro Asp Gln Val Val Ala
    210                 215                 220

Ile Ala Ser Asn Ile Gly Gly Lys Gln Ala Leu Glu Thr Val Gln Arg
225                 230                 235                 240

Leu Leu Pro Val Leu Cys Gln Asp His Gly Leu Thr Pro Asp Gln Val
            245                 250                 255

Val Ala Ile Ala Ser Asn Gly Gly Gly Lys Gln Ala Leu Glu Thr Val
            260                 265                 270

Gln Arg Leu Leu Pro Val Leu Cys Gln Asp His Gly Leu Thr Pro Asp
            275                 280                 285

Gln Val Val Ala Ile Ala Ser His Asp Gly Gly Lys Gln Ala Leu Glu
            290                 295                 300

Thr Val Gln Arg Leu Leu Pro Val Leu Cys Gln Asp His Gly Leu Thr
305                 310                 315                 320

Pro Asp Gln Val Val Ala Ile Ala Ser His Asp Gly Gly Lys Gln Ala
                325                 330                 335

Leu Glu Thr Val Gln Arg Leu Leu Pro Val Leu Cys Gln Asp His Gly
            340                 345                 350

Leu Thr Pro Asp Gln Val Val Ala Ile Ala Ser Asn Ile Gly Gly Lys
            355                 360                 365

Gln Ala Leu Glu Thr Val Gln Arg Leu Leu Pro Val Leu Cys Gln Asp
    370                 375                 380

His Gly Leu Thr Pro Asp Gln Val Val Ala Ile Ala Ser Asn Asn Gly
```

```
            385                 390                 395                 400
        Gly Lys Gln Ala Leu Glu Thr Val Gln Arg Leu Leu Pro Val Leu Cys
                        405                 410                 415

Gln Asp His Gly Leu Thr Pro Asp Gln Val Val Ala Ile Ala Ser Asn
                        420                 425                 430

Gly Gly Gly Lys Gln Ala Leu Glu Thr Val Gln Arg Leu Leu Pro Val
                        435                 440                 445

Leu Cys Gln Asp His Gly Leu Thr Pro Asp Gln Val Val Ala Ile Ala
                450                 455                 460

Ser Asn Asn Gly Gly Lys Gln Ala Leu Glu Thr Val Gln Arg Leu Leu
        465                 470                 475                 480

Pro Val Leu Cys Gln Asp His Gly Leu Thr Pro Asp Gln Val Val Ala
                        485                 490                 495

Ile Ala Ser Asn Ile Gly Gly Lys Gln Ala Leu Glu Ser Ile Val Ala
                        500                 505                 510

Gln Leu Ser Arg Pro Asp Pro Ala Leu Ala Ala Leu Thr Asn Asp His
                        515                 520                 525

Leu Val Ala Leu Ala Cys Leu Gly Gly Arg Pro Ala Met Asp Ala Val
                530                 535                 540

Lys Lys Gly Leu Pro His Ala Pro Glu Leu Ile Arg Arg Val Asn Arg
        545                 550                 555                 560

Arg Ile Gly Glu Arg Thr Ser His Arg Val Ala Ile Ser Arg Val Gly
                        565                 570                 575

Gly Ser Ser Arg Arg Glu Ser Ile Asn Pro Trp Ile Leu Thr Gly Phe
                        580                 585                 590

Ala Asp Ala Glu Gly Ser Phe Ile Leu Asp Ile Arg Asn Arg Asn Asn
                        595                 600                 605

Glu Ser Asn Arg Tyr Arg Thr Ser Leu Arg Phe Gln Ile Thr Leu His
                        610                 615                 620

Asn Lys Asp Lys Ser Ile Leu Glu Asn Ile Gln Ser Thr Trp Lys Val
        625                 630                 635                 640

Gly Lys Ile Thr Asn Ser Gly Asp Arg Ala Val Met Leu Arg Val Thr
                        645                 650                 655

Arg Phe Glu Asp Leu Lys Val Ile Ile Asp His Phe Glu Lys Tyr Pro
                        660                 665                 670

Leu Ile Thr Gln Lys Leu Gly Asp Tyr Lys Leu Phe Lys Gln Ala Phe
                        675                 680                 685

Ser Val Met Glu Asn Lys Glu His Leu Lys Glu Asn Gly Ile Lys Glu
                        690                 695                 700

Leu Val Arg Ile Lys Ala Lys Met Asn Trp Gly Leu Thr Asp Glu Leu
        705                 710                 715                 720

Lys Lys Ala Phe Pro Glu Asn Ile Ser Lys Glu Arg Pro Leu Ile Asn
                        725                 730                 735

Lys Asn Ile Pro Asn Phe Lys Trp Leu Ala Gly Phe Thr Ser Gly Asp
                        740                 745                 750

Gly Tyr Phe Gly Val Asn Leu Lys Lys Val Lys Gly Asn Ala Lys Val
                        755                 760                 765

Tyr Val Gly Leu Arg Phe Ser Ile Ser Gln His Ile Arg Asp Lys Asn
                770                 775                 780

Leu Met Asn Ser Leu Ile Thr Tyr Leu Gly Cys Gly Ser Ile Trp Glu
        785                 790                 795                 800

Lys Asn Lys Ser Glu Phe Ser Trp Leu Glu Phe Val Val Thr Lys Phe
                        805                 810                 815
```

```
Ser Asp Ile Asn Asp Lys Ile Ile Pro Val Phe Gln Glu Asn Thr Leu
                820                 825                 830

Ile Gly Val Lys Leu Glu Asp Phe Glu Asp Trp Cys Lys Val Ala Lys
            835                 840                 845

Leu Ile Glu Glu Lys Lys His Leu Thr Glu Ser Gly Leu Asp Glu Ile
        850                 855                 860

Lys Lys Ile Lys Leu Asn Met Asn Lys Gly Arg Val Phe
865                 870                 875

<210> SEQ ID NO 11
<211> LENGTH: 875
<212> TYPE: PRT
<213> ORGANISM: Artificial Sequence
<220> FEATURE:
<223> OTHER INFORMATION: Synthesized megaTAL construct

<400> SEQUENCE: 11

Met Gly Ser Ala Pro Pro Lys Lys Lys Arg Lys Val Val Asp Leu Arg
1               5                   10                  15

Thr Leu Gly Tyr Ser Gln Gln Gln Gln Glu Lys Ile Lys Pro Lys Val
            20                  25                  30

Arg Ser Thr Val Ala Gln His His Glu Ala Leu Val Gly His Gly Phe
        35                  40                  45

Thr His Ala His Ile Val Ala Leu Ser Gln His Pro Ala Ala Leu Gly
    50                  55                  60

Thr Val Ala Val Thr Tyr Gln His Ile Ile Thr Ala Leu Pro Glu Ala
65                  70                  75                  80

Thr His Glu Asp Ile Val Gly Val Gly Lys Gln Trp Ser Gly Ala Arg
                85                  90                  95

Ala Leu Glu Ala Leu Leu Thr Asp Ala Gly Glu Leu Arg Gly Pro Pro
            100                 105                 110

Leu Gln Leu Asp Thr Gly Gln Leu Val Lys Ile Ala Lys Arg Gly Gly
        115                 120                 125

Val Thr Ala Met Glu Ala Val His Ala Ser Arg Asn Ala Leu Thr Gly
    130                 135                 140

Ala Pro Leu Asn Leu Thr Pro Asp Gln Val Val Ala Ile Ala Ser Asn
145                 150                 155                 160

Ile Gly Gly Lys Gln Ala Leu Glu Thr Val Gln Arg Leu Leu Pro Val
                165                 170                 175

Leu Cys Gln Asp His Gly Leu Thr Pro Asp Gln Val Val Ala Ile Ala
            180                 185                 190

Ser Asn Ile Gly Gly Lys Gln Ala Leu Glu Thr Val Gln Arg Leu Leu
        195                 200                 205

Pro Val Leu Cys Gln Asp His Gly Leu Thr Pro Asp Gln Val Val Ala
    210                 215                 220

Ile Ala Ser Asn Ile Gly Gly Lys Gln Ala Leu Glu Thr Val Gln Arg
225                 230                 235                 240

Leu Leu Pro Val Leu Cys Gln Asp His Gly Leu Thr Pro Asp Gln Val
                245                 250                 255

Val Ala Ile Ala Ser Asn Gly Gly Gly Lys Gln Ala Leu Glu Thr Val
            260                 265                 270

Gln Arg Leu Leu Pro Val Leu Cys Gln Asp His Gly Leu Thr Pro Asp
        275                 280                 285

Gln Val Val Ala Ile Ala Ser His Asp Gly Gly Lys Gln Ala Leu Glu
    290                 295                 300
```

```
Thr Val Gln Arg Leu Leu Pro Val Leu Cys Gln Asp His Gly Leu Thr
305                 310                 315                 320

Pro Asp Gln Val Val Ala Ile Ala Ser His Asp Gly Gly Lys Gln Ala
            325                 330                 335

Leu Glu Thr Val Gln Arg Leu Leu Pro Val Leu Cys Gln Asp His Gly
            340                 345                 350

Leu Thr Pro Asp Gln Val Val Ala Ile Ala Ser Asn Ile Gly Gly Lys
            355                 360                 365

Gln Ala Leu Glu Thr Val Gln Arg Leu Leu Pro Val Leu Cys Gln Asp
370                 375                 380

His Gly Leu Thr Pro Asp Gln Val Val Ala Ile Ala Ser Asn Asn Gly
385                 390                 395                 400

Gly Lys Gln Ala Leu Glu Thr Val Gln Arg Leu Leu Pro Val Leu Cys
                405                 410                 415

Gln Asp His Gly Leu Thr Pro Asp Gln Val Val Ala Ile Ala Ser Asn
            420                 425                 430

Gly Gly Gly Lys Gln Ala Leu Glu Thr Val Gln Arg Leu Leu Pro Val
            435                 440                 445

Leu Cys Gln Asp His Gly Leu Thr Pro Asp Gln Val Val Ala Ile Ala
450                 455                 460

Ser Asn Asn Gly Gly Lys Gln Ala Leu Glu Thr Val Gln Arg Leu Leu
465                 470                 475                 480

Pro Val Leu Cys Gln Asp His Gly Leu Thr Pro Asp Gln Val Val Ala
                485                 490                 495

Ile Ala Ser Asn Ile Gly Gly Lys Gln Ala Leu Glu Ser Ile Val Ala
            500                 505                 510

Gln Leu Ser Arg Pro Asp Pro Ala Leu Ala Ala Leu Thr Asn Asp His
            515                 520                 525

Leu Val Ala Leu Ala Cys Leu Gly Gly Arg Pro Ala Met Asp Ala Val
530                 535                 540

Lys Lys Gly Leu Pro His Ala Pro Glu Leu Ile Arg Arg Val Asn Arg
545                 550                 555                 560

Arg Ile Gly Glu Arg Thr Ser His Arg Val Ala Ile Ser Arg Val Gly
                565                 570                 575

Gly Ser Ser Arg Arg Glu Ser Ile Asn Pro Trp Ile Leu Thr Gly Phe
            580                 585                 590

Ala Asp Ala Glu Gly Ser Phe Ile Leu Asp Ile Arg Asn Arg Asn Asn
            595                 600                 605

Glu Ser Asn Arg Tyr Arg Thr Ser Leu Arg Phe Gln Ile Thr Leu His
            610                 615                 620

Asn Lys Asp Lys Ser Ile Leu Glu Asn Ile Gln Ser Thr Trp Lys Val
625                 630                 635                 640

Gly Lys Ile Thr Asn Ser Ser Asp Arg Ala Val Met Leu Arg Val Thr
                645                 650                 655

Arg Phe Glu Asp Leu Lys Val Ile Ile Asp His Phe Glu Lys Tyr Pro
            660                 665                 670

Leu Ile Thr Gln Lys Leu Gly Asp Tyr Lys Leu Phe Lys Gln Ala Phe
            675                 680                 685

Ser Val Met Glu Asn Lys Glu His Leu Lys Glu Asn Gly Ile Lys Glu
            690                 695                 700

Leu Val Arg Ile Lys Ala Lys Met Asn Trp Gly Leu Asn Asp Glu Leu
705                 710                 715                 720
```

-continued

```
Lys Lys Ala Phe Pro Glu Asn Ile Ser Lys Glu Arg Pro Leu Ile Asn
                725                 730                 735

Lys Asn Ile Pro Asn Phe Lys Trp Leu Ala Gly Phe Thr Ala Gly Asp
            740                 745                 750

Gly His Phe Gly Val Asn Leu Lys Lys Val Lys Gly Thr Ala Lys Val
        755                 760                 765

Tyr Val Gly Leu Arg Phe Ala Ile Ser Gln His Ile Arg Asp Lys Asn
770                 775                 780

Leu Met Asn Ser Leu Ile Thr Tyr Leu Gly Cys Gly Ser Ile Arg Glu
785                 790                 795                 800

Lys Asn Lys Ser Glu Phe Arg Trp Leu Glu Phe Glu Val Thr Lys Phe
                805                 810                 815

Ser Asp Ile Asn Asp Lys Ile Ile Pro Val Phe Gln Glu Asn Thr Leu
            820                 825                 830

Ile Gly Val Lys Leu Glu Asp Phe Glu Asp Trp Cys Lys Val Ala Lys
        835                 840                 845

Leu Ile Glu Glu Lys Lys His Leu Thr Glu Ser Gly Leu Asp Glu Ile
850                 855                 860

Lys Lys Ile Lys Leu Asn Met Asn Lys Gly Arg
865                 870                 875
```

<210> SEQ ID NO 12
<211> LENGTH: 909
<212> TYPE: PRT
<213> ORGANISM: Artificial Sequence
<220> FEATURE:
<223> OTHER INFORMATION: Synthesized megaTAL construct

<400> SEQUENCE: 12

```
Met Gly Ser Ala Pro Pro Lys Lys Lys Arg Lys Val Val Asp Leu Arg
1               5                   10                  15

Thr Leu Gly Tyr Ser Gln Gln Gln Glu Lys Ile Lys Pro Lys Val
            20                  25                  30

Arg Ser Thr Val Ala Gln His His Glu Ala Leu Val Gly His Gly Phe
        35                  40                  45

Thr His Ala His Ile Val Ala Leu Ser Gln His Pro Ala Ala Leu Gly
    50                  55                  60

Thr Val Ala Val Thr Tyr Gln His Ile Ile Thr Ala Leu Pro Glu Ala
65                  70                  75                  80

Thr His Glu Asp Ile Val Gly Val Gly Lys Gln Trp Ser Gly Ala Arg
                85                  90                  95

Ala Leu Glu Ala Leu Leu Thr Asp Ala Gly Glu Leu Arg Gly Pro Pro
            100                 105                 110

Leu Gln Leu Asp Thr Gly Gln Leu Val Lys Ile Ala Lys Arg Gly Gly
        115                 120                 125

Val Thr Ala Met Glu Ala Val His Ala Ser Arg Asn Ala Leu Thr Gly
130                 135                 140

Ala Pro Leu Asn Leu Thr Pro Asp Gln Val Val Ala Ile Ala Ser Asn
145                 150                 155                 160

Ile Gly Gly Lys Gln Ala Leu Glu Thr Val Gln Arg Leu Leu Pro Val
                165                 170                 175

Leu Cys Gln Asp His Gly Leu Thr Pro Asp Gln Val Val Ala Ile Ala
            180                 185                 190

Ser Asn Ile Gly Gly Lys Gln Ala Leu Glu Thr Val Gln Arg Leu Leu
        195                 200                 205
```

```
Pro Val Leu Cys Gln Asp His Gly Leu Thr Pro Asp Gln Val Val Ala
210                 215                 220

Ile Ala Ser Asn Ile Gly Gly Lys Gln Ala Leu Glu Thr Val Gln Arg
225                 230                 235                 240

Leu Leu Pro Val Leu Cys Gln Asp His Gly Leu Thr Pro Asp Gln Val
            245                 250                 255

Val Ala Ile Ala Ser Asn Gly Gly Lys Gln Ala Leu Glu Thr Val
            260                 265                 270

Gln Arg Leu Leu Pro Val Leu Cys Gln Asp His Gly Leu Thr Pro Asp
            275                 280                 285

Gln Val Val Ala Ile Ala Ser His Asp Gly Gly Lys Gln Ala Leu Glu
290                 295                 300

Thr Val Gln Arg Leu Leu Pro Val Leu Cys Gln Asp His Gly Leu Thr
305                 310                 315                 320

Pro Asp Gln Val Val Ala Ile Ala Ser His Asp Gly Gly Lys Gln Ala
                325                 330                 335

Leu Glu Thr Val Gln Arg Leu Leu Pro Val Leu Cys Gln Asp His Gly
            340                 345                 350

Leu Thr Pro Asp Gln Val Val Ala Ile Ala Ser Asn Ile Gly Gly Lys
355                 360                 365

Gln Ala Leu Glu Thr Val Gln Arg Leu Leu Pro Val Leu Cys Gln Asp
370                 375                 380

His Gly Leu Thr Pro Asp Gln Val Val Ala Ile Ala Ser Asn Asn Gly
385                 390                 395                 400

Gly Lys Gln Ala Leu Glu Thr Val Gln Arg Leu Leu Pro Val Leu Cys
            405                 410                 415

Gln Asp His Gly Leu Thr Pro Asp Gln Val Val Ala Ile Ala Ser Asn
            420                 425                 430

Gly Gly Gly Lys Gln Ala Leu Glu Thr Val Gln Arg Leu Leu Pro Val
            435                 440                 445

Leu Cys Gln Asp His Gly Leu Thr Pro Asp Gln Val Val Ala Ile Ala
    450                 455                 460

Ser Asn Asn Gly Gly Lys Gln Ala Leu Glu Thr Val Gln Arg Leu Leu
465                 470                 475                 480

Pro Val Leu Cys Gln Asp His Gly Leu Thr Pro Asp Gln Val Val Ala
            485                 490                 495

Ile Ala Ser Asn Ile Gly Gly Lys Gln Ala Leu Glu Thr Val Gln Arg
            500                 505                 510

Leu Leu Pro Val Leu Cys Gln Asp His Gly Leu Thr Pro Asp Gln Val
            515                 520                 525

Val Ala Ile Ala Ser His Asp Gly Gly Lys Gln Ala Leu Glu Ser Ile
530                 535                 540

Val Ala Gln Leu Ser Arg Pro Asp Pro Ala Leu Ala Ala Leu Thr Asn
545                 550                 555                 560

Asp His Leu Val Ala Leu Ala Cys Leu Gly Gly Arg Pro Ala Met Asp
                565                 570                 575

Ala Val Lys Lys Gly Leu Pro His Ala Pro Glu Leu Ile Arg Arg Val
            580                 585                 590

Asn Arg Arg Ile Gly Glu Arg Thr Ser His Arg Val Ala Ile Ser Arg
            595                 600                 605

Val Gly Gly Ser Ser Arg Arg Glu Ser Ile Asn Pro Trp Ile Leu Thr
    610                 615                 620

Gly Phe Ala Asp Ala Glu Gly Ser Phe Ile Leu Asp Ile Arg Asn Arg
```

-continued

```
                625                 630                 635                 640
Asn Asn Glu Ser Asn Arg Tyr Arg Thr Ser Leu Arg Phe Gln Ile Thr
                    645                 650                 655
Leu His Asn Lys Asp Lys Ser Ile Leu Glu Asn Ile Gln Ser Thr Trp
                660                 665                 670
Lys Val Gly Lys Ile Thr Asn Ser Ser Asp Arg Ala Val Met Leu Arg
            675                 680                 685
Val Thr Arg Phe Glu Asp Leu Lys Val Ile Ile Asp His Phe Glu Lys
        690                 695                 700
Tyr Pro Leu Ile Thr Gln Lys Leu Gly Asp Tyr Lys Leu Phe Lys Gln
705                 710                 715                 720
Ala Phe Ser Val Met Glu Asn Lys Glu His Leu Lys Glu Asn Gly Ile
                725                 730                 735
Lys Glu Leu Val Arg Ile Lys Ala Lys Met Asn Trp Gly Leu Asn Asp
            740                 745                 750
Glu Leu Lys Lys Ala Phe Pro Glu Asn Ile Ser Lys Glu Arg Pro Leu
        755                 760                 765
Ile Asn Lys Asn Ile Pro Asn Phe Lys Trp Leu Ala Gly Phe Thr Ala
770                 775                 780
Gly Asp Gly His Phe Gly Val Asn Leu Lys Lys Val Lys Gly Thr Ala
785                 790                 795                 800
Lys Val Tyr Val Gly Leu Arg Phe Ala Ile Ser Gln His Ile Arg Asp
                805                 810                 815
Lys Asn Leu Met Asn Ser Leu Ile Thr Tyr Leu Gly Cys Gly Ser Ile
            820                 825                 830
Arg Glu Lys Asn Lys Ser Glu Phe Arg Trp Leu Glu Phe Glu Val Thr
        835                 840                 845
Lys Phe Ser Asp Ile Asn Asp Lys Ile Ile Pro Val Phe Gln Glu Asn
    850                 855                 860
Thr Leu Ile Gly Val Lys Leu Glu Asp Phe Glu Asp Trp Cys Lys Val
865                 870                 875                 880
Ala Lys Leu Ile Glu Glu Lys Lys His Leu Thr Glu Ser Gly Leu Asp
                885                 890                 895
Glu Ile Lys Lys Ile Lys Leu Asn Met Asn Lys Gly Arg
            900                 905
```

<210> SEQ ID NO 13
<211> LENGTH: 2634
<212> TYPE: RNA
<213> ORGANISM: Artificial Sequence
<220> FEATURE:
<223> OTHER INFORMATION: Synthesized I-OnuI variant megaTAL construct

<400> SEQUENCE: 13

```
augggauccg cgccaccuaa gaagaaacgc aaagucgugg aucuacgcac gcucggcuac      60
agucagcagc agcaagagaa gaucaaaccg aaggugcguu cgacaguggc gcagcaccac     120
gaggcacugg ugggccaugg uuuacacac gcgcacaucg uugcgcucag ccaacacccg      180
gcagcguuag ggaccgucgc ugucacguau cagcacauaa ucacggcguu gccagaggcg     240
acacacgaag acaucguugg cgucggcaaa caguggccg cgcacgcgc ccuggaggcc       300
uugcucacgg augcggggga uugagaggu ccgccguuac aguuggacac aggccaacuu      360
gugaagauug caaaacgugg cggcugacc gcaauggagg cagucaugc aucgcgcaau       420
gcacugacgg gugccccccu gaaccugacc ccggaccaag uggugcuau cgccagcaac     480
```

|   |   |
|---|---|
| auuggcggca agcaagcgcu cgaaacggug cagcggcugu ugccggugcu gugccaggac | 540 |
| cauggccuga ccccggacca aguggugggcu aucgccagca acauuggcgg caagcaagcg | 600 |
| cucgaaacgg ugcagcggcu guugccggug cugugccagg accauggccu gaccccggac | 660 |
| caaguggugg cuaucgccag caacauuggc ggcaagcaag cgcucgaaac ggugcagcgg | 720 |
| cuguugccgg ugcugugcca ggaccauggc cugaccccgg accaguggu ggcuaucgcc | 780 |
| agcaacggug gcggcaagca agcgcucgaa acggugcagc ggcuguugcc ggugcugugc | 840 |
| caggaccaug gccugacucc ggaccaagug guggcuaucg ccagccacga uggcggcaag | 900 |
| caagcgcucg aaacggugca gcggcuguug ccggugcugu gccaggacca uggccugacu | 960 |
| ccggaccaag uggugggcuau cgccagccac gauggcggca agcaagcgcu cgaaacggug | 1020 |
| cagcggcugu ugccggugcu gugccaggac cauggccuga ccccggacca aguggugggcu | 1080 |
| aucgccagca acauuggcgg caagcaagcg cucgaaacgg ugcagcggcu guugccggug | 1140 |
| cugugccagg accauggccu gaccccggac caaguggugg cuaucgccag caacauggc | 1200 |
| ggcaagcaag cgcucgaaac ggugcagcgg cuguugccgg ugcugugcca ggaccauggc | 1260 |
| cugaccccgg accaguggu ggcuaucgcc agcaacggug gcggcaagca agcgcucgaa | 1320 |
| acggugcagc ggcuguugcc ggugcugugc caggaccaug gccugacccc ggaccaagug | 1380 |
| guggcuaucg ccagcaacaa uggcggcaag caagcgcucg aaacggugca gcggcuguug | 1440 |
| ccggugcugu gccaggacca uggccugacc ccggaccaag uggugggcuau cgccagcaac | 1500 |
| auuggcggca agcaagcgcu cgaaagcauu guggcccagc ugagccggcc ugauccggcg | 1560 |
| uuggccgcgu ugaccaacga ccaccucguc gccuuggccu gccucggcgg acguccugcc | 1620 |
| auggaugcag ugaaaaaggg auugccgcac gcgccggaau ugaucagaag agucaaucgc | 1680 |
| cguauuggcg aacgcacguc ccaucgcguu gcgauaucua gaguggagg aagcucgcgc | 1740 |
| agagaguccaa ucaacccaug gauucugacu gguuucgcug augccgaagg aucauucaua | 1800 |
| cuagacaucc gcaaccgaaa caacgaaagc aacagauacc gaacuucgcu gagauuccag | 1860 |
| aucacccugc acaacaagga caaaucgauu cuggagaaua uccagucgac uuggaagguc | 1920 |
| ggcaagauca caaacagcgg cgacagagcc gucaugcuga gggucacccg uuucgaagau | 1980 |
| uugaaaguga uuaucgacca cuucgagaaa uauccgcuga uuacccagaa auugggcgau | 2040 |
| uacaaguugu uuaaacaggc auucagcguc auggagaaca agaacaucuc uaaggagaau | 2100 |
| gggauuaagg agcucguacg aaucaaagcu aagaugaauu ggggucucac ugacgaauug | 2160 |
| aaaaaagcau uccagagaa cauuagcaaa gagcgcccccc uuaucaauaa gaacauuccg | 2220 |
| aauuucaaau ggcuggcugg auucacaucu ggugauggc acuucggcgu gaaucuaaaa | 2280 |
| aagguaaagg gcaacgcaaa gguauacgug ggacugagau ucucaaucuc acagcacauc | 2340 |
| agagacaaga accugaugaa uucauugaua acauaccuag gcuguggguc caucugggag | 2400 |
| aagaacaagu cugaguucag uuggcucgag uucgucguaa ccaaauucag cgauaucaac | 2460 |
| gacaagauca uuccgguauu ccaggaaaau acucugauug gcgucaaacu cgaggacuuu | 2520 |
| gaagauuggu gcaagguugc caaauugauc gaagagaaga acaccugac cgaauccggu | 2580 |
| uuggaugaga uuaagaaau caagcugaac augaacaaag gucgugucuu cuga | 2634 |

<210> SEQ ID NO 14
<211> LENGTH: 2634
<212> TYPE: RNA
<213> ORGANISM: Artificial Sequence
<220> FEATURE:
<223> OTHER INFORMATION: Synthesized megaTAL construct

<400> SEQUENCE: 14

```
augggauccg cgccaccuaa gaagaaacgc aaagucgugg aucuacgcac gcucggcuac      60
agucagcagc agcaagagaa gaucaaaccg aaggugcguu cgacaguggc gcagcaccac     120
gaggcacugg ugggccaugg guuuacacac gcgcacaucg uugcgcucag ccaacacccg     180
gcagcguuag ggaccgucgc ugucacguau cagcacauaa ucacggcguu gccagaggcg     240
acacacgaag acaucguugg cgucggcaaa caguguccg cgcacgcgc ccuggaggcc       300
ugcucacgg augcggggga guugagaggu ccgccguuac aguugacac aggccaacuu       360
gugaagauug caaaacgugg cggcgugacc gcaauggagg cagugcaugc aucgcgcaau     420
gcacugacgg gugcccccu gaaccugacc ccggaccaag ugguggcuau cgccagcaac      480
auuggcggca agcaagcgcu cgaaacggug cagcggcugu gccggugcu ugccaggac       540
cauggccuga ccccggacca aguggugcu aucgccagca acauuggcgg caagcaagcg      600
cucgaaacgg ugcagcggcu guugccggug cugugccagg accauggccu gaccccggac     660
caaguggugg cuaucgccag caacauuggc ggcaagcaag cgcucgaaac ggugcagcgg     720
cuguugccgg ugcugugcca ggaccauggc ugaccccgg accaaguggu ggcuaucgcc       780
agcaacggug gcggcaagca agcgcucgaa acggugcagc ggcuguugcc ggugcugugc      840
caggaccaug gccugacucc ggaccaagug guggcuaucg ccagccacga uggcggcaag      900
caagcgcucg aaacggugca gcggcuguug ccggugcugu gccaggacca uggccugacu      960
ccggaccaag ugguggcuau cgccagccac gauggcggca agcaagcgcu cgaaacggug    1020
cagcggcugu gccggugcu gugccaggac cauggccuga ccccggacca agugguggcu    1080
aucgccagca cauuggcgg caagcaagcg cucgaaacgg ugcagcggcu guugccggug     1140
cugugccagg accauggccu gaccccggac caaguggugg cuaucgccag caacaauggc    1200
ggcaagcaag cgcucgaaac ggugcagcgg cuguugccgg ugcugugcca ggaccauggc    1260
cugaccccgg accaaguggu ggcuaucgcc agcaacggug gcggcaagca agcgcucgaa    1320
acggugcagc ggcuguugcc ggugcugugc caggaccaug gccugacccc ggaccaagug    1380
guggcuaucg ccagcaacaa uggcggcaag caagcgcucg aaacggugca gcggcuguug    1440
ccggugcugu gccaggacca uggccugacc ccggaccaag ugguggcuau cgccagcaac    1500
auuggcggca agcaagcgcu cgaaagcauu guggcccagc ugagccggcc ugauccggcg    1560
uuggccgcgu ugaccaacga ccaccucguc gccuuggccu gccucggcgg acguccugcc    1620
auggaugcag ugaaaaaggg auugccgcac gcgccggaau ugaucagaag agucaaucgc    1680
cguauuggcg aacgcacguc ccaucgcguu gcgauaucua gagugggagg aagcucgcgc    1740
agagagucca ucaacccaug gauucugacu gguuucgcug augccgaagg aucauucaua    1800
cuagacaucc gcaaccgaaa caacgaaagc aacagauacc gaacuucgcu gagauuccag    1860
aucacccugc acaacaagga caaaucgauu cuggagaaua uccagccac uuggaagguc     1920
ggcaagauca caaacagcag ugacagagcc gucaugcuga gggucacccg uuucgaagau    1980
uugaaaguga uuaucgacca cuucgagaaa uauccgcuga uuaccagaa auugggcgau    2040
uacaaguugu uuaaacaggc auucagcguc auggagaaua agaacaucu uaaggagaau    2100
gggauuaagg agcucguacg aaucaaagcu aagaugaauu ggggucucaa ugacgaauug    2160
aaaaaagcau uccagagaa cauuagcaaa gagcgccccc uuaucaauaa gaacauuccg    2220
aauuucaaau ggcuggcugg auucacagcu ggugaaggcc auucggcgu gaaucuaaaa    2280
```

| | |
|---|---|
| aagguaaagg gcaccgcaaa gguauacgug ggacugagau ucgcuaucuc acagcacauc | 2340 |
| agagacaaga accugaugaa uucauugaua acauaccuag gcugugguuc caucagagag | 2400 |
| aagaacaagu cugaguucag auggcucgag uucgaaguaa ccaaauucag cgauaucaac | 2460 |
| gacaagauca uuccgguauu ccaggaaaau acucugauug gcgucaaacu cgaggacuuu | 2520 |
| gaagauuggu gcaagguugc caaauugauc gaagagaaga aacaccugac cgaauccggu | 2580 |
| uuggaugaga uuaagaaaau caagcugaac augaacaaag gucgugucuu cuga | 2634 |

```
<210> SEQ ID NO 15
<211> LENGTH: 2628
<212> TYPE: RNA
<213> ORGANISM: Artificial Sequence
<220> FEATURE:
<223> OTHER INFORMATION: Synthesized megaTAL construct

<400> SEQUENCE: 15
```

| | |
|---|---|
| augggauccg cgccaccuaa gaagaaacgc aaagucgugg aucuacgcac gcucggcuac | 60 |
| agucagcagc agcaagagaa gaucaaaccg aaggugcguu cgacaguggc gcagcaccac | 120 |
| gaggcacugg ugggccaugg guuuacacac gcgcacaucg uugcgcucag ccaacacccg | 180 |
| gcagcguuag ggaccgucgc ugucacguau cagcacauaa ucacggcguu gccagaggcg | 240 |
| acacacgaag acaucguugg cgucggcaaa caguggaccg gcgcacgcgc ccuggaggcc | 300 |
| uugcucacgg augcggggga guugagaggu ccgccguuac aguuggacac aggccaacuu | 360 |
| gugaagauug caaaacgugg cggcgugacc gcaauggagg cagugcaugc aucgcgcaau | 420 |
| gcacugacgg gugccccccu gaaccugacc ccggaccaag uggugccuau cgccagcaac | 480 |
| auuggcggca agcaagcgcu cgaaacggug cagcggcugu ugccggugcu gugccaggac | 540 |
| cauggccuga ccccggacca aguggugcu aucgccagca cauuggcgg caagcaagcg | 600 |
| cucgaaacgg ugcagcggcu guugccggug cugugccagg accauggccu gaccccggac | 660 |
| caaguggugg cuaucgccag caacauuggc ggcaagcaag cgcucgaaac ggugcagcgg | 720 |
| cuguugccgg ugcugugcca ggaccauggc cugaccccgg accaaguggu ggcuaucgcc | 780 |
| agcaacggug gcggcaagca agcgcucgaa acggugcagc ggcuguugcc ggugcugugc | 840 |
| caggaccaug gccugacucc ggaccaagug guggcuaucg ccagccacga uggcggcaag | 900 |
| caagcgcucg aaacggugca gcggcuguug ccggugcugu gccaggacca uggccugacu | 960 |
| ccggaccaag uggugcuau cgccagccac gauggcggca agcaagcgcu cgaaacggug | 1020 |
| cagcggcugu ugccggugcu gugccaggac cauggccuga ccccggacca aguggugcu | 1080 |
| aucgccagca cauuggcgg caagcaagcg cucgaaacgg ugcagcggcu guugccggug | 1140 |
| cugugccagg accauggccu gaccccggac caaguggugg cuaucgccag caacauggc | 1200 |
| ggcaagcaag cgcucgaaac ggugcagcgg cuguugccgg ugcugugcca ggaccauggc | 1260 |
| cugaccccgg accaaguggu ggcuaucgcc agcaacggug gcggcaagca agcgcucgaa | 1320 |
| acggugcagc ggcuguugcc ggugcugugc caggaccaug gccugacccc ggaccaagug | 1380 |
| guggcuaucg ccagcaacaa uggcggcaag caagcgcucg aaacggugca gcggcuguug | 1440 |
| ccggugcugu gccaggacca uggccugacc ccggaccaag uggugcuau cgccagcaac | 1500 |
| auuggcggca agcaagcgcu cgaaagcauu guggcccagc ugagccggcc ugauccggcg | 1560 |
| uuggccgcgu ugaccaacga ccaccucguc gccuuggccu ggccucggcg acguccugcc | 1620 |
| auggaugcag ugaaaagggg auugccgcac gcgccggaau ugaucagaag agucaaucgc | 1680 |
| cguauuggcg aacgcacguc ccaucgcguu gcgauaucua gaguggagg aagcucgcgc | 1740 |

```
agagagucca ucaacccaug gauucugacu gguuucgcug augccgaagg aucauucaua    1800
cuagacaucc gcaaccgaaa caacgaaagc aacagauacc gaacuucgcu gagauuccag    1860
aucacccugc acaacaagga caaaucgauu cuggagaaua uccagccac uuggaagguc     1920 ggcaagauca caaacagcag ugacagagcc gucaugcuga gggucacccg uuucgaagau    1980
uugaaaguga uuaucgacca cuucgagaaa uauccgcuga uacccagaa auugggcgau     2040 uacaaguugu uuaaacaggc auucagcguc auggagaaua agaacaucu uaaggagaau     2100 gggauuaagg agcucguacg aaucaaagcu aagaugaauu ggggucucaa ugacgaauug    2160 aaaaagcau uuccagagaa cauuagcaaa gagcgccccc uuaucaauaa gaacauuccg     2220
aauuucaaau ggcuggcugg auucacagcu ggugauggcc auuucggcgu gaaucuaaaa    2280
aagguaaagg gcaccgcaaa gguauacgug ggacugagau cgcuaucuc acagcacauc     2340 agagacaaga accugaugaa uucauugaua acauaccuag gcugugguuc caucagagag    2400
aagaacaagu cugaguucag auggcucgag uucgaaguaa ccaaauucag cgauaucaac    2460
gacaagauca uuccgguauu ccaggaaaau acucugauug gcgucaaacu cgaggacuuu    2520
gaagauuggu gcaagguugc caaauugauc gaagagaaga acaccugac cgaauccggu     2580 uuggaugaga uuaagaaaau caagcugaac augaacaaag gucguuga              2628

<210> SEQ ID NO 16
<211> LENGTH: 2733
<212> TYPE: RNA
<213> ORGANISM: Artificial Sequence
<220> FEATURE:
<223> OTHER INFORMATION: Synthesized megaTAL construct

<400> SEQUENCE: 16
augggauccg cccucccgaa gaagaagcgg aaagucgugg accuccggac ccugggguuac    60 ucucagcagc agcaggagaa gaucaagccg aaggugcggu cgacugugc ccagcaucac    120 gaggcccugg ugggacacgg cuucacccac gcccacauug uggcccugag ccagcacccg    180
gcagcgcugg gaaccgcugc cgugaccuac cagcacauca uuacugcccu gccugaagcg    240
acccacgagg auaucguggg cgucggaaag caguggccg gagccagagc cuuggaggcu    300
cugcugacug acgccggaga gcugcgggc ccgccccugc aacuggauac cggccagcuc    360
gugaaaaucg ccaagagagg aggagugacc gccauggaag ccgugcaugc aucccgcaau    420
gcacugacug gugcaccccu gaaccucacu ccugaccagg ucgucgcuau cgcaagcaac    480
aucggaggga aacaagcucu cgagacagug cagcgccucc ugccagugcu ugccaggac    540 cacggccuga ccagacca ggugguuucgcu auugcgucga acauugagg gaagcaagcc     600 cuugaaaccg ugcagaggcu gcucccggug cugugccaag accauggacu caccccggac    660
caagugguug cuauugcuag caacauuggc gguaagcagg cgcuggagac agcccagcgg    720
cugcugccgg uguuugccca agaucacggu cuuaccccag accaagucgu ggcgauugcc    780
uccaacgguu gcggcaagca agcacucgaa acuguccaga acugcucccc ugugcucugu    840
caagaccacg gguugacccc cgaccaagug guggccaucg ccucccauga uggaggaaag    900
caggcccucg agacugucca gcgacugcuc ccgcguuguu gucaggauca uggauugacg    960
cccgaucagg ucguggccau ugccucccac gacgguggaa agcaagcgcu ggaaacugug    1020
cagcgguugc ugccguccuu gugccaggac acggacuga ucccgaccca gguggucgcc    1080
aucgcaucca cauugguggg caagcaggcu cucgaaaccg uccaacgccu guugccggug    1140
```

```
cugugucagg aucauggacu gaccccggac caagugguqg cuaucgccuc caacaacggg    1200
ggcaaacagg cccuggaaac cgugcaacgc cugcugcccg uccucugcca ggaccacggu    1260
cugaccccug accaggucgu cgcgaucgcg ucaaaugggg ggggcaaaca ggcucuggaa    1320
acggugcagc gguccuucc gguguuaugc caggaccacg ggcugacucc cgaccaggug     1380
guggcgaucg ccucgaacaa cggaggcaaa caagcccugg agacugugca gagaccccug    1440
cccgugcugu gccaagacca ugggcucacc ccugaucagg ugguggcaau cgccucaaac    1500
aucggcggga agcaggcacu ggaaacugug cagagacucc ugcccgugcu gugccaagac    1560
caugggcuga ccccggacca aguguggcu aucgccuccc acgacggggg caaacaggcc     1620
cuggaaucca ucgucgcuca gcugagccgg ccugacccag cacucgccgc ccugaccaau    1680
gaccaucugg ucgcccuggc cugccuggga ggcagacccg cgauggacgc ggucaagaag    1740
ggucugccgc acgcccuga gcuuauucgg agagugaaca ggcgcaucgg ugaacgcacc     1800
ucccaucggg ucgcaaucuc uagaguggc ggaucguccc ggcgggaguc caucaauccu     1860
uggauccuga ccggcuucgc cgacgccgaa ggccuccuuca uccuggacau caggaacagg    1920
aacaacgagu caaacaggua ccgcaccucc cuucgguucc agauuacucu gcacaacaag    1980
gauaagucca uccucgagaa cauccaguca accuggaaaa ugggcaagau cacuaacucc    2040
ucggaccgcg cagugaugcu ccgggugacc cgcuucgagg accugaaggu gaucauugac    2100
cacuucgaga aguacccucu cauaacccag aagcugggag auuacaagcu guuuaagcag    2160
gcguucuccg ugauggagaa caaagaacac cuuaaggaga augggauuaa ggaacuqguc    2220 cgcauuaagg ccaagaugaa cuggggacug aacgacgagu ugaaaaaggc auuccugaa     2280 aacaucucca aggaacggcc gcucaucaac aagaacauuc ccaauuucaa guggcuggcg    2340
ggguucacug ccggggacgg acacuucgga gugaaccuga agaaggugaa gggcaccgcc    2400
aagguguacg ugggccugcg guucgcgauc agccagcaca uccgggauaa gaaccugaug    2460
aacagccuca ucaccuaccu gggaugcgga agcauccggg agaagaacaa gucagaauuc    2520
cgauggcugg aauuugaagu gaccaaguuc uccgacauca cgacaagau caucccgug     2580 uuccaggaga acacccucau uggagugaag cuggaggacu cgaggacug gugcaaggug    2640 gccaagcuca ucgaagagaa gaagcaccug accgaaagcg gccuggauga gauuaagaag    2700
auuaagcuca acaugaacaa gggaagauag uag                                 2733
```

<210> SEQ ID NO 17
<211> LENGTH: 22
<212> TYPE: DNA
<213> ORGANISM: Homo sapiens
<400> SEQUENCE: 17
tgtctgccta ttcaccgatt tt                                              22

<210> SEQ ID NO 18
<211> LENGTH: 11
<212> TYPE: DNA
<213> ORGANISM: Homo sapiens
<400> SEQUENCE: 18
aaatccagtg a                                                          11

<210> SEQ ID NO 19
<211> LENGTH: 12
<212> TYPE: DNA
<213> ORGANISM: Homo sapiens

<400> SEQUENCE: 19
aaatccagtg ac                                                          12

<210> SEQ ID NO 20
<211> LENGTH: 39
<212> TYPE: DNA
<213> ORGANISM: Homo sapiens

<400> SEQUENCE: 20
aaatccagtg acaagtctgt ctgcctattc accgatttt                             39

<210> SEQ ID NO 21
<211> LENGTH: 22
<212> TYPE: DNA
<213> ORGANISM: Homo sapiens

<400> SEQUENCE: 21
agtatgccta ttctacaaga aa                                               22

<210> SEQ ID NO 22
<211> LENGTH: 877
<212> TYPE: PRT
<213> ORGANISM: Artificial Sequence
<220> FEATURE:
<223> OTHER INFORMATION: Synthesized NTD variant megaTAL construct

<400> SEQUENCE: 22

Met Gly Ser Ala Pro Lys Lys Arg Lys Val Gly Lys Leu Cys
1               5                   10                  15

Thr Leu Gly Tyr Ser Gln Gln Gln Glu Lys Leu Lys Leu Lys Ala
                20                  25                  30

Arg Pro Ile Val Ala Gln His His Glu Ala Leu Ile Gly His Gly Phe
            35                  40                  45

Thr Arg Ala Gln Ile Val Ala Leu Ser Gln His Pro Ala Ala Leu Gly
        50                  55                  60

Thr Ile Ala Ala Lys Tyr Gln Ala Met Ile Ala Ala Leu Pro Glu Ala
65                  70                  75                  80

Thr His Glu Asp Val Val Gly Ile Gly Lys Gln Trp Ser Gly Ala Arg
                85                  90                  95

Thr Leu Glu Val Leu Leu Thr Val Ser Gly Glu Leu Arg Ser Pro Pro
            100                 105                 110

Leu Gln Leu Asp Thr Ser Gln Leu Leu Lys Ile Ala Lys Arg Gly Gly
        115                 120                 125

Val Thr Ala Ile Glu Ala Val His Ala Trp Arg Asn Ala Leu Thr Gly
    130                 135                 140

Ala Pro Leu Asn Leu Thr Pro Asp Gln Val Val Ala Ile Ala Ser Asn
145                 150                 155                 160

Ile Gly Gly Lys Gln Ala Leu Glu Thr Val Gln Arg Leu Leu Pro Val
                165                 170                 175

Leu Cys Gln Asp His Gly Leu Thr Pro Asp Gln Val Val Ala Ile Ala
            180                 185                 190

Ser Asn Ile Gly Gly Lys Gln Ala Leu Glu Thr Val Gln Arg Leu Leu
        195                 200                 205

Pro Val Leu Cys Gln Asp His Gly Leu Thr Pro Asp Gln Val Val Ala
    210                 215                 220

Ile Ala Ser Asn Ile Gly Gly Lys Gln Ala Leu Glu Thr Val Gln Arg
225                 230                 235                 240

```
Leu Leu Pro Val Leu Cys Gln Asp His Gly Leu Thr Pro Asp Gln Val
            245                 250                 255

Val Ala Ile Ala Ser Asn Gly Gly Lys Gln Ala Leu Glu Thr Val
        260                 265                 270

Gln Arg Leu Leu Pro Val Leu Cys Gln Asp His Gly Leu Thr Pro Asp
            275                 280                 285

Gln Val Val Ala Ile Ala Ser His Asp Gly Gly Lys Gln Ala Leu Glu
        290                 295                 300

Thr Val Gln Arg Leu Leu Pro Val Leu Cys Gln Asp His Gly Leu Thr
305                 310                 315                 320

Pro Asp Gln Val Val Ala Ile Ala Ser His Asp Gly Gly Lys Gln Ala
                325                 330                 335

Leu Glu Thr Val Gln Arg Leu Leu Pro Val Leu Cys Gln Asp His Gly
                340                 345                 350

Leu Thr Pro Asp Gln Val Val Ala Ile Ala Ser Asn Ile Gly Gly Lys
                355                 360                 365

Gln Ala Leu Glu Thr Val Gln Arg Leu Leu Pro Val Leu Cys Gln Asp
        370                 375                 380

His Gly Leu Thr Pro Asp Gln Val Val Ala Ile Ala Ser Asn Asn Gly
385                 390                 395                 400

Gly Lys Gln Ala Leu Glu Thr Val Gln Arg Leu Leu Pro Val Leu Cys
                405                 410                 415

Gln Asp His Gly Leu Thr Pro Asp Gln Val Val Ala Ile Ala Ser Asn
                420                 425                 430

Gly Gly Gly Lys Gln Ala Leu Glu Thr Val Gln Arg Leu Leu Pro Val
            435                 440                 445

Leu Cys Gln Asp His Gly Leu Thr Pro Asp Gln Val Val Ala Ile Ala
        450                 455                 460

Ser Asn Asn Gly Gly Lys Gln Ala Leu Glu Thr Val Gln Arg Leu Leu
465                 470                 475                 480

Pro Val Leu Cys Gln Asp His Gly Leu Thr Pro Asp Gln Val Val Ala
                485                 490                 495

Ile Ala Ser Asn Ile Gly Gly Lys Gln Ala Leu Glu Ser Ile Val Ala
            500                 505                 510

Gln Leu Ser Arg Pro Asp Pro Ala Leu Ala Ala Leu Thr Asn Asp His
        515                 520                 525

Leu Val Ala Leu Ala Cys Leu Gly Gly Arg Pro Ala Met Asp Ala Val
        530                 535                 540

Lys Lys Gly Leu Pro His Ala Pro Glu Leu Ile Arg Arg Val Asn Arg
545                 550                 555                 560

Arg Ile Gly Glu Arg Thr Ser His Arg Val Ala Ile Ser Arg Val Gly
                565                 570                 575

Gly Ser Ser Arg Arg Glu Ser Ile Asn Pro Trp Ile Leu Thr Gly Phe
            580                 585                 590

Ala Asp Ala Glu Gly Ser Phe Ile Leu Asp Ile Arg Asn Arg Asn Asn
        595                 600                 605

Glu Ser Asn Arg Tyr Arg Thr Ser Leu Arg Phe Gln Ile Thr Leu His
        610                 615                 620

Asn Lys Asp Lys Ser Ile Leu Glu Asn Ile Gln Ser Thr Trp Lys Val
625                 630                 635                 640

Gly Lys Ile Thr Asn Ser Gly Asp Arg Ala Val Met Leu Arg Val Thr
                645                 650                 655
```

```
Arg Phe Glu Asp Leu Lys Val Ile Ile Asp His Phe Glu Lys Tyr Pro
            660                 665                 670

Leu Ile Thr Gln Lys Leu Gly Asp Tyr Lys Leu Phe Lys Gln Ala Phe
        675                 680                 685

Ser Val Met Glu Asn Lys Glu His Leu Lys Glu Asn Gly Ile Lys Glu
    690                 695                 700

Leu Val Arg Ile Lys Ala Lys Met Asn Trp Gly Leu Thr Asp Glu Leu
705                 710                 715                 720

Lys Lys Ala Phe Pro Glu Asn Ile Ser Lys Glu Arg Pro Leu Ile Asn
                725                 730                 735

Lys Asn Ile Pro Asn Phe Lys Trp Leu Ala Gly Phe Thr Ser Gly Asp
            740                 745                 750

Gly Tyr Phe Gly Val Asn Leu Lys Lys Val Lys Gly Asn Ala Lys Val
        755                 760                 765

Tyr Val Gly Leu Arg Phe Ser Ile Ser Gln His Ile Arg Asp Lys Asn
770                 775                 780

Leu Met Asn Ser Leu Ile Thr Tyr Leu Gly Cys Gly Ser Ile Trp Glu
785                 790                 795                 800

Lys Asn Lys Ser Glu Phe Ser Trp Leu Glu Phe Val Val Thr Lys Phe
                805                 810                 815

Ser Asp Ile Asn Asp Lys Ile Ile Pro Val Phe Gln Glu Asn Thr Leu
            820                 825                 830

Ile Gly Val Lys Leu Glu Asp Phe Glu Asp Trp Cys Lys Val Ala Lys
        835                 840                 845

Leu Ile Glu Glu Lys Lys His Leu Thr Glu Ser Gly Leu Asp Glu Ile
850                 855                 860

Lys Lys Ile Lys Leu Asn Met Asn Lys Gly Arg Val Phe
865                 870                 875

<210> SEQ ID NO 23
<211> LENGTH: 877
<212> TYPE: PRT
<213> ORGANISM: Artificial Sequence
<220> FEATURE:
<223> OTHER INFORMATION: Synthesized NTD variant megaTAL construct

<400> SEQUENCE: 23

Met Gly Ser Ala Pro Pro Lys Lys Lys Arg Lys Val Val Asp Leu Ser
1               5                   10                  15

Thr Phe Gly Tyr Ser Gln Gln Gln Glu Lys Ile Lys Pro Lys Val
            20                  25                  30

Arg Ser Thr Val Ala Gln His His Ala Ala Leu Val Gly His Gly Phe
        35                  40                  45

Thr His Ala His Ile Val Glu Leu Ser Lys His Pro Pro Ala Leu Gly
    50                  55                  60

Thr Ile Ala Ala Arg Tyr Ser Glu Met Ile Ala Ala Leu Pro Glu Ala
65                  70                  75                  80

Thr His Glu Asp Ile Val Gly Val Gly Lys His Cys Ala Gly Ala Arg
                85                  90                  95

Thr Leu Glu Val Leu Leu Met Val Val Gln Glu Leu Arg Ala Pro Pro
            100                 105                 110

Leu Gln Leu Val Thr Ser Gln Leu Leu Lys Ile Ala Lys Arg Gly Gly
        115                 120                 125

Val Thr Ala Val Glu Ala Val His Ala Ser Arg Asn Ala Leu Thr Gly
    130                 135                 140
```

```
Ala Pro Leu Asn Leu Thr Pro Asp Gln Val Val Ala Ile Ala Ser Asn
145                 150                 155                 160

Ile Gly Gly Lys Gln Ala Leu Glu Thr Val Gln Arg Leu Leu Pro Val
                165                 170                 175

Leu Cys Gln Asp His Gly Leu Thr Pro Asp Gln Val Val Ala Ile Ala
            180                 185                 190

Ser Asn Ile Gly Gly Lys Gln Ala Leu Glu Thr Val Gln Arg Leu Leu
        195                 200                 205

Pro Val Leu Cys Gln Asp His Gly Leu Thr Pro Asp Gln Val Val Ala
    210                 215                 220

Ile Ala Ser Asn Ile Gly Gly Lys Gln Ala Leu Glu Thr Val Gln Arg
225                 230                 235                 240

Leu Leu Pro Val Leu Cys Gln Asp His Gly Leu Thr Pro Asp Gln Val
                245                 250                 255

Val Ala Ile Ala Ser Asn Gly Gly Lys Gln Ala Leu Glu Thr Val
            260                 265                 270

Gln Arg Leu Leu Pro Val Leu Cys Gln Asp His Gly Leu Thr Pro Asp
            275                 280                 285

Gln Val Val Ala Ile Ala Ser His Asp Gly Lys Gln Ala Leu Glu
    290                 295                 300

Thr Val Gln Arg Leu Leu Pro Val Leu Cys Gln Asp His Gly Leu Thr
305                 310                 315                 320

Pro Asp Gln Val Val Ala Ile Ala Ser His Asp Gly Gly Lys Gln Ala
                325                 330                 335

Leu Glu Thr Val Gln Arg Leu Leu Pro Val Leu Cys Gln Asp His Gly
            340                 345                 350

Leu Thr Pro Asp Gln Val Val Ala Ile Ala Ser Asn Ile Gly Gly Lys
        355                 360                 365

Gln Ala Leu Glu Thr Val Gln Arg Leu Leu Pro Val Leu Cys Gln Asp
    370                 375                 380

His Gly Leu Thr Pro Asp Gln Val Val Ala Ile Ala Ser Asn Asn Gly
385                 390                 395                 400

Gly Lys Gln Ala Leu Glu Thr Val Gln Arg Leu Leu Pro Val Leu Cys
                405                 410                 415

Gln Asp His Gly Leu Thr Pro Asp Gln Val Val Ala Ile Ala Ser Asn
            420                 425                 430

Gly Gly Gly Lys Gln Ala Leu Glu Thr Val Gln Arg Leu Leu Pro Val
        435                 440                 445

Leu Cys Gln Asp His Gly Leu Thr Pro Asp Gln Val Val Ala Ile Ala
    450                 455                 460

Ser Asn Asn Gly Gly Lys Gln Ala Leu Glu Thr Val Gln Arg Leu Leu
465                 470                 475                 480

Pro Val Leu Cys Gln Asp His Gly Leu Thr Pro Asp Gln Val Val Ala
                485                 490                 495

Ile Ala Ser Asn Ile Gly Gly Lys Gln Ala Leu Glu Ser Ile Val Ala
            500                 505                 510

Gln Leu Ser Arg Pro Asp Pro Ala Leu Ala Ala Leu Thr Asn Asp His
        515                 520                 525

Leu Val Ala Leu Ala Cys Leu Gly Gly Arg Pro Ala Met Asp Ala Val
    530                 535                 540

Lys Lys Gly Leu Pro His Ala Pro Glu Leu Ile Arg Arg Val Asn Arg
545                 550                 555                 560

Arg Ile Gly Glu Arg Thr Ser His Arg Val Ala Ile Ser Arg Val Gly
```

```
                    565                 570                 575
Gly Ser Ser Arg Arg Glu Ser Ile Asn Pro Trp Ile Leu Thr Gly Phe
            580                 585                 590

Ala Asp Ala Glu Gly Ser Phe Ile Leu Asp Ile Arg Asn Arg Asn Asn
            595                 600                 605

Glu Ser Asn Arg Tyr Arg Thr Ser Leu Arg Phe Gln Ile Thr Leu His
            610                 615                 620

Asn Lys Asp Lys Ser Ile Leu Glu Asn Ile Gln Ser Thr Trp Lys Val
625                 630                 635                 640

Gly Lys Ile Thr Asn Ser Gly Asp Arg Ala Val Met Leu Arg Val Thr
            645                 650                 655

Arg Phe Glu Asp Leu Lys Val Ile Ile Asp His Phe Glu Lys Tyr Pro
            660                 665                 670

Leu Ile Thr Gln Lys Leu Gly Asp Tyr Lys Leu Phe Lys Gln Ala Phe
            675                 680                 685

Ser Val Met Glu Asn Lys Glu His Leu Lys Glu Asn Gly Ile Lys Glu
            690                 695                 700

Leu Val Arg Ile Lys Ala Lys Met Asn Trp Gly Leu Thr Asp Glu Leu
705                 710                 715                 720

Lys Lys Ala Phe Pro Glu Asn Ile Ser Lys Glu Arg Pro Leu Ile Asn
                725                 730                 735

Lys Asn Ile Pro Asn Phe Lys Trp Leu Ala Gly Phe Thr Ser Gly Asp
            740                 745                 750

Gly Tyr Phe Gly Val Asn Leu Lys Lys Val Lys Gly Asn Ala Lys Val
            755                 760                 765

Tyr Val Gly Leu Arg Phe Ser Ile Ser Gln His Ile Arg Asp Lys Asn
770                 775                 780

Leu Met Asn Ser Leu Ile Thr Tyr Leu Gly Cys Gly Ser Ile Trp Glu
785                 790                 795                 800

Lys Asn Lys Ser Glu Phe Ser Trp Leu Glu Phe Val Val Thr Lys Phe
                805                 810                 815

Ser Asp Ile Asn Asp Lys Ile Ile Pro Val Phe Gln Glu Asn Thr Leu
            820                 825                 830

Ile Gly Val Lys Leu Glu Asp Phe Glu Asp Trp Cys Lys Val Ala Lys
            835                 840                 845

Leu Ile Glu Glu Lys Lys His Leu Thr Glu Ser Gly Leu Asp Glu Ile
            850                 855                 860

Lys Lys Ile Lys Leu Asn Met Asn Lys Gly Arg Val Phe
865                 870                 875

<210> SEQ ID NO 24
<211> LENGTH: 877
<212> TYPE: PRT
<213> ORGANISM: Artificial Sequence
<220> FEATURE:
<223> OTHER INFORMATION: Synthesized NTD variant megaTAL construct

<400> SEQUENCE: 24

Met Gly Ser Ala Pro Pro Lys Lys Lys Arg Lys Val Gly Lys Leu Ser
1               5                   10                  15

Thr Phe Gly Tyr Ser Gln Gln Gln Glu Lys Ile Lys Pro Lys Ala
                20                  25                  30

Arg Ser Thr Val Ala Gln His His Ala Ala Leu Ile Gly His Gly Phe
            35                  40                  45

Thr His Ala His Ile Val Glu Leu Ser Lys His Pro Pro Ala Leu Gly
```

-continued

```
            50                  55                  60
Thr Ile Ala Ala Arg Tyr Ser Glu Met Ile Ala Ala Leu Pro Glu Ala
 65                  70                  75                  80

Thr His Glu Asp Ile Val Gly Val Gly Lys Gln Trp Ser Gly Ala Arg
                 85                  90                  95

Thr Leu Glu Val Leu Leu Met Val Val Gln Glu Leu Arg Ala Pro Pro
            100                 105                 110

Leu Gln Leu Val Thr Ser Gln Leu Val Lys Ile Ala Lys Arg Gly Gly
        115                 120                 125

Val Thr Ala Ile Glu Ala Val His Ala Ser Arg Asn Ala Leu Thr Gly
    130                 135                 140

Ala Pro Leu Asn Leu Thr Pro Asp Gln Val Val Ala Ile Ala Ser Asn
145                 150                 155                 160

Ile Gly Gly Lys Gln Ala Leu Glu Thr Val Gln Arg Leu Leu Pro Val
                165                 170                 175

Leu Cys Gln Asp His Gly Leu Thr Pro Asp Gln Val Val Ala Ile Ala
            180                 185                 190

Ser Asn Ile Gly Gly Lys Gln Ala Leu Glu Thr Val Gln Arg Leu Leu
        195                 200                 205

Pro Val Leu Cys Gln Asp His Gly Leu Thr Pro Asp Gln Val Val Ala
210                 215                 220

Ile Ala Ser Asn Ile Gly Gly Lys Gln Ala Leu Glu Thr Val Gln Arg
225                 230                 235                 240

Leu Leu Pro Val Leu Cys Gln Asp His Gly Leu Thr Pro Asp Gln Val
                245                 250                 255

Val Ala Ile Ala Ser Asn Gly Gly Lys Gln Ala Leu Glu Thr Val
            260                 265                 270

Gln Arg Leu Leu Pro Val Leu Cys Gln Asp His Gly Leu Thr Pro Asp
        275                 280                 285

Gln Val Val Ala Ile Ala Ser His Asp Gly Gly Lys Gln Ala Leu Glu
    290                 295                 300

Thr Val Gln Arg Leu Leu Pro Val Leu Cys Gln Asp His Gly Leu Thr
305                 310                 315                 320

Pro Asp Gln Val Val Ala Ile Ala Ser His Asp Gly Gly Lys Gln Ala
                325                 330                 335

Leu Glu Thr Val Gln Arg Leu Leu Pro Val Leu Cys Gln Asp His Gly
            340                 345                 350

Leu Thr Pro Asp Gln Val Val Ala Ile Ala Ser Asn Ile Gly Gly Lys
        355                 360                 365

Gln Ala Leu Glu Thr Val Gln Arg Leu Leu Pro Val Leu Cys Gln Asp
    370                 375                 380

His Gly Leu Thr Pro Asp Gln Val Val Ala Ile Ala Ser Asn Asn Gly
385                 390                 395                 400

Gly Lys Gln Ala Leu Glu Thr Val Gln Arg Leu Leu Pro Val Leu Cys
                405                 410                 415

Gln Asp His Gly Leu Thr Pro Asp Gln Val Val Ala Ile Ala Ser Asn
            420                 425                 430

Gly Gly Gly Lys Gln Ala Leu Glu Thr Val Gln Arg Leu Leu Pro Val
        435                 440                 445

Leu Cys Gln Asp His Gly Leu Thr Pro Asp Gln Val Val Ala Ile Ala
    450                 455                 460

Ser Asn Asn Gly Gly Lys Gln Ala Leu Glu Thr Val Gln Arg Leu Leu
465                 470                 475                 480
```

```
Pro Val Leu Cys Gln Asp His Gly Leu Thr Pro Asp Gln Val Val Ala
            485                 490                 495

Ile Ala Ser Asn Ile Gly Gly Lys Gln Ala Leu Glu Ser Ile Val Ala
            500                 505                 510

Gln Leu Ser Arg Pro Asp Pro Ala Leu Ala Ala Leu Thr Asn Asp His
            515                 520                 525

Leu Val Ala Leu Ala Cys Leu Gly Gly Arg Pro Ala Met Asp Ala Val
            530                 535                 540

Lys Lys Gly Leu Pro His Ala Pro Glu Leu Ile Arg Arg Val Asn Arg
545                 550                 555                 560

Arg Ile Gly Glu Arg Thr Ser His Arg Val Ala Ile Ser Arg Val Gly
            565                 570                 575

Gly Ser Ser Arg Arg Glu Ser Ile Asn Pro Trp Ile Leu Thr Gly Phe
            580                 585                 590

Ala Asp Ala Glu Gly Ser Phe Ile Leu Asp Ile Arg Asn Arg Asn Asn
            595                 600                 605

Glu Ser Asn Arg Tyr Arg Thr Ser Leu Arg Phe Gln Ile Thr Leu His
            610                 615                 620

Asn Lys Asp Lys Ser Ile Leu Glu Asn Ile Gln Ser Thr Trp Lys Val
625                 630                 635                 640

Gly Lys Ile Thr Asn Ser Gly Asp Arg Ala Val Met Leu Arg Val Thr
            645                 650                 655

Arg Phe Glu Asp Leu Lys Val Ile Ile Asp His Phe Glu Lys Tyr Pro
            660                 665                 670

Leu Ile Thr Gln Lys Leu Gly Asp Tyr Lys Leu Phe Lys Gln Ala Phe
            675                 680                 685

Ser Val Met Glu Asn Lys Glu His Leu Lys Glu Asn Gly Ile Lys Glu
            690                 695                 700

Leu Val Arg Ile Lys Ala Lys Met Asn Trp Gly Leu Thr Asp Glu Leu
705                 710                 715                 720

Lys Lys Ala Phe Pro Glu Asn Ile Ser Lys Glu Arg Pro Leu Ile Asn
            725                 730                 735

Lys Asn Ile Pro Asn Phe Lys Trp Leu Ala Gly Phe Thr Ser Gly Asp
            740                 745                 750

Gly Tyr Phe Gly Val Asn Leu Lys Lys Val Lys Gly Asn Ala Lys Val
            755                 760                 765

Tyr Val Gly Leu Arg Phe Ser Ile Ser Gln His Ile Arg Asp Lys Asn
            770                 775                 780

Leu Met Asn Ser Leu Ile Thr Tyr Leu Gly Cys Gly Ser Ile Trp Glu
785                 790                 795                 800

Lys Asn Lys Ser Glu Phe Ser Trp Leu Glu Phe Val Val Thr Lys Phe
            805                 810                 815

Ser Asp Ile Asn Asp Lys Ile Ile Pro Val Phe Gln Glu Asn Thr Leu
            820                 825                 830

Ile Gly Val Lys Leu Glu Asp Phe Glu Asp Trp Cys Lys Val Ala Lys
            835                 840                 845

Leu Ile Glu Glu Lys Lys His Leu Thr Glu Ser Gly Leu Asp Glu Ile
            850                 855                 860

Lys Lys Ile Lys Leu Asn Met Asn Lys Gly Arg Val Phe
865                 870                 875

<210> SEQ ID NO 25
<211> LENGTH: 2634
```

-continued

```
<212> TYPE: RNA
<213> ORGANISM: Artificial Sequence
<220> FEATURE:
<223> OTHER INFORMATION: Synthesized NTD variant megaTAL construct

<400> SEQUENCE: 25
augggauccg cgccaccuaa gaagaaacgc aaagucggca agcugugcac ccugggcuac      60
agccagcagc agcaggagaa gcugaagcug aaggccagac ccaucguggc ccagcaccac     120
gaggcccuga ucggccacgg cuucaccaga gcccagaucg uggcccugag ccagcacccc     180
gccgcccugg gcaccaucgc cgccaaguac caggccauga ucgccgcccu gcccgaggcc     240
acccacgagg acgugguggg caucggcaag caguggagcg gcgccagaac ccuggaggug     300
cuacugaccg ugagcggcga gcugagaagc cccccccugc agcuggacac cagccagcug     360
cugaagaucg ccaagagagg cggcgugacc gccaucgagg ccgugcacgc cuggcgcaau     420
gcacugacgg gugcccccu gaaccugacc ccggaccaag ugguggcuau cgccagcaac      480
auuggcggca agcaagcgcu cgaaacggug cagcggcugu ugccggugcu gugccaggac     540
cauggccuga ccccggacca aguggugcu aucgccagca acauuggcgg caagcaagcg      600
cucgaaacgg ugcagcggcu guugccggug cugugccagg accauggccu gaccccggac     660
caagugguag cuaucgccag caacauuggc ggcaagcaag cgcucgaaac ggugcagcgg     720
cuguugccgg ugcugugcca ggaccauggc cugaccccgg accaaguggu ggcuaucgcc     780
agcaacggug gcggcaagca agcgcucgaa acggugcagc ggcuguugcc ggugcugugc     840
caggaccaug gccugacucc ggaccaagug guggcuaucg ccagccacga uggcggcaag     900
caagcgcucg aaacggugca gcggcuguug ccggugcugu gccaggacca uggccugacu     960
ccggaccaag ugguggcuau cgccagccac gauggcggca agcaagcgcu cgaaacggug    1020
cagcggcugu ugccggugcu gugccaggac cauggccuga ccccggacca agugguggcu    1080
aucgccagca acauuggcgg caagcaagcg cucgaaacgg ugcagcggcu guugccggug    1140
cugugccagg accauggccu gaccccggac caaguggugg cuaucgccag caacaauggc    1200
ggcaagcaag cgcucgaaac ggugcagcgg cuguugccgg ugcugugcca ggaccauggc    1260
cugaccccgg accaaguggu ggcuaucgcc agcaacggug gcggcaagca agcgcucgaa    1320
acggugcagc ggcuguugcc ggugcugugc caggaccaug gccugacccc ggaccaagug    1380
guggcuaucg ccagcaacaa uggcggcaag caagcgcucg aaacggugca gcggcuguug    1440
ccggugcugu gccaggacca uggccugacc ccggaccaag ugguggcuau cgccagcaac    1500
auuggcggca agcaagcgcu cgaaagcauu guggcccagc ugagccggcc ugauccggcg    1560
uuggccgcgu ugaccaacga ccaccucguc gccuuggccu gccucggcgg acguccugcc    1620
auggaugcag ugaaaaaggg auugccgcac gcgccggaau ugaucagaag agucaaucgc    1680
cguauuggcg aacgcacguc ccaucgcguu gcgauaucua gagugggagg aagcucgcgc    1740
agagagucca ucaacccaug gauucugacu gguuucgcug augccgaagg aucauucaua    1800
cuagacaucc gcaaccgaaa caacgaaagc aacagauacc gaacuucgcu gagauuccag    1860
aucacccugc acaacaagga caaaucgauu cuggagaaua uccagucgac uuggaagguc    1920
ggcaagauca caaacagcgg cgacagagcc gucaugcuga gggucacccg uuucgaagau    1980
uugaaaguga uuaucgacca cuucgagaaa uauccgcuga uuacccagaa auugggcgau    2040
uacaaguugu uuaaacaggc auucagcguc auggagaaca aagaacaucu uaaggagaau    2100
gggauuaagg agcucguacg aaucaaagcu aagaugaauu ggggucucac ugacgaauug    2160
```

| | |
|---|---:|
| aaaaaagcau uuccagagaa cauuagcaaa gagcgccccc uuaucaauaa gaacauuccg | 2220 |
| aauuucaaau ggcuggcugg auucacaucu ggugauggcu acuucggcgu gaaucuaaaa | 2280 |
| aagguaaagg gcaacgcaaa ggguauacgug ggacugagau ucucaaucuc acagcacauc | 2340 |
| agagacaaga accugaugaa uucauugaua acauaccuag gcuguggu uc caucugggag | 2400 |
| aagaacaagu cugaguucag uuggcucgag uucgucguaa ccaaauucag cgauaucaac | 2460 |
| gacaagauca uuccgguauu ccaggaaaaau acucugauug cgucaaacu cgaggacuuu | 2520 |
| gaagauuggu gcaagguugc caaauugauc gaagagaaga aacaccugac cgaauccggu | 2580 |
| uuggaugaga uuaagaaaau caagcugaac augaacaaag gucgugucuu cuga | 2634 |

<210> SEQ ID NO 26
<211> LENGTH: 2634
<212> TYPE: RNA
<213> ORGANISM: Artificial Sequence
<220> FEATURE:
<223> OTHER INFORMATION: Synthesized NTD variant megaTAL construct

<400> SEQUENCE: 26

```
augggauccg cgccaccuaa gaagaaacgc aaagucgugg accugagcac cuucggcuac     60
agccagcagc agcaggagaa gaucaagccc aaggugagaa gcaccguggc ccagcaccac    120
gccgcccugg ugggccacgg cuucacccac gcccacaucg uggagcugag caagcacccc    180
cccgcccugg gcaccaucgc cgccagauac agcgagauga ucgccgcccu gcccgaggcc    240
acccacgagg acaucguggg cgugggcaag cacugcgccg gcgccagaac ccuggaggug    300
cugcugaugg uggugcagga gcugagagcu ccaccacugc agcuggugac cagccagcug    360
cugaagaucg ccaagagagg cggcgugacc gccguggagg ccgugcacgc cagccgcaau    420
gcacugacgg gugccccccu gaaccugacc ccggaccaag ugguggcuau cgccagcaac    480
auuggcggca agcaagcgcu cgaaacggug cagcggcugu ugccggugcu gugccaggac    540
cauggccuga ccccggacca agugguggcu aucgccagca acauuggcgg caagcaagcg    600
cucgaaacgg ugcagcggcu guugccggug cugugccagg accauggccu gaccccggac    660 caagguggugg cuaucgccag caacauuggc ggcaagcaag cgcucgaaac ggugcagcgg    720
cuguugccgg ugcugugcca ggaccauggc cugaccccgg accaaguggu ggcuaucgcc    780
agcaacggug gcggcaagca agcgcucgaa acggugcagc ggcuguugcc ggugcugugc    840
caggaccaug gccugacucc ggaccaagug guggcuaucg ccagccacga uggcggcaag    900
caagcgcucg aaacggugca gcggcuguug ccggugcugu gccaggacca uggccugacu    960
ccggaccaag ugguggcuau cgccagccac gauggcggca agcaagcgcu cgaaacggug   1020
cagcggcugu ugccggugcu gugccaggac cauggccuga ccccggacca agugguggcu   1080
aucgccagca acauuggcgg caagcaagcg cucgaaacgg ugcagcggcu guugccggug   1140
cugugccagg accauggccu gaccccggac caagugguggg cuaucgccag caacaauggc   1200
ggcaagcaag cgcucgaaac ggugcagcgg cuguugccgg ugcugugcca ggaccauggc   1260
cugaccccgg accaaguggu ggcuaucgcc agcaacggug gcggcaagca agcgcucgaa   1320
acggugcagc ggcuguugcc ggugcugugc caggaccaug gccugacccc ggaccaagug   1380
guggcuaucg ccagcaacaa uggcggcaag caagcgcucg aaacggugca gcggcuguug   1440
ccggugcugu gccaggacca uggccugacc ccggaccaag ugguggcuau cgccagcaac   1500
auuggcggca agcaagcgcu cgaaagcauu guggcccagc ugagccggcc ugauccggcg   1560
uuggccgcgu ugaccaacga ccaccucguc gccuuggccu gccucggcgg acguccugcc   1620
```

| | |
|---|---|
| auggaugcag ugaaaaaggg auugccgcac gcgccggaau ugaucagaag agucaaucgc | 1680 |
| cguauuggcg aacgcacguc ccaucgcguu gcgauaucua gagugggagg aagcucgcgc | 1740 |
| agagagucca ucaacccaug gauucugacu gguuucgcug augccgaagg aucauucaua | 1800 |
| cuagacaucc gcaaccgaaa caacgaaagc aacagauacc gaacuucgcu gagauuccag | 1860 |
| aucacccugc acaacaagga caaaucgauu cuggagaaua ccagucgac uuggaagguc | 1920 |
| ggcaagauca caaacagcgg cgacagagcc gucaugcuga gggucacccg uuucgaagau | 1980 |
| uugaaaguga uuaucgacca cuucgagaaa uauccgcuga uuacccagaa auugggcgau | 2040 |
| uacaaguugu uuaaacaggc auucagcguc auggagaaca aagaacaucu uaaggagaau | 2100 |
| gggauuaagg agcucguacg aaucaaagcu aagaugaauu ggggucucac ugacgaauug | 2160 |
| aaaaaagcau uuccagagaa cauuagcaaa gagcgccccc uuaucaauaa gaacauuccg | 2220 |
| aauuucaaau ggcuggcugg auucacaucu ggugauggcu acuucggcgu gaaucuaaaa | 2280 |
| aagguaaagg gcaacgcaaa gguauacgug ggacugagau cucaaucuc acagcacauc | 2340 |
| agagacaaga accugaugaa uucauugaua acauaccuag gcugugguuc caucugggag | 2400 |
| aagaacaagu cugaguucag uuggcucgag uucgucguaa ccaaauucag cgauaucaac | 2460 |
| gacaagauca uuccgguauu ccaggaaaau acucugauug gcgucaaacu cgaggacuuu | 2520 |
| gaagauuggu gcaagguugc caaauugauc gaagagaaga aacaccugac cgaauccggu | 2580 |
| uuggaugaga uuaagaaaau caagcugaac augaacaaag gucgugucuu cuga | 2634 |

<210> SEQ ID NO 27
<211> LENGTH: 2634
<212> TYPE: RNA
<213> ORGANISM: Artificial Sequence
<220> FEATURE:
<223> OTHER INFORMATION: Synthesized NTD variant megaTAL construct

<400> SEQUENCE: 27

| | |
|---|---|
| augggauccg cgccaccuaa gaagaaacgc aaagucggca agcugagcac cuucggcuac | 60 |
| agccagcagc agcaggagaa gaucaagccc aaggccagaa gcaccguggc ccagcaccac | 120 |
| gccgcccuga ucggccacgg cuucacccac gcccacaucg uggagcugag caagcacccc | 180 |
| cccgcccugg gcaccaucgc cgccagauac agcgagauga ucgccgcccu gcccgaggcc | 240 |
| acccacgagg acaucguggg cguggcaag caguggagcg cgccagaaac ccuggaggug | 300 |
| cugcugaugg uggugcagga gcugagagcu ccaccacugc agcuggugac cagccagcug | 360 |
| gugaagaucg ccaagagagg cggcgugacc gccaucgagg ccgucacgc cagccgcaau | 420 |
| gcacugacgg gugccccccu gaaccugacc ccggaccaag ugguggcuau cgccagcaac | 480 |
| auugcggca agcaagcgcu cgaaacggug cagcggcugu ugccggugcu ugccaggac | 540 |
| cauggccuga ccccggacca agugguggcu aucgccagca cauuggcgg caagcaagcg | 600 |
| cucgaaacgg ugcagcggcu guugccggug cugugccagg accauggccu gaccccggac | 660 |
| caaguggugg cuaucgccag caacauuggc ggcaagcaag cgcucgaaac ggugcagcgg | 720 |
| cuguugccgg ugcugugcca ggaccauggc cugaccccgg accaaguggu ggcuaucgcc | 780 |
| agcaacggug gcggcaagca agcgcucgaa acggugcagc ggcuguugcc ggugcugugc | 840 |
| caggaccaug gccugacucc ggaccaaguc gaggcuaucg ccagccacga uggcggcaag | 900 |
| caagcgcucg aaacggugca gcggcuguug ccggugcugu gccaggacca uggccugacu | 960 |
| ccggaccaag uggaggcuau cgccagccac gauggcggca agcaagcgcu cgaaacggug | 1020 |

| | |
|---|---|
| cagcggcugu ugccggugcu gugccaggac cauggccuga ccccggacca agugguggcu | 1080 |
| aucgccagca cauuggcgg caagcaagcg cucgaaacgg ugcagcggcu guugccggug | 1140 |
| cugugccagg accauggccu gaccccggac caaguggugg cuaucgccag caacaauggc | 1200 |
| ggcaagcaag cgcucgaaac ggugcagcgg cuguugccgg ugcugugcca ggaccauggc | 1260 |
| cugaccccgg accaaguggu ggcuaucgcc agcaacggug gcggcaagca agcgcucgaa | 1320 |
| acggugcagc ggcuguugcc ggucugugc caggaccaug gccgaccccc ggaccaagug | 1380 |
| guggcuaucg ccagcaacaa uggcggcaag caagcgcucg aaacggugca gcggcuguug | 1440 |
| ccggugcugu gccaggacca uggccugacc ccggaccaag guggcuau cgccagcaac | 1500 |
| auuggcggca agcaagcgcu cgaaagcauu guggcccagc ugagccggcc ugauccggcg | 1560 |
| uuggccgcgu ugaccaacga ccaccucguc gccuuggccu gccucggcgg acguccugcc | 1620 |
| auggaugcag ugaaaaaggg auugccgcac gcgccggaau ugaucagaag agucaaucgc | 1680 |
| cguauuggcg aacgcacguc ccaucgcguu gcgauaucua gagugggagg aagcucgcgc | 1740 |
| agagaguccsa ucaacccaug gauucugacu gguuucgcgu augccgaagg aucauucaua | 1800 |
| cuagcauccc gcaaccgaaa aacgaaaagc aacagauacc gaacuucgcu gagauuccag | 1860 |
| aucacccugc acaacaagga caaaucgauu cuggagaaua ccagucgac uuggaagguc | 1920 |
| ggcaagauca aaacagcgg cgacagagcc gucaugcuga gggucacccg uucgaagau | 1980 |
| uugaaaguga uuaucgacca cuucgagaaa uaccgcuga uuaccagaa auugggcgau | 2040 |
| uacaaguugu uuaaacaggc auucagcguc auggagaaca agaacaucu uaaggagaau | 2100 |
| gggauuaagg agcucguacg aaucaaagcu aagaugaauu gggcucac ugacgaauug | 2160 |
| aaaaagcau uccagagaa cauuagcaaa gagcgcccc uuaucaauaa gaacauuccg | 2220 |
| aauuucaaau ggcuggcugg auucacaucu ggugauggcu acuucggcgu gaaucuaaaa | 2280 |
| aagguaaagg gcaacgcaaa gguauacgug ggacugagau ucucaaucuc acagcacauc | 2340 |
| agagacaaga accugaugaa uucauugaua acauaccag gcugugguuc caucuggag | 2400 |
| aagaacaagu cugaguucag uuggcucgag uucgucguaa ccaaauucag cgauaucaac | 2460 |
| gacaagauca uuccgguauu ccaggaaaau acucugauug cgucaaacu cgaggacuuu | 2520 |
| gaagauuggu gcaagguugc caaauugauc gaagagaaga acaccugac cgaauccggu | 2580 |
| uuggaugaga uuaagaaaau caagcugaac augaacaaag gucgugucuu cuga | 2634 |

<210> SEQ ID NO 28
<211> LENGTH: 711
<212> TYPE: RNA
<213> ORGANISM: Mus musculus

<400> SEQUENCE: 28

| | |
|---|---|
| augucugagc caccucgggc ugagaccuuu guauuccugg accuagaagc cacugggcuc | 60 |
| ccaaacaugg acccgagau ugcagagaua ucccuuuuug cuguucaccg cucuucccug | 120 |
| gagaacccag aacgggauga uucuggnucc uggugcugc cccguuucu ggacaagcuc | 180 |
| acacugugca ugugcccgga gcgccccuuu acugccaagg ccagugagau uacugguuug | 240 |
| agcagcgaaa gccugaugca cugcgggaag gcugguuuca auggcgcugu gguaaggaca | 300 |
| cugcagggcu uccuaagccg ccaggagggc cccaucugcc uuguggccca caauggcuuc | 360 |
| gauuaugacu ucccacugcu gugcacggag cuacaacguc ugggugccca ucugccccaa | 420 |
| gacacugucu gccuggacac acugccugca uugcggggcc uggaccgugc ucacagccac | 480 |
| ggcaccaggg cucaaggccg caaaagcuac agccuggcca gucucuucca ccgcuacuuc | 540 |

```
caggcugaac ccagugcugc ccauucagca gaaggugaug ugcacacccu gcuucugauc    600
uuccugcauc gugcuccuga gcugcucgcc ugggcagaug agcaggcccg cagcugggcu    660
cauauugagc ccauguacgu gccaccugau gguccaagcc ucgaagccug a             711
```

<210> SEQ ID NO 29
<211> LENGTH: 236
<212> TYPE: PRT
<213> ORGANISM: Mus musculus

<400> SEQUENCE: 29

```
Met Ser Glu Pro Pro Arg Ala Glu Thr Phe Val Phe Leu Asp Leu Glu
1               5                   10                  15

Ala Thr Gly Leu Pro Asn Met Asp Pro Glu Ile Ala Glu Ile Ser Leu
            20                  25                  30

Phe Ala Val His Arg Ser Ser Leu Glu Asn Pro Glu Arg Asp Asp Ser
        35                  40                  45

Gly Ser Leu Val Leu Pro Arg Val Leu Asp Lys Leu Thr Leu Cys Met
    50                  55                  60

Cys Pro Glu Arg Pro Phe Thr Ala Lys Ala Ser Glu Ile Thr Gly Leu
65                  70                  75                  80

Ser Ser Glu Ser Leu Met His Cys Gly Lys Ala Gly Phe Asn Gly Ala
                85                  90                  95

Val Val Arg Thr Leu Gln Gly Phe Leu Ser Arg Gln Glu Gly Pro Ile
            100                 105                 110

Cys Leu Val Ala His Asn Gly Phe Asp Tyr Asp Phe Pro Leu Leu Cys
        115                 120                 125

Thr Glu Leu Gln Arg Leu Gly Ala His Leu Pro Gln Asp Thr Val Cys
    130                 135                 140

Leu Asp Thr Leu Pro Ala Leu Arg Gly Leu Asp Arg Ala His Ser His
145                 150                 155                 160

Gly Thr Arg Ala Gln Gly Arg Lys Ser Tyr Ser Leu Ala Ser Leu Phe
                165                 170                 175

His Arg Tyr Phe Gln Ala Glu Pro Ser Ala Ala His Ser Ala Glu Gly
            180                 185                 190

Asp Val His Thr Leu Leu Leu Ile Phe Leu His Arg Ala Pro Glu Leu
        195                 200                 205

Leu Ala Trp Ala Asp Glu Gln Ala Arg Ser Trp Ala His Ile Glu Pro
    210                 215                 220

Met Tyr Val Pro Pro Asp Gly Pro Ser Leu Glu Ala
225                 230                 235
```

<210> SEQ ID NO 30
<211> LENGTH: 3
<212> TYPE: PRT
<213> ORGANISM: Artificial Sequence
<220> FEATURE:
<223> OTHER INFORMATION: Exemplary linker sequence

<400> SEQUENCE: 30

```
Gly Gly Gly
1
```

<210> SEQ ID NO 31
<211> LENGTH: 5
<212> TYPE: PRT
<213> ORGANISM: Artificial Sequence
<220> FEATURE:

```
<223> OTHER INFORMATION: Exemplary linker sequence

<400> SEQUENCE: 31

Asp Gly Gly Gly Ser
1               5

<210> SEQ ID NO 32
<211> LENGTH: 5
<212> TYPE: PRT
<213> ORGANISM: Artificial Sequence
<220> FEATURE:
<223> OTHER INFORMATION: Exemplary linker sequence

<400> SEQUENCE: 32

Thr Gly Glu Lys Pro
1               5

<210> SEQ ID NO 33
<211> LENGTH: 4
<212> TYPE: PRT
<213> ORGANISM: Artificial Sequence
<220> FEATURE:
<223> OTHER INFORMATION: Exemplary linker sequence

<400> SEQUENCE: 33

Gly Gly Arg Arg
1

<210> SEQ ID NO 34
<211> LENGTH: 5
<212> TYPE: PRT
<213> ORGANISM: Artificial Sequence
<220> FEATURE:
<223> OTHER INFORMATION: Exemplary linker sequence

<400> SEQUENCE: 34

Gly Gly Gly Gly Ser
1               5

<210> SEQ ID NO 35
<211> LENGTH: 14
<212> TYPE: PRT
<213> ORGANISM: Artificial Sequence
<220> FEATURE:
<223> OTHER INFORMATION: Exemplary linker sequence

<400> SEQUENCE: 35

Glu Gly Lys Ser Ser Gly Ser Gly Ser Glu Ser Lys Val Asp
1               5                   10

<210> SEQ ID NO 36
<211> LENGTH: 18
<212> TYPE: PRT
<213> ORGANISM: Artificial Sequence
<220> FEATURE:
<223> OTHER INFORMATION: Exemplary linker sequence

<400> SEQUENCE: 36

Lys Glu Ser Gly Ser Val Ser Ser Glu Gln Leu Ala Gln Phe Arg Ser
1               5                   10                  15

Leu Asp

<210> SEQ ID NO 37
<211> LENGTH: 8
<212> TYPE: PRT
<213> ORGANISM: Artificial Sequence
```

```
<220> FEATURE:
<223> OTHER INFORMATION: Exemplary linker sequence

<400> SEQUENCE: 37

Gly Gly Arg Arg Gly Gly Gly Ser
1               5

<210> SEQ ID NO 38
<211> LENGTH: 9
<212> TYPE: PRT
<213> ORGANISM: Artificial Sequence
<220> FEATURE:
<223> OTHER INFORMATION: Exemplary linker sequence

<400> SEQUENCE: 38

Leu Arg Gln Arg Asp Gly Glu Arg Pro
1               5

<210> SEQ ID NO 39
<211> LENGTH: 12
<212> TYPE: PRT
<213> ORGANISM: Artificial Sequence
<220> FEATURE:
<223> OTHER INFORMATION: Exemplary linker sequence

<400> SEQUENCE: 39

Leu Arg Gln Lys Asp Gly Gly Gly Ser Glu Arg Pro
1               5                   10

<210> SEQ ID NO 40
<211> LENGTH: 16
<212> TYPE: PRT
<213> ORGANISM: Artificial Sequence
<220> FEATURE:
<223> OTHER INFORMATION: Exemplary linker sequence

<400> SEQUENCE: 40

Leu Arg Gln Lys Asp Gly Gly Gly Ser Gly Gly Gly Ser Glu Arg Pro
1               5                   10                  15

<210> SEQ ID NO 41
<211> LENGTH: 7
<212> TYPE: PRT
<213> ORGANISM: Artificial Sequence
<220> FEATURE:
<223> OTHER INFORMATION: Cleavage sequence by TEV protease
<220> FEATURE:
<221> NAME/KEY: misc_feature
<222> LOCATION: (2)..(3)
<223> OTHER INFORMATION: Xaa is any amino acid
<220> FEATURE:
<221> NAME/KEY: misc_feature
<222> LOCATION: (5)..(5)
<223> OTHER INFORMATION: Xaa is any amino acid
<220> FEATURE:
<221> NAME/KEY: MISC_FEATURE
<222> LOCATION: (7)..(7)
<223> OTHER INFORMATION: Xaa = Gly or Ser

<400> SEQUENCE: 41

Glu Xaa Xaa Tyr Xaa Gln Xaa
1               5

<210> SEQ ID NO 42
<211> LENGTH: 7
<212> TYPE: PRT
<213> ORGANISM: Artificial Sequence
<220> FEATURE:
<223> OTHER INFORMATION: Cleavage sequence by TEV protease
```

-continued

```
<400> SEQUENCE: 42

Glu Asn Leu Tyr Phe Gln Gly
1               5

<210> SEQ ID NO 43
<211> LENGTH: 7
<212> TYPE: PRT
<213> ORGANISM: Artificial Sequence
<220> FEATURE:
<223> OTHER INFORMATION: Cleavage sequence by TEV protease

<400> SEQUENCE: 43

Glu Asn Leu Tyr Phe Gln Ser
1               5

<210> SEQ ID NO 44
<211> LENGTH: 22
<212> TYPE: PRT
<213> ORGANISM: Artificial Sequence
<220> FEATURE:
<223> OTHER INFORMATION: Self-cleaving polypeptide comprising 2A site

<400> SEQUENCE: 44

Gly Ser Gly Ala Thr Asn Phe Ser Leu Leu Lys Gln Ala Gly Asp Val
1               5                   10                  15

Glu Glu Asn Pro Gly Pro
            20

<210> SEQ ID NO 45
<211> LENGTH: 19
<212> TYPE: PRT
<213> ORGANISM: Artificial Sequence
<220> FEATURE:
<223> OTHER INFORMATION: Self-cleaving polypeptide comprising 2A site

<400> SEQUENCE: 45

Ala Thr Asn Phe Ser Leu Leu Lys Gln Ala Gly Asp Val Glu Glu Asn
1               5                   10                  15

Pro Gly Pro

<210> SEQ ID NO 46
<211> LENGTH: 14
<212> TYPE: PRT
<213> ORGANISM: Artificial Sequence
<220> FEATURE:
<223> OTHER INFORMATION: Self-cleaving polypeptide comprising 2A site

<400> SEQUENCE: 46

Leu Leu Lys Gln Ala Gly Asp Val Glu Glu Asn Pro Gly Pro
1               5                   10

<210> SEQ ID NO 47
<211> LENGTH: 21
<212> TYPE: PRT
<213> ORGANISM: Artificial Sequence
<220> FEATURE:
<223> OTHER INFORMATION: Self-cleaving polypeptide comprising 2A site

<400> SEQUENCE: 47

Gly Ser Gly Glu Gly Arg Gly Ser Leu Leu Thr Cys Gly Asp Val Glu
1               5                   10                  15

Glu Asn Pro Gly Pro
            20
```

<210> SEQ ID NO 48
<211> LENGTH: 18
<212> TYPE: PRT
<213> ORGANISM: Artificial Sequence
<220> FEATURE:
<223> OTHER INFORMATION: Self-cleaving polypeptide comprising 2A site

<400> SEQUENCE: 48

Glu Gly Arg Gly Ser Leu Leu Thr Cys Gly Asp Val Glu Glu Asn Pro
1               5                   10                  15

Gly Pro

<210> SEQ ID NO 49
<211> LENGTH: 13
<212> TYPE: PRT
<213> ORGANISM: Artificial Sequence
<220> FEATURE:
<223> OTHER INFORMATION: Self-cleaving polypeptide comprising 2A site

<400> SEQUENCE: 49

Leu Leu Thr Cys Gly Asp Val Glu Glu Asn Pro Gly Pro
1               5                   10

<210> SEQ ID NO 50
<211> LENGTH: 23
<212> TYPE: PRT
<213> ORGANISM: Artificial Sequence
<220> FEATURE:
<223> OTHER INFORMATION: Self-cleaving polypeptide comprising 2A site

<400> SEQUENCE: 50

Gly Ser Gly Gln Cys Thr Asn Tyr Ala Leu Leu Lys Leu Ala Gly Asp
1               5                   10                  15

Val Glu Ser Asn Pro Gly Pro
            20

<210> SEQ ID NO 51
<211> LENGTH: 20
<212> TYPE: PRT
<213> ORGANISM: Artificial Sequence
<220> FEATURE:
<223> OTHER INFORMATION: Self-cleaving polypeptide comprising 2A site

<400> SEQUENCE: 51

Gln Cys Thr Asn Tyr Ala Leu Leu Lys Leu Ala Gly Asp Val Glu Ser
1               5                   10                  15

Asn Pro Gly Pro
            20

<210> SEQ ID NO 52
<211> LENGTH: 14
<212> TYPE: PRT
<213> ORGANISM: Artificial Sequence
<220> FEATURE:
<223> OTHER INFORMATION: Self-cleaving polypeptide comprising 2A site

<400> SEQUENCE: 52

Leu Leu Lys Leu Ala Gly Asp Val Glu Ser Asn Pro Gly Pro
1               5                   10

<210> SEQ ID NO 53
<211> LENGTH: 25
<212> TYPE: PRT
<213> ORGANISM: Artificial Sequence
<220> FEATURE:

<223> OTHER INFORMATION: Self-cleaving polypeptide comprising 2A site

<400> SEQUENCE: 53

Gly Ser Gly Val Lys Gln Thr Leu Asn Phe Asp Leu Leu Lys Leu Ala
1               5                   10                  15

Gly Asp Val Glu Ser Asn Pro Gly Pro
            20                  25

<210> SEQ ID NO 54
<211> LENGTH: 22
<212> TYPE: PRT
<213> ORGANISM: Artificial Sequence
<220> FEATURE:
<223> OTHER INFORMATION: Self-cleaving polypeptide comprising 2A site

<400> SEQUENCE: 54

Val Lys Gln Thr Leu Asn Phe Asp Leu Leu Lys Leu Ala Gly Asp Val
1               5                   10                  15

Glu Ser Asn Pro Gly Pro
            20

<210> SEQ ID NO 55
<211> LENGTH: 14
<212> TYPE: PRT
<213> ORGANISM: Artificial Sequence
<220> FEATURE:
<223> OTHER INFORMATION: Self-cleaving polypeptide comprising 2A site

<400> SEQUENCE: 55

Leu Leu Lys Leu Ala Gly Asp Val Glu Ser Asn Pro Gly Pro
1               5                   10

<210> SEQ ID NO 56
<211> LENGTH: 19
<212> TYPE: PRT
<213> ORGANISM: Artificial Sequence
<220> FEATURE:
<223> OTHER INFORMATION: Self-cleaving polypeptide comprising 2A site

<400> SEQUENCE: 56

Leu Leu Asn Phe Asp Leu Leu Lys Leu Ala Gly Asp Val Glu Ser Asn
1               5                   10                  15

Pro Gly Pro

<210> SEQ ID NO 57
<211> LENGTH: 19
<212> TYPE: PRT
<213> ORGANISM: Artificial Sequence
<220> FEATURE:
<223> OTHER INFORMATION: Self-cleaving polypeptide comprising 2A site

<400> SEQUENCE: 57

Thr Leu Asn Phe Asp Leu Leu Lys Leu Ala Gly Asp Val Glu Ser Asn
1               5                   10                  15

Pro Gly Pro

<210> SEQ ID NO 58
<211> LENGTH: 14
<212> TYPE: PRT
<213> ORGANISM: Artificial Sequence
<220> FEATURE:
<223> OTHER INFORMATION: Self-cleaving polypeptide comprising 2A site

<400> SEQUENCE: 58

```
Leu Leu Lys Leu Ala Gly Asp Val Glu Ser Asn Pro Gly Pro
 1               5                  10
```

```
<210> SEQ ID NO 59
<211> LENGTH: 17
<212> TYPE: PRT
<213> ORGANISM: Artificial Sequence
<220> FEATURE:
<223> OTHER INFORMATION: Self-cleaving polypeptide comprising 2A site

<400> SEQUENCE: 59

Asn Phe Asp Leu Leu Lys Leu Ala Gly Asp Val Glu Ser Asn Pro Gly
 1               5                  10                  15

Pro
```

```
<210> SEQ ID NO 60
<211> LENGTH: 20
<212> TYPE: PRT
<213> ORGANISM: Artificial Sequence
<220> FEATURE:
<223> OTHER INFORMATION: Self-cleaving polypeptide comprising 2A site

<400> SEQUENCE: 60

Gln Leu Leu Asn Phe Asp Leu Leu Lys Leu Ala Gly Asp Val Glu Ser
 1               5                  10                  15

Asn Pro Gly Pro
            20
```

```
<210> SEQ ID NO 61
<211> LENGTH: 24
<212> TYPE: PRT
<213> ORGANISM: Artificial Sequence
<220> FEATURE:
<223> OTHER INFORMATION: Self-cleaving polypeptide comprising 2A site

<400> SEQUENCE: 61

Ala Pro Val Lys Gln Thr Leu Asn Phe Asp Leu Leu Lys Leu Ala Gly
 1               5                  10                  15

Asp Val Glu Ser Asn Pro Gly Pro
            20
```

```
<210> SEQ ID NO 62
<211> LENGTH: 40
<212> TYPE: PRT
<213> ORGANISM: Artificial Sequence
<220> FEATURE:
<223> OTHER INFORMATION: Self-cleaving polypeptide comprising 2A site

<400> SEQUENCE: 62

Val Thr Glu Leu Leu Tyr Arg Met Lys Arg Ala Glu Thr Tyr Cys Pro
 1               5                  10                  15

Arg Pro Leu Leu Ala Ile His Pro Thr Glu Ala Arg His Lys Gln Lys
            20                  25                  30

Ile Val Ala Pro Val Lys Gln Thr
                35                  40
```

```
<210> SEQ ID NO 63
<211> LENGTH: 18
<212> TYPE: PRT
<213> ORGANISM: Artificial Sequence
<220> FEATURE:
<223> OTHER INFORMATION: Self-cleaving polypeptide comprising 2A site

<400> SEQUENCE: 63
```

```
Leu Asn Phe Asp Leu Leu Lys Leu Ala Gly Asp Val Glu Ser Asn Pro
1               5                   10                  15

Gly Pro

<210> SEQ ID NO 64
<211> LENGTH: 40
<212> TYPE: PRT
<213> ORGANISM: Artificial Sequence
<220> FEATURE:
<223> OTHER INFORMATION: Self-cleaving polypeptide comprising 2A site

<400> SEQUENCE: 64

Leu Leu Ala Ile His Pro Thr Glu Ala Arg His Lys Gln Lys Ile Val
1               5                   10                  15

Ala Pro Val Lys Gln Thr Leu Asn Phe Asp Leu Leu Lys Leu Ala Gly
            20                  25                  30

Asp Val Glu Ser Asn Pro Gly Pro
        35                  40

<210> SEQ ID NO 65
<211> LENGTH: 33
<212> TYPE: PRT
<213> ORGANISM: Artificial Sequence
<220> FEATURE:
<223> OTHER INFORMATION: Self-cleaving polypeptide comprising 2A site

<400> SEQUENCE: 65

Glu Ala Arg His Lys Gln Lys Ile Val Ala Pro Val Lys Gln Thr Leu
1               5                   10                  15

Asn Phe Asp Leu Leu Lys Leu Ala Gly Asp Val Glu Ser Asn Pro Gly
            20                  25                  30

Pro

<210> SEQ ID NO 66
<211> LENGTH: 10
<212> TYPE: DNA
<213> ORGANISM: Artificial Sequence
<220> FEATURE:
<223> OTHER INFORMATION: Consensus Kozak sequence

<400> SEQUENCE: 66 gccrccatgg                                                          10

<210> SEQ ID NO 67
<211> LENGTH: 22
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(14)
<223> OTHER INFORMATION: n is a, c, g, or t
<220> FEATURE:
<221> NAME/KEY: misc_feature
<222> LOCATION: (18)..(22)
<223> OTHER INFORMATION: n is a, c, g, or t

<400> SEQUENCE: 67
nnnnnnnnnn nnnnccgnnn nn                                            22

<210> SEQ ID NO 68
<211> LENGTH: 47
<212> TYPE: DNA
<213> ORGANISM: Homo sapiens
```

```
<400> SEQUENCE: 68
actctaaatc cagtgacaag tctgtctgcc tattcaccga ttttgat                    47

<210> SEQ ID NO 69
<211> LENGTH: 47
<212> TYPE: DNA
<213> ORGANISM: Homo sapiens

<400> SEQUENCE: 69
atcaaaatcg gtgaataggc agacagactt gtcactggat ttagagt                    47
```